(12) United States Patent
Colby

(10) Patent No.: US 11,583,337 B2
(45) Date of Patent: Feb. 21, 2023

(54) ABLATION PROBE SYSTEMS

(71) Applicant: TriAgenics, Inc., Redmond, OR (US)

(72) Inventor: Leigh E. Colby, Lino Lakes, MN (US)

(73) Assignee: TriAgenics, Inc., Redmond, OR (US)

( * ) Notice: Subject to any disclaimer, the term of this patent is extended or adjusted under 35 U.S.C. 154(b) by 0 days.

(21) Appl. No.: 17/543,582

(22) Filed: Dec. 6, 2021

(65) Prior Publication Data

US 2022/0087744 A1    Mar. 24, 2022

Related U.S. Application Data

(63) Continuation of application No. PCT/US2020/036705, filed on Jun. 8, 2020, and a
(Continued)

(51) Int. Cl.
*A61B 18/18* (2006.01)
*A61B 18/00* (2006.01)

(52) U.S. Cl.
CPC ............ *A61B 18/1815* (2013.01); *A61B 2018/00005* (2013.01); *A61B 2018/00273* (2013.01);
(Continued)

(58) Field of Classification Search
CPC ............ A61B 18/1477; A61B 18/1815; A61B 2018/00005; A61B 2018/00017;
(Continued)

(56) References Cited

U.S. PATENT DOCUMENTS

| | | |
|---|---|---|
| 610,355 A | 9/1898 | Kinne et al. |
| 752,378 A | 2/1904 | Dailey |

(Continued)

FOREIGN PATENT DOCUMENTS

| | | |
|---|---|---|
| AU | 2010247874 | 11/2010 |
| AU | 2015213338 | 9/2015 |

(Continued)

OTHER PUBLICATIONS

Qi H., "CT-guided microwave ablation through the lungs for treating liver tumors near the diaphragm," Clinical Research Paper, Oncotarget Journal, 2017, vol. 8, (No. 45), pp. 79270-79278, 9 pages, www.impactjournals.com/oncotarget/.
(Continued)

*Primary Examiner* — Michael F Peffley
(74) *Attorney, Agent, or Firm* — Law Office of Karen Dana Oster, LLC

(57) ABSTRACT

An ablation probe tip 100 having a shaft 102 with an insertion end 104 and an annular aperture 120 near the insertion end 104. A center of ablation 124 is located within the shaft 102 and surrounded by the annular aperture shaft 102. The ablation probe tip 100 may be part of an ablation probe system 50 that includes an ablation source 60 that provides ablation means 62 to the ablation probe tip 100. The center of ablation 124 is a focal region from which the ablation means 62 radiates through the annular aperture 120 to form an ablation zone 150, 160, 170. The system 50 has at least one intra-operative control selected from the group of: ablation zone positioning control, ablation zone shaping control, ablation center control, ablation zone temperature control, guided ablation volume/diameter control, and power loading control.

27 Claims, 27 Drawing Sheets

Related U.S. Application Data continuation-in-part of application No. PCT/US2020/036508, filed on Jun. 5, 2020.

(60) Provisional application No. 62/876,574, filed on Jul. 19, 2019, provisional application No. 62/858,230, filed on Jun. 6, 2019.

(52) U.S. Cl.
CPC .............. *A61B 2018/00577* (2013.01); *A61B 2018/1861* (2013.01); *A61B 2018/1892* (2013.01)

(58) Field of Classification Search
CPC ........... A61B 2018/00023; A61B 2018/00029; A61B 2018/00273; A61B 2018/00565; A61B 2018/00577; A61B 2018/00642; A61B 2018/00785; A61B 2018/00791; A61B 2018/00803; A61B 2018/1853; A61B 2018/1861; A61B 2018/1869; A61B 2018/1892
See application file for complete search history.

(56) References Cited

U.S. PATENT DOCUMENTS

| | | |
|---|---|---|
| 1,713,971 A | 5/1929 | Lowry et al. |
| 2,317,648 A | 4/1943 | Siqveland |
| 4,672,963 A | 6/1987 | Barken |
| 4,700,716 A * | 10/1987 | Kasevich .............. A61B 18/18 607/156 |
| 4,895,517 A | 1/1990 | Fischer |
| 4,925,523 A | 5/1990 | Braren et al. |
| 5,009,595 A | 4/1991 | Osborn |
| 5,015,183 A | 5/1991 | Fenick |
| 5,133,660 A | 7/1992 | Fenick |
| 5,500,012 A | 3/1996 | Brucker et al. |
| 5,556,278 A | 9/1996 | Meitner |
| 5,613,852 A | 3/1997 | Bavitz |
| 5,623,931 A | 4/1997 | Wung et al. |
| 5,642,997 A | 7/1997 | Gregg, II et al. |
| 5,688,118 A | 11/1997 | Hayka et al. |
| 5,725,376 A | 3/1998 | Poirier |
| 5,768,134 A | 6/1998 | Swaelens et al. |
| 5,792,140 A | 8/1998 | Tu et al. |
| 5,800,168 A | 9/1998 | Cascione et al. |
| 5,816,814 A | 10/1998 | Venta et al. |
| 5,842,858 A | 12/1998 | Truppe |
| 5,843,021 A | 12/1998 | Edwards et al. |
| 5,851,112 A | 12/1998 | Daikuzono et al. |
| 5,906,609 A | 5/1999 | Assa et al. |
| 5,916,213 A | 6/1999 | Haissaguerre et al. |
| 5,941,845 A | 8/1999 | Tu et al. |
| 5,941,889 A | 8/1999 | Cermak |
| 5,943,719 A | 8/1999 | Feldman et al. |
| 5,967,777 A | 10/1999 | Klein et al. |
| 6,027,497 A | 2/2000 | Daniel et al. |
| 6,162,052 A | 12/2000 | Kokubu |
| 6,179,803 B1 | 1/2001 | Edwards et al. |
| 6,179,830 B1 | 1/2001 | Kokubu |
| 6,203,499 B1 | 3/2001 | Imling et al. |
| 6,210,355 B1 | 4/2001 | Edwards et al. |
| 6,241,725 B1 | 6/2001 | Cosman |
| 6,245,062 B1 | 6/2001 | Berube et al. |
| 6,270,476 B1 | 8/2001 | Santoianni et al. |
| 6,319,006 B1 | 11/2001 | Scherer et al. |
| 6,386,869 B1 | 5/2002 | Zegarelli |
| 6,607,524 B1 | 8/2003 | LaBudde et al. |
| 6,621,491 B1 | 9/2003 | Baumrind et al. |
| 6,622,731 B2 | 9/2003 | Daniel et al. |
| 6,913,463 B2 | 7/2005 | Blacklock |
| 6,936,046 B2 | 8/2005 | Hissong et al. |
| 6,971,877 B2 | 12/2005 | Harter |
| 7,014,461 B2 | 3/2006 | Weinstein |
| 7,044,735 B2 | 5/2006 | Malin |
| 7,097,451 B2 | 8/2006 | Tang |
| 7,169,155 B2 | 1/2007 | Chu et al. |
| 7,226,288 B2 | 6/2007 | Schoeffel |
| 7,249,952 B2 | 7/2007 | Ranta et al. |
| 7,346,417 B2 | 3/2008 | Luth et al. |
| 7,457,443 B2 | 11/2008 | Persky |
| 7,467,015 B2 | 12/2008 | van der Weide |
| 7,492,987 B2 | 2/2009 | Yeik et al. |
| 7,520,877 B2 | 4/2009 | Lee, Jr. et al. |
| 7,553,309 B2 | 6/2009 | Buysse et al. |
| 7,565,190 B2 | 7/2009 | Okerlund et al. |
| 7,611,508 B2 | 11/2009 | Yang et al. |
| 7,615,047 B2 | 11/2009 | Berna et al. |
| 7,725,151 B2 | 5/2010 | van der Weide |
| 7,736,357 B2 | 6/2010 | Lee, Jr. et al. |
| 7,776,035 B2 | 8/2010 | Rick et al. |
| 7,787,132 B2 | 8/2010 | Körner et al. |
| 7,812,815 B2 | 10/2010 | Banerjee et al. |
| 7,819,591 B2 | 10/2010 | Rohaly et al. |
| 7,822,466 B2 | 10/2010 | Stoisnovici et al. |
| 7,959,441 B2 | 6/2011 | Glover et al. |
| 7,976,469 B2 | 7/2011 | Bonde et al. |
| 7,990,548 B2 | 8/2011 | Babayoff et al. |
| 8,013,853 B1 | 9/2011 | Douglas et al. |
| 8,048,067 B2 | 11/2011 | Davalos et al. |
| 8,057,487 B2 | 11/2011 | Chu et al. |
| 8,211,099 B2 | 7/2012 | Buysse et al. |
| 8,221,121 B2 | 7/2012 | Berckmans et al. |
| 8,257,341 B1 | 9/2012 | Fletcher |
| 8,310,683 B2 | 11/2012 | Babayoff et al. |
| 8,363,228 B2 | 1/2013 | Babayoff |
| 8,372,061 B2 | 2/2013 | Berna et al. |
| 8,377,057 B2 | 2/2013 | Rick et al. |
| 8,480,666 B2 | 7/2013 | Buysse et al. |
| 8,626,317 B2 | 1/2014 | Higgins |
| 8,670,816 B2 | 3/2014 | Green et al. |
| 8,672,932 B2 | 3/2014 | van der Weide et al. |
| 8,834,409 B2 | 9/2014 | Manley |
| 8,892,235 B2 | 11/2014 | Choi et al. |
| 8,945,144 B2 | 2/2015 | Cunningham |
| 8,979,871 B2 | 3/2015 | Tyc et al. |
| 9,028,252 B1 | 5/2015 | Shabat |
| 9,066,712 B2 | 6/2015 | Fourkas et al. |
| 9,072,532 B2 | 7/2015 | van der Weide et al. |
| 9,113,912 B1 | 8/2015 | Mehta et al. |
| 9,119,628 B1 | 9/2015 | Mehta et al. |
| 9,119,649 B2 | 9/2015 | van der Weide et al. |
| 9,168,091 B2 | 10/2015 | Janssen et al. |
| 9,192,438 B2 | 11/2015 | Thiel et al. |
| 9,271,796 B2 | 3/2016 | Buysse et al. |
| 9,402,691 B2 | 8/2016 | Merritt et al. |
| 9,402,693 B2 | 8/2016 | Colby |
| 9,415,194 B2 | 8/2016 | Wolf et al. |
| 9,439,608 B2 | 9/2016 | Schutyser et al. |
| 9,566,115 B2 | 2/2017 | van der Weide et al. |
| 9,597,160 B1 | 3/2017 | Greg, II et al. |
| 9,622,813 B2 | 4/2017 | Krugman et al. |
| 9,724,236 B2 | 8/2017 | Abe |
| 9,827,068 B2 | 11/2017 | Colby |
| 9,844,324 B2 | 12/2017 | Merritt et al. |
| 9,855,112 B2 | 1/2018 | Colby |
| 9,861,440 B2 | 1/2018 | van der Weide et al. |
| 9,872,729 B2 | 1/2018 | van der Weide et al. |
| 9,877,783 B2 | 1/2018 | van der Weide et al. |
| 9,943,374 B2 | 4/2018 | Merritt et al. |
| 9,943,379 B2 | 4/2018 | Greg, II et al. |
| 10,022,202 B2 | 7/2018 | Colby |
| 10,265,140 B2 | 4/2019 | Colby |
| 10,285,778 B2 | 5/2019 | Colby |
| 10,298,255 B2 | 5/2019 | Colby |
| 10,299,885 B2 | 5/2019 | Colby |
| 10,335,248 B2 | 7/2019 | Colby |
| 10,350,008 B2 | 7/2019 | Gibbs et al. |
| 10,355,248 B2 | 7/2019 | Colby |
| 10,765,490 B2 | 9/2020 | Colby |
| 10,820,963 B2 | 11/2020 | Colby |
| 11,173,012 B2 | 11/2021 | Colby |
| 11,399,915 B2 | 8/2022 | Colby |

(56) References Cited

U.S. PATENT DOCUMENTS

| | | |
|---|---|---|
| 2002/0022864 A1 | 2/2002 | Mahvi et al. |
| 2002/0058872 A1 | 5/2002 | Steininger et al. |
| 2002/0128642 A1 | 9/2002 | Berube et al. |
| 2002/0160337 A1 | 10/2002 | Klein et al. |
| 2003/0130575 A1 | 7/2003 | Desai |
| 2004/0097805 A1 | 5/2004 | Verard et al. |
| 2004/0102767 A1 | 5/2004 | Stingl et al. |
| 2004/0147915 A1 | 7/2004 | Hasebe |
| 2004/0157188 A1 | 8/2004 | Luth et al. |
| 2004/0158194 A1 | 8/2004 | Wolff et al. |
| 2004/0215186 A1 | 10/2004 | Cornelius et al. |
| 2004/0219482 A1 | 11/2004 | Bina et al. |
| 2004/0230187 A1 | 11/2004 | Lee et al. |
| 2004/0249370 A1 | 12/2004 | Berna et al. |
| 2005/0090820 A1 | 4/2005 | Cornelius et al. |
| 2005/0170312 A1 | 8/2005 | Pond |
| 2005/0177074 A1 | 8/2005 | Becker et al. |
| 2005/0186533 A1 | 8/2005 | Cohen |
| 2005/0283148 A1 | 12/2005 | Janssen et al. |
| 2006/0009404 A1 | 1/2006 | Williams |
| 2006/0074413 A1 | 4/2006 | Behzadian |
| 2006/0084958 A1 | 4/2006 | Raif et al. |
| 2006/0111705 A1 | 5/2006 | Janzen et al. |
| 2006/0115782 A1 | 6/2006 | Li et al. |
| 2006/0125572 A1 | 6/2006 | van der Weide et al. |
| 2006/0127859 A1 | 6/2006 | Wen |
| 2006/0195169 A1 | 8/2006 | Gross et al. |
| 2006/0240378 A1 | 10/2006 | Weinstein et al. |
| 2006/0265139 A1 | 11/2006 | van der Weide et al. |
| 2006/0276781 A1 | 12/2006 | van der Weide et al. |
| 2006/0278825 A1 | 12/2006 | van der Weide et al. |
| 2007/0016181 A1 | 1/2007 | van der Weide et al. |
| 2007/0016183 A1 | 1/2007 | Lee et al. |
| 2007/0049917 A1* | 3/2007 | Yang ................. A61B 18/1815 607/101 |
| 2007/0049918 A1 | 3/2007 | van der Weide et al. |
| 2007/0055224 A1 | 3/2007 | Lee, Jr. et al. |
| 2007/0135707 A1 | 6/2007 | Redel et al. |
| 2007/0179485 A1 | 8/2007 | Yeik et al. |
| 2007/0203551 A1* | 8/2007 | Cronin ................. A61B 18/18 607/101 |
| 2007/0224570 A1 | 9/2007 | West et al. |
| 2007/0265628 A1 | 11/2007 | Kraus et al. |
| 2007/0288079 A1 | 12/2007 | van der Weide et al. |
| 2007/0293756 A1 | 12/2007 | Jung et al. |
| 2007/0294280 A1 | 12/2007 | Jung et al. |
| 2008/0009747 A1 | 1/2008 | Saadat et al. |
| 2008/0033422 A1* | 2/2008 | Turner ............... A61B 18/1815 607/102 |
| 2008/0033424 A1 | 2/2008 | van der Weide et al. |
| 2008/0039709 A1 | 2/2008 | Karmarkar |
| 2008/0045938 A1 | 2/2008 | van der Weide et al. |
| 2008/0119921 A1 | 5/2008 | Brace et al. |
| 2008/0138761 A1 | 6/2008 | Pond |
| 2008/0147056 A1 | 6/2008 | van der Weide et al. |
| 2008/0176187 A1 | 7/2008 | Stumpel |
| 2008/0182218 A1 | 7/2008 | Chen et al. |
| 2008/0199829 A1 | 8/2008 | Paley et al. |
| 2009/0011382 A1 | 1/2009 | Bavar |
| 2009/0041198 A1 | 2/2009 | Price et al. |
| 2009/0062790 A1 | 3/2009 | Malchano et al. |
| 2009/0076498 A1 | 3/2009 | Saadat et al. |
| 2009/0088830 A1 | 4/2009 | Mohamed et al. |
| 2009/0118613 A1 | 5/2009 | Krugman et al. |
| 2009/0136902 A1 | 5/2009 | Zundorf et al. |
| 2009/0253095 A1 | 10/2009 | Salcedo et al. |
| 2009/0258330 A1 | 10/2009 | Huber et al. |
| 2009/0263764 A1 | 10/2009 | Berckmans et al. |
| 2009/0306652 A1 | 12/2009 | Buysse et al. |
| 2010/0021866 A1 | 1/2010 | Tsuji et al. |
| 2010/0035201 A1 | 2/2010 | Beck et al. |
| 2010/0082032 A1 | 4/2010 | Berna et al. |
| 2010/0100094 A1 | 4/2010 | Truckai |
| 2010/0114184 A1 | 5/2010 | Degtyar et al. |
| 2010/0129771 A1 | 5/2010 | Tsuji et al. |
| 2010/0203479 A1 | 8/2010 | Bulloch et al. |
| 2010/0268219 A1* | 10/2010 | Ormsby ................. A61B 18/18 606/33 |
| 2010/0311006 A1 | 12/2010 | Lancieux et al. |
| 2010/0311028 A1 | 12/2010 | Bell, III et al. |
| 2010/0316974 A1 | 12/2010 | Yau et al. |
| 2011/0098697 A1 | 4/2011 | Brannan |
| 2011/0104632 A1 | 5/2011 | Colby |
| 2011/0130689 A1 | 6/2011 | Cohen et al. |
| 2011/0137156 A1 | 6/2011 | Razzaque et al. |
| 2011/0200960 A1 | 8/2011 | Colby |
| 2011/0200961 A1 | 8/2011 | Colby |
| 2011/0238060 A1 | 9/2011 | Lee, Jr. et al. |
| 2011/0238061 A1 | 9/2011 | van der Weide et al. |
| 2011/0244417 A1 | 10/2011 | Hilsen et al. |
| 2012/0046536 A1 | 2/2012 | Cheung et al. |
| 2012/0053577 A1 | 3/2012 | Lee et al. |
| 2012/0100500 A1 | 4/2012 | Gao |
| 2012/0143180 A1 | 6/2012 | Lee, Jr. et al. |
| 2013/0017507 A1 | 1/2013 | Moffson et al. |
| 2013/0150843 A1 | 6/2013 | Berna et al. |
| 2013/0172731 A1 | 7/2013 | Gole |
| 2013/0197355 A1 | 8/2013 | Lee et al. |
| 2014/0066917 A1 | 3/2014 | Cosman, Jr. et al. |
| 2014/0081260 A1 | 3/2014 | Cosman, Jr. et al. |
| 2014/0093838 A1 | 4/2014 | Carmichael et al. |
| 2014/0121658 A1 | 5/2014 | Cosman, Jr. et al. |
| 2014/0186796 A1 | 7/2014 | Suttin |
| 2014/0193771 A1 | 7/2014 | Dolfi et al. |
| 2014/0257272 A1 | 9/2014 | Clark, III et al. |
| 2014/0276033 A1 | 9/2014 | Brannan et al. |
| 2014/0378964 A1 | 12/2014 | Pearson |
| 2015/0018801 A1 | 1/2015 | Lazarof |
| 2015/0018822 A1 | 1/2015 | Racz |
| 2015/0133909 A1 | 5/2015 | van der Weide et al. |
| 2015/0147714 A1 | 5/2015 | Daon |
| 2015/0150631 A1 | 7/2015 | Lee |
| 2015/0265371 A1 | 9/2015 | Kim |
| 2015/0272671 A1 | 10/2015 | van der Weide et al. |
| 2015/0351831 A1 | 12/2015 | Janssen et al. |
| 2015/0374456 A1* | 12/2015 | Colby ................. A61B 34/20 433/25 |
| 2015/0374457 A1 | 12/2015 | Colby |
| 2016/0106518 A1 | 4/2016 | Choi et al. |
| 2016/0151113 A1 | 6/2016 | Kim et al. |
| 2016/0157967 A1 | 6/2016 | Kim et al. |
| 2016/0324597 A1 | 11/2016 | Colby |
| 2016/0367318 A1 | 12/2016 | van der Weide et al. |
| 2017/0014185 A1 | 1/2017 | Lee, Jr. et al. |
| 2017/0039489 A1 | 2/2017 | Reh et al. |
| 2017/0231718 A1 | 8/2017 | Wohrle et al. |
| 2017/0290554 A1 | 10/2017 | Merritt |
| 2017/0360528 A1 | 12/2017 | Colby |
| 2018/0014910 A1 | 1/2018 | Colby |
| 2018/0078309 A1 | 3/2018 | Van der Weide et al. |
| 2018/0091169 A1 | 3/2018 | Colby |
| 2018/0125579 A1 | 5/2018 | Van der Weide et al. |
| 2018/0132934 A1 | 5/2018 | van der Weide et al. |
| 2018/0153640 A1 | 6/2018 | Colby |
| 2018/0261922 A1 | 9/2018 | Behdad et al. |
| 2018/0318038 A1 | 11/2018 | Colby |
| 2019/0029751 A1 | 1/2019 | Hancock et al. |
| 2021/0007829 A1 | 1/2021 | Colby |
| 2022/0047356 A1 | 2/2022 | Colby |

FOREIGN PATENT DOCUMENTS

| | | |
|---|---|---|
| AU | 2017/202885 | 7/2019 |
| AU | 2019/204646 | 12/2020 |
| AU | 2020217369 | 12/2021 |
| CA | 2761652 | 10/2019 |
| CA | 2939815 | 8/2020 |
| CA | 2939821 | 8/2020 |
| DE | 19510294 | 10/1996 |
| EP | 1210022 | 4/2006 |
| EP | 2301469 | 3/2011 |
| EP | 2429444 | 3/2012 |
| EP | 3228272 | 10/2017 |
| FR | 2925289 | 1/2011 |

(56) References Cited

FOREIGN PATENT DOCUMENTS

| GB | 2057888 | 4/1981 |
|---|---|---|
| MX | 357449 | 7/2018 |
| WO | WO 2004084748 | 10/2004 |
| WO | WO 2006031317 | 6/2006 |
| WO | WO 2007/057902 | 5/2007 |
| WO | WO 2007057902 | 5/2007 |
| WO | WO 2007085719 | 8/2007 |
| WO | WO 2008067334 | 6/2008 |
| WO | WO 2008128720 | 10/2008 |
| WO | WO 2010132368 | 11/2010 |
| WO | WO 2011017168 | 2/2011 |
| WO | WO 2014/143014 | 9/2014 |
| WO | WO2014/152519 | 9/2014 |
| WO | WO 2014152519 | 9/2014 |
| WO | WO 2017103209 | 6/2017 |

OTHER PUBLICATIONS

Yang, Deshan; "Measurements, Antenna Design and Advanced Computer Modeling for Microwave Tissue Ablation"; Ph.D. Dissertation; University of Wisconsin-Madison; 2005; Madison, WI, USA; 272 pages.

AAOMS; "Evidence Based Third Molar Surgery;" American Association of Oral and Maxillofacial Surgeons; Nov. 10, 2011; USA; 5 pages.

AAOMS; "White Paper on Third Molar Data;" American Association of Oral and Maxillofacial Surgeons Article; Mar. 2007; published at www.aaoms.org; 25 pages.

Ahmad, et al.; "Caries Experience and Periodontal Pathology in Erupting Third Molars;" Abstract; Journal of Oral and Maxillofacial Surgery; 2008; 66(5):948-53 (ISSN: 1531-5053); Chapel Hill, NC 27599, USA; 1 page.

Al-Khateeb, et al.; "Pathology Associated with Impacted Mandibular Third Molars in a Group of Jordanians;" Abstract; 2006; Journal of Oral and Maxillofacial Surgery 64(11): 1598-602; Irbid, Jordan; 1 page.

American Dental Association; "Growth in Dental Spending Expected to Slow in 2009;" Web Article; Feb. 26, 2009; published at www.ada.org; 1 page.

American Public Health Association; "Opposition to Prophylactic Removal of Third Molars (Wisdom Teeth);" Policy No. 20085; Oct. 28, 2008; American Public Health Association Policy Statement Database; Washington, DC 20001, USA; 5 pages.

Askboots; "Removing Wisdom Teeth;" Web Article; Sep. 21, 2007; BMJ Publishing Group Limited; published at www.askboots.com; 9 pages.

Australian Government, IP Australia; "Patent Examination Report No. 1 (2010247874);" Jan. 2, 2014; Australia; 3 pages.

Bataineh, A. B.; "Sensory Nerve Impairment Following Mandibular Third Molar Surgery;" Abstract; 2001; Journal of Oral and Maxillofacial Surgery 59(9): 1012-7 (ISSN: 0278-2391); Irbid, Jordan; 1 page.

Blakey, et al.; "Impact of Removal of Asymptomatic Third Molars on Periodontal Pathology;" Abstract; Feb. 2009; Journal of Oral and Maxillofacial Surgery 67(2): 245-50; Chapel Hill, NC 27599, USA; 2 pages.

Blakey, et al.; "Periodontal Pathology Associated with Asymptomatic Third Molars;" Abstract; 2002; Journal of Oral and Maxillofacial Surgery60(11): 1227-33 (ISSN: 0278-2391); Chapel Hill, NC 27599, USA; 1 page.

Blankenship, et al.; "Third Molar Development in the Estimation of Chronologic Age in American Blacks as Compared with Whites;" 2007; Article; Journal of Forensic Science 52(2): 428-33; Memphis, TN 38163, USA; 6 pages.

Blankenship, et al.; "Third Molar Development in the Estimation of Chronologic Age in American Blacks as Compared with Whites;" Abstract; 2007; Journal of Forensic Science, 52(2): 428-33; Memphis, TN 38163, USA; 1 page.

Blondeau, et al.; "Extraction of Impacted Mandibular Third Molars: Postoperative Complications and Their Risk Factors;" Abstract; Journal of the Canadian Dental Association; vol. 73, No. 4, (ISSN: 1488-2159); May 2007; Ottawa, Canada; 2 pages.

Brace, et al.; "Pulmonary Thermal Ablation: Comparison of Radiofrequency and Microwave Devices by Using Gross Pathologic and CT Findings in a Swine Model;" Abstract; Jun. 2009; Radiology, vol. 251, 705-11; Madison, WI 53792, USA; 2 pages.

Brace, C. L.; "Microwave Ablation Technology Avoids Problems that Plague RFA, Offers Promise for New Applications;" Article; Mar. 13, 2006; Diagnostic Imaging; Madison, WI 53792, USA; 2 pages.

Bui, et al.; "Types, Frequencies, and Risk Factors for Complications After Third Molar Extraction;" Article; 2003; Journal of Oral and Maxillofacial Surgery, 61:1379-1389; Chapel Hill, NC 27599, USA; 11 pages.

Christiaens, et al.; "Complications After Third Molar Extractions Retrospective Analysis of 1,213 Teeth;" Abstract; 2002; Rev Stomatol Chir Maxillofac, 103(5):269-74 (ISSN: 0035-1768); Belgique, France; 2 pages.

Dodson, T. B.; "Response to APHA C3: Opposition to Prophylactic Removal of Third Molars;" Article; Oct. 26, 2008; Massachusetts General Hospital; Boston, MA 02114, USA; 3 pages.

Dodson, et al.; "Introduction;" Sep. 2012; pp. S2-S3; Journal of Oral and Maxillofacial Surgery, vol. 70, No. 9, Supplement 1; American Association of Oral and Maxillofacial Surgeons; published online at http://dx.doi.org/10.1016/j.joms.2012.04.022; USA; 2 pages.

Dodson, et al.; "Summary of the Proceedings of the Third Molar Multidisciplinary Conference;" Sep. 2012; pp. S66-S69; Journal of Oral and Maxillofacial Surgery vol. 70, No. 9, Supplement 1; American Association of Oral and Maxillofacial Surgeons; published online at http://dx.doi.org/10.1016/j.joms.2012.05.001; USA; 4 pages.

Eklund, et al.; "Third-Molar Removal Patterns in an Insured Population;" Article; 2001; pp. 469-475; Journal of the American Dental Association, vol. 132, No. 4; USA; 16 pages.

Elter, et al.; "Third Molars Associated with Periodontal Pathology in Older Americans;" Abstract; Feb. 2005; Journal of Oral and Maxillofacial Surgery, 63(2): 179-84; Chapel Hill, NC 27599, USA; 1 page.

Elter, et al.; "Third Molars Associated with Periodontal Pathology in the Third National Health and Nutrition Examination Survey;" Abstract; 2004 Journal of Oral and Maxillofacial Surgery, 62(4):440-5; Chapel Hill, NC 27599, USA; 1 page.

European Patent Office; European Search Report including the European Search Opinion and Supplementary European Search Report for European Patent Application No. EP 10775341.0; dated Jul. 11, 2014; 8 pages.

Fox, M.; "Shots Kill Budding Wisdom Teeth, Study Suggests;" Article; Apr. 3, 2013; NBC News; published online at http://vitals.nbcnews.com/_news/2013/04/03/17584797-shots-kill-budding-wisdom-teeth-studysuggests%0D%0A%0D%0ANBCNews.com; New York, NY, USA;13 pages.

Friedman, J. W.; "Containing the Cost of Third-Molar Extractions: a Dilemma for Health Insurance;" Article; Jul.-Aug. 1983; pp. 376-384; Public Health Reports, vol. 98, No. 4; Los Angeles, CA 90057, USA; 9 pages.

Friedman, J. W.; "Opposition to Prophylactic Removal of Third Molars;" Feb. 18, 2008; pp. 1-10; APHA Oral Health Section; USA; 10 pages.

Friedman, J. W.; "The Prophylactic Extraction of Third Molars: A Public Health Hazard;" Article; Sep. 2007; pp. 1554-1559; American Journal of Public Health, vol. 97, No. 9; Los Angeles, CA, USA; 6 pages.

Gordon, et al.; "The Effects of Local Hypothermia on Odontogenesis;" Article; Apr. 1979; Journal of Oral Surgery, 37(4):235-44; PubMed—indexed for Medline; USA; 10 pages.

Gordon, et al.; "The Effects of Local Hypothermia on Odontogenesis;" Abstract; Apr. 1979; Journal of Oral Surgery, 37(4):235-44; PMID 285227, PubMed—indexed for Medline; USA; 1 page.

(56) References Cited

OTHER PUBLICATIONS

Guralnick, et al.; "Removal of Third Molars;" National Institutes of Health (NIH) Consensus Development Conference Statement; Nov. 28-30, 1979; NIH Consens Statement Nov. 28-30, 1979, 2(11):65-68; USA; 5 pages.

Harrison, L.; "Nerve Blocks in Children May Destroy Future Molars;" Article; Apr. 8, 2013; Medscape Medical News ©2013 WebMD, LLC; published online at www.medscape.com; USA; 2 pages.

Hicks, E. P.; "Third Molar Management: a Case Against Routine Removal in Adolescent and Young Adult Orthodontic Patients;" Abstract; 1999; Journal of Oral and Maxillofacial Surgery, 57(7):831-6; Lexington, KY, USA; 2 pages.

Huang, et al.; "Third-Molar Extraction as a Risk Factor for Temporomandibular Disorder;" Article; 2006; pp. 1547-1554; Journal of the American Dental Association, vol. 137, No. 11; USA; 14 pages.

Itero; "OrthoCAD, A Digitally Perfect Orthodontic Impression;" Webpage; 2009; published online by Cadent Ltd. at www.cadentic.com; 7 pages.

Jiang, P.; "Ten-Year Insurance Claims Data Study Reveals Increase in Utilization of Surgical Extraction Codes;" Online Periodical; Delta Dental of Minnesota, Winter 2006/2007; Eagan, MN 55122, USA; 2 pages.

Kajii, et al.; "Presence of Third Molar Germs in Orthodontic Patients in Japan;" Abstract; Mar. 2001; pp. 245-250; American Journal of Orthodontics & Dentofacial Orthopedics, vol. 119, Issue 3; 2 pages.

Kaminishi, et al.; "A 10-year Comparative Study of the Incidence of Third Molar Removal in the Aging Population;" Abstract; 2006; Journal of Oral Maxillofacial Surgery, 64(2): 173-4 (ISSN: 0278-2391); Los Angeles, CA, USA; 1 page.

Kaminishi, et al.; "New Considerations in the Treatment of Compromised Third Molars;" Abstract; 2004; Journal of the California Dental Association, 32(10):823-5 (ISSN: 1043-2256); Los Angeles, CA, USA; 1 page.

Kan, et al.; "Residual Periodontal Defects Distal to the Mandibular Second Molar 6-36 Months after Impacted Third Molar Extraction;" Abstract; Nov. 2002; Journal of Clinical Periodontology, 29(11):1004-11; Hong Kong SAR, China; 1 page.

Kiukkonen; "Toxicity of Dioxin to Developing Teeth and Salivary Glands;" Dissertation; Jun. 16, 2006; Helsinki University Biomedical Dissertations No. 77; Finland; 94 pages.

Knutsson, et al.; "Dentists' Decision on Prophylactic Removal of Mandibular Third Molars: a 10-year Follow-Up Study;" Abstract; 2001; Community Dental and Oral Epidemiology, 29(4):308-14; Malmo University, Sweden; 1 page.

Kunkel, et al.; "Guideline: Surgical Removal of Third Molars;" Medical Guidelines; Apr. 2006; pp. 1-16; ZZQ Agency for Quality in Dentistry, Cologne, Germany; 16 pages.

Kunkel, et al.; "Severe Third Molar Complications Including Death-Lessons from 100 Cases Requiring Hospitalization;" Abstract; 2007; Journal of Oral Maxillofacial Surgery, 65(9):1700-6; Mainz, Germany; 1 page.

Kunkel, et al.; "Third Molar Complications Requiring Hospitalization;" Abstract; Oral Surgery, Oral Medicine, Oral Pathology, Oral Radiology, and Endodontology, 102(3):300-6 (ISSN: 1528-395X); Mainz, Germany; 1 page.

Kusek, K.; "Researchers use light to coax stem cells to repair teeth;" Article; May 28, 2014; pp. 1-6; ©2013 President and Fellows of Harvard College, Harvard School of Engineering and Applied Sciences, Wyss Institute; published online at: http://www.seas.harvard.edu/news/2014/05/researchers-use-light-to-coax-stem-cells-to-repairteeth; Cambridge/Boston, MA, USA; 6 pages.

Langsten, et al.; "The Impact of Retained Third Molars on the Deployed Airman;" Abstract; Jan. 2008; pp. 27-28(2); Military Medicine, vol. 173, Supplement 1; AMSUS, Eglin Air Force Base, FL 32542, USA; 1 page.

Levin, D.; "Nipping Wisdom Teeth in the Bud: Childhood Anesthesia May Thwart the Development of Third Molars;" Article; Fall 2013; ©2014 Tufts University, Tufts Dental Medicine, http://now.tufts.edu/articles/nipping-wisdom-teeth-bud; Boston, MA, USA; 1 page.

Mcardle, et al.; "Distal Cervical Caries in the Mandibular Second Molar: An Indication for the Prophylactic Removal of the Third Molar?;" Abstract; Feb. 2006; British Journal of Oral Maxillofacial Surgery, 44(1):42-5; London, UK; 1 page.

Moss, et al.; "Third Molar Periodontal Pathology and Caries in Senior Adults;" Abstract; 2007; Journal of Oral Maxillofacial Surgery, 65(1):103-8 (ISSN: 0278-2391); Chapel Hill, NC 27599, USA; 2 pages.

Nance, et al.; "Change in Third Molar Angulation and Position in Young Adults and Follow-Up Periodontal Pathology;" Abstract; 2006; Journal of Oral Maxillofacial Surgery, 64(3):424-8; Chapel Hill, NC 27599, USA; 1 page.

National Institutes of Health; "Removal of Third Molars;" Article; Nov. 28-30, 1979; NIH Consensus Statement Online, 2(11):65-8; USA; 5 pages.

Park, et al.; "Cortical Integrity of the Inferior Alveolar Canal as a Predictor of Paresthesia After Third-Molar Extraction;" Article; 2010; Journal of American Dental Association, vol. 141, No. 3, 271-8; USA; 14 pages.

Patent Cooperation Treaty; International Preliminary Report on Patentability of PCT/US10/34259; dated Aug. 31, 2011; 31 pages.

Patent Cooperation Treaty; International Search Report and Written Opinion of PCT/US13/32357; dated Jun. 5, 2013; International Searching Authority; 24 pages.

Patent Cooperation Treaty; "Notification of Transmittal of International Preliminary Report on Patentability," and "International Preliminary Report on Patentability," for PCT/US13/32357; at least as early as May 8, 2015; 14 pages.

Patent Cooperation Treaty; Written Opinion International Search Report, PCT/US10/34259; dated Sep. 14, 2010; 25 pages.

Patent Cooperation Treaty; International Search Report and Written Opinion for PCT/US2020/036508; dated Nov. 17, 2020; 18 pages.

Patent Cooperation Treaty; International Search Report and Written Opinion for PCT/US2020/036705; dated Nov. 17, 2020; 18 pages.

Patent Cooperation Treaty; "International Preliminary Report on Patentability" for PCT/US2020/036508; dated May 18, 2021; 7 pages.

Patent Cooperation Treaty; "International Search Report" and "Written Opinion" for PCT/US2020/057383; dated Jul. 22, 2021; 9 pages.

Pogrel, et al.; "White Paper on Third Molar Data," Article; Mar. 2007; published online by American Association of Oral and Maxillofacial Surgeons at http://www.aaoms.org/docs/third_molar_white_paper.pdf; USA; 25 pages.

Pogrel, M. A.; "What is the Effect of Timing of Removal on the Incidence and Severity of Complications?;" Article; Sep. 2012; pp. S37-S40; Journal of Oral and Maxillofacial Surgery, vol. 70, No. 9, Supplement 1; published online at http://dx.doi.org/10.1016/j.joms.2012.04.028; ©2012 American Association of Oral and Maxillofacial Surgeons; USA; 4 pages.

Pratt, et al.; "Indications for Third Molar Surgery;" Article; Apr. 1998; pp. 105-108 of J. R. Coll. Surg. Edinb, vol. 43; Portsmouth, UK; 7 pages.

Rakprasitkul, S.; "Pathologic Changes in the Pericoronal Tissues of Unerupted Third Molars;" Abstract; 2001; Quintessence International, 32(8):633-8 (ISSN: 0033-6572); Rajthevee, Bangkok, Thailand 10400; 1 page.

Ricketts, et al.; "Third Molar Enucleation: Diagnosis and Technique;" Article; Apr. 1976; pp. 52-57 of Journal—California Dental Association published online at http://www.ncbi.nlm.nih.gov/pubmed/1074850; USA; 6 pages.

Sarnat, et al.; "Developmental Stages of the Third Molar in Israeli Children;" Abstract; 2003; Pediatric Dentistry, 25(4):373-7 (ISSN: 0164-1263); Tel Aviv, Israel; 1 page.

Shugars, et al.; "Incidence of Occlusal Dental Caries in Asymptomatic Third Molars;" Abstract; 2005; Journal of Oral Maxillofacial Surgery, 63(3):341-6 (ISSN: 0278-2391); Chapel Hill, NC 27599, USA; 1 page.

(56) References Cited

OTHER PUBLICATIONS

Silvestri, et al.; "Prevention of Third Molar Development in Dog with Long Pulse Diode Laser: A Preliminary Report;" Report; 2007; Lasers Surg. Med, 39(8):674-7 (ISSN: 0196-8092); Boston, MA 02111, USA; 4 pages.

Silvestri, et al.; "Prevention of Third Molar Development in Dog with Long Pulse Diode Laser: A Preliminary Report;" Introduction; 2007; Lasers Surg. Med, 39(8):674-7 (ISSN: 0196-8092); Boston, MA, USA; 1 page.

Silvestri, et al.; "Prevention of Third Molar Tooth Development in Neonate Rat With a Long Pulse Diode Laser;" Article; 2004; Lasers Surg. Med, 35(5):385-91 (ISSN: 0196-8092); Boston, MA 02111, USA; 7 pages.

Silvestri, et al.; "Prevention of Third Molar Tooth Development in Neonate Rat with a Long Pulse Diode Laser;" Abstract; 2004; Lasers Surg. Med, 35(5):385-91 (ISSN: 0196-8092); Boston, MA, USA; 1 page.

Silvestri, et al.; "Selectively Preventing Development of Third Molars in Rats Using Electrosurgical Energy;" Article; Oct. 2004; pp. 1397-1405 of the Journal of the American Dental Association, vol. 135, No. 10; Boston, MA 02111, USA; 12 pages.

Silvestri, et al.; "The Unresolved Problem of the Third Molar: Would People Be Better Off Without It?;" Article; Apr. 2003; pp. 450-455 of the Journal of the American Dental Association, vol. 134, No. 4; Boston, MA 02111, USA; 11 pages.

Song, et al.; "The Effectiveness and Cost-Effectiveness of Prophylactic Removal of Wisdom Teeth, Executive Summary;" Summary Report; 2000; Health Technology Assessment, vol. 4, No. 15; Southampton, UK; 4 pages.

Swee, et al.; "Inferior alveolar nerve block and third-molar agenesis: a retrospective clinical study;" Article; 2013; published in the Journal of the American Dental Association (JADA), 144(4):389-395; available online at 10.14219/jada.archive.2013.0132; ©2014 American Dental Association; USA; 8 pages.

U.S. Department of Labor; "Dentists;" Webpage; last modified Dec. 17, 2009; 3 pages.

University of York, The; "Prophylactic Removal of Impacted Third Molars: Is It Justified?;" Article; Oct. 1998; Effectiveness Matters, vol. 3, Issue 2; Heslington, York, UK; 4 pages.

Venta, et al.; "Change in Clinical Status of Third Molars in Adults during 12 Years of Observation;" Abstract; 1999; Journal of Oral Maxillofacial Surgery, 5794):386-9 (ISSN: 0278-2391); Helsinki, Finland; 1 page.

Venta, et al.; "Malpractice Claims for Permanent Nerve Injuries Related to Third Molar Removals;" Abstract; 1998; Acta. Odontol. Scand, 56(4):193-6 (ISSN: 0001-6357); Helsinki, Finland; 1 page.

Voegelin, et al.; "Complications during and after Surgical Removal of Mandibular Third Molars. Impact of Patient Related and Anatomical Factors;" Abstract; 2008; Schweiz Monatsschr Zahnmed, 118(3):192-8; Bern, Switzerland; 1 page.

Wealthy Dentist, The; "Dental Marketing: Dentists Refer Some Wisdom Tooth Extractions to Oral Surgeons;" Web article; The Wealthy Dentist.com, at least as early as 2008; Tiburon, CA 94920, USA; 5 pages.

Wikipedia; "Third Molar;" Wikipedia Webpage; last modified Apr. 19, 2011; 9 pages.

Wikipedia; "Tooth Development;" Wikipedia Webpage; last modified Apr. 18, 2011; 16 pages.

X-Nav Technologies; "How It Works: X-Guide Dynamic 3D Navigation Workflow;" Web Article; published online at least as early as 2020 at http://www.x-navtech.com/x-guide/how-it-works; 2 pages.

Brace, Christoper L; "Microwave Ablation With a Triaxial Antenna: Results in ex vivo Bovine Liver"; Author Manuscript of Study Results; National Institute of Health; *IEEE Trans Microw Theory Tech*. Jan. 2005; 53(1):215-220; University of Wisconsin-Madison, Madison, WI, 53706 USA; 21 pages.

Ethicon; "Neuwave™ Microwave Ablation System—Build your ablation program with the only system that has it all"; Brochure No. 068741-170308; Ethicon; 2017; 2 pages.

Ethicon; "Neuwave™ Microwave Ablation System"; Product description; Ethicon; last updated Dec. 15, 2017; published online at: https://www.ethicon.com/na/products/microwave-ablation/microwave-ablation/neuwave-microwave-ablation-system; 5 pages.

Ethicon; "Neuwave™ Microwave Ablation Systems"; Product description; Ethicon; 2021; published online at: https://www.ethicon.com/na/products/microwave-ablation/microwaveablation/neuwave-microwave-ablation-system; 7 pages.

Frenzel, Lou; "What's the Difference Between EM Near Field and Far Field?"; Article; Electronic Design; Jun. 6, 2012; published online at: http://electronicdesign.com/energy/whatsdifferencebetweenemnearfieldandfarfield; 6 pages.

Gordon, Nc et al.; "The effects of local hypothermia on odontogenesis"; Abstract; published in Apr. 1979 Journal of Oral Surgery, 37(4):235-44; 1 page.

ITero, "Text Transcript of OrthoCAD, A Digitally Perfect Orthodontic Impression," www.cadentic.com, ©2009 Cadent, Ltd., 3 pages.

Osensa; "Fiber Optic Temperature Sensors;" Product description; Osensa website; at least as early as May 30, 2020; published online at: www.osensa.com; Burnaby, BC, Canada; 3 pages.

Patent Cooperation Treaty, "International Search Report" for PCT/IL2006/001329, dated Mar. 7, 2007, 6 pages.

Wikipedia; "Near and far field"; Wikipedia entry; page last edited on Sep. 8, 2018; published online at https://en.wikipedia.org/wiki/Near_and_far_field; 11 pages.

AAOMS Task Force; "Summary of the Third Molar Clinical Trials: Report of the AAOMS Task Force for Third Molar Summary;" AAOMS; Journal of Oral and Maxillofacial Surgery; 2012; 70:2238-2248; USA; 11 pages.

Food & Drug Administration (FDA); "Review of Published Literature Between 2008 and 2018 of Relevance to Radiofrequency Radiation and Cancer;" FDA website; Feb. 2020; 113 pages; https://www.fda.gov/media/135043/download.

Henry; "Enucleation of developing mandibular third molar by lateral trepanation;" Article; Proc., Royal Society Medicine 62:837-839; ©1969; Elsevier, United Kingdom; 3 pages; available online at: https://www.ncbi.nlm.nih.gov/pmc/articles/PMC1811173/pdf/procrsmed00306-0105.pdf.

Henry; "Prophylactic Enucleation of Wisdom Tooth Follicles;" Letter to the Editor; Lancet 227:921; ©1936; Elsevier, United Kingdom; 1 page.

Henry; "Prophylactic Odontectomy of the Developing Mandibular Third Molar: A New Operation;" Article; American Journal of Orthodontics and Oral Surgery; vol. 24, Iss. 1, Jan. 1938, pp. 72-84; first page submitted herewith; full 13 page article available online as of Jun. 17, 2004, at: https://www.sciencedirect.com/science/article/abs/pii/S0096634738900033X7via%3Dihub.

Hines-Peralta, et al.; "Microwave Ablation: Results with a 2.45-GHz Applicator in Ex Vivo Bovine and In Vivo Porcine Liver"; Journal of Radiology 239(1):94-102; Abstract; ©2006; 1 page, Oak Brook, Illinois, USA; available at: https://pubmed.ncbi.nlm.nih.gov/16484351/.

Hojjatollah, et al.; "Antenna Designs for Microwave Tissue Ablation;" Author manuscript; PubMed Central; Feb. 27, 2019; Department of Electrical and Computer Engineering, Kansas State University, Manhattan, Kansas, USA; 43 pages.

International Commission on Non-Ionizing Radiation Protection (ICNIRP); "RF EMFS 100kHz-300GHz"; ICNIRP Presentation; 2022; 3 pages; available at: https://www.icnirp.org/en/frequencies/radiofrequency/index.html.

Kaminishi, et al.; "A 10-year Comparative Study of the Incidence of Third Molar Removal in the Aging Population;" Abstract; Journal of Oral Maxillofacial Surgery; 64(2): 173-4 (ISSN: 0278-2391); 2006; Los Angeles, CA, USA; 1 page.

Kim; "Understanding the Nuances of Microwave Ablation for More Accurate Post-Treatment Assessment"; Future Oncology 14(17):1755-1764; ©2018; 10 pages; available at: https://www.futuremedicine.com/doi/full/10.2217/fon-2017-0736?rfr_dat=cr_pub++0pubmed&url_ver=Z39.88-2003&rfr_id=ori%3Arid%3Acrossref.org.

Ling, et al.; "Which Procedure is Better: Germectomy or Surgical Removal of Mandibular Third Molar?"; Int. J. of Oral Maxillofacial Surgery 46:110; Abstract; 2017; 2 pages.

(56) References Cited

OTHER PUBLICATIONS

Lubner et al.; "Microwave Tumor Ablation: Mechanism of Action, Clinical Results, and Devices"; Journal of Vascular and Interventional Radiology 21 (* Suppl.):S192-203; 2010; 28 pages; available at: https://www.ncbi.nlm.nih.gov/pmc/articles/PMC3065977/.

Nanci; "Ten Cate's Oral Histology 7$^{th}$ Edition: Development, Structure, and Function;" Elsevier Mosby; ©2008; St., Louis, MO; 3 pages submitted herewith (including cover, publication page, and table of contents).

Shoshani-Dror, et al.; "Controversy regarding the need for prophylactic removal of impacted third molars: An overview;" Article; Quintessence Verlags-GmbH; © Sep. 2018; vol. 49, No. 8, 653-662; 10 pages; Online publication; document submitted is a personal PDF created for Leigh Colby, Account ID 2617823, created Sep. 2, 2022.

Vranckx, et al; "Prophylactic vs. Symptomatic Third Molar Removal: Effects on Patient Postoperative Morbidity;" Feature Article; the Journal of Evidence-Based Dental Practice; © Sep. 2021; vol. 21, No. 3; 13 pages; SAGE Publishing, Newbury Park, California; available online at https://www.sciencedirect.com/science/article/pii/S1532338221000579?via%3Dihub.

Simo, et al.; "Microwave Ablation Using 915-MHz and 2.45-GHz Systems: What Are the Differences?"; HPB(Oxford); 15(12):991-996; 2013; 13 pages; available at: https://www.hpbonline.org/article/S1365-182X(15)31352-6/fulltext.

\* cited by examiner

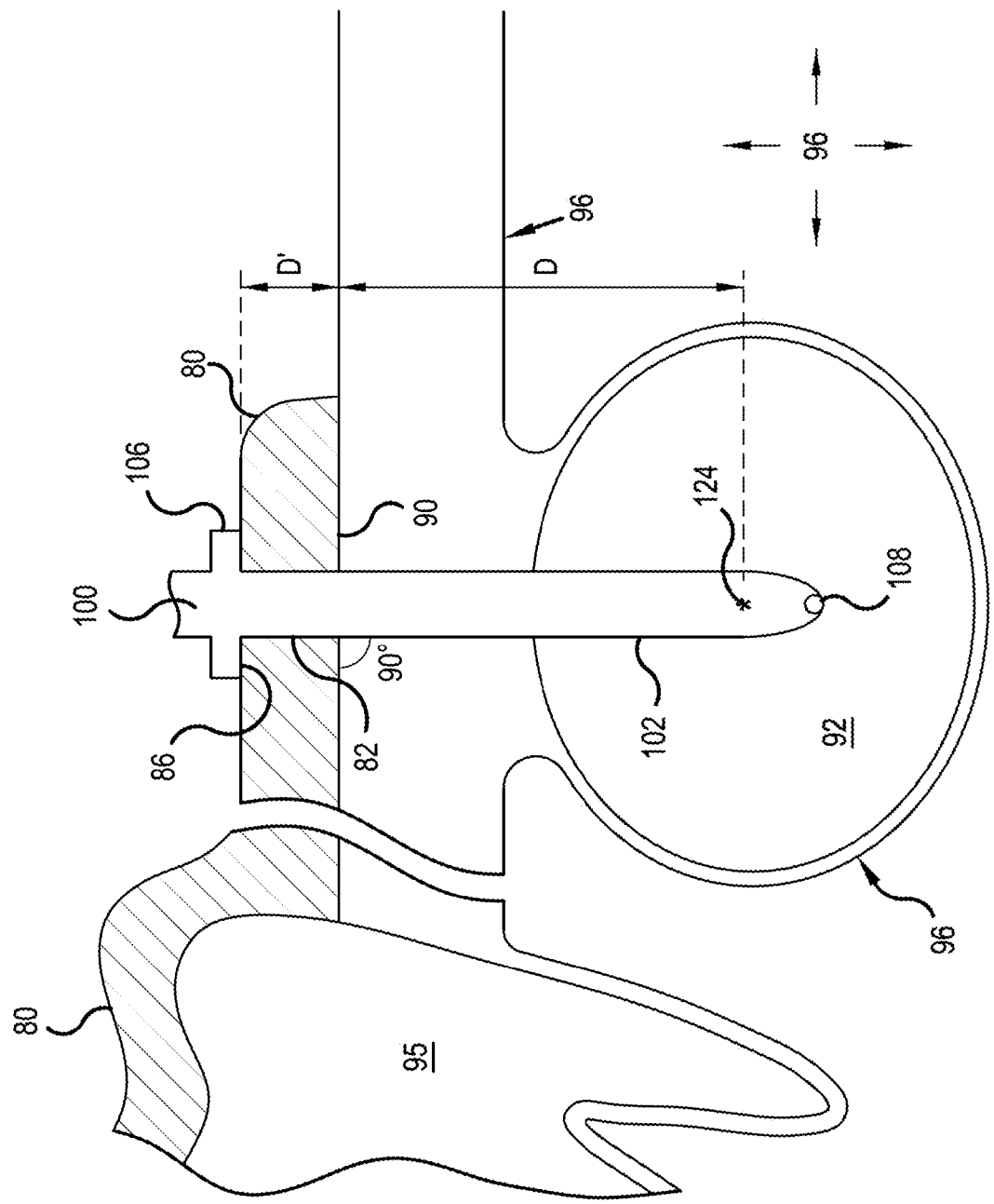

ABLATION PROBE SYSTEMS

The present application is a continuation of Patent Cooperation Treaty (PCT) Application No. PCT/US2020/036705, filed Jun. 8, 2020. PCT Application No. PCT/US2020/036705 claims the benefit of U.S. Provisional Patent Application No. 62/876,574, filed Jul. 19, 2019. PCT Application No. PCT/US2020/036705 claims the benefit of U.S. Provisional Patent Application No. 62/858,230, filed Jun. 6, 2019. The present application is a continuation-in-part of PCT Application No. PCT/US2020/036508, filed on Jun. 5, 2020. PCT Application No. PCT/US2020/036508 claims the benefit of U.S. Provisional Patent Application No. 62/876,574, filed Jul. 19, 2019. PCT Application No. PCT/US2020/036508 claims the benefit of U.S. Provisional Patent Application No. 62/858,230, filed Jun. 6, 2019. The present application is based on and claims priority from these applications, the disclosures of which are hereby expressly incorporated herein by reference in their entirety.

BACKGROUND

The present disclosure describes apparatuses, methods/procedures, and systems that generally relate to the technical field of ablation probes, and specifically relate to the technical field of microwave and radiofrequency ablation probes that have shaped and/or sized target tissue ablation zones that enable guided soft tissue ablation procedures that are more precise and predictable than procedures that are not guided.

The term "ablation" in the medical industry generally describes the removal of problematic (e.g. damaged, diseased, or otherwise undesired) tissue (target tissue) by less invasive techniques that generally employ a probe that operates through the cooling or heating of target tissue, although mechanical, electrical, chemical, and laser ablation technology can also be used. Whereas "resection" involves partially or completely removing an organ by conventional surgical methods (i.e. use of a scalpel or saw to cut out tissue), medical ablation generally involves partially or completely removing or destroying a layer (or layers) of target tissue through a probe that employs thermal or non-thermal technology with the aim of restoring normal function that more selectively destroys the targeted tissue. The goal of ablation is to remove or destroy the target tissue (problematic tissue) with substantially less damage to surrounding tissue or structure compared to more invasive conventional surgical methods. Use of ablation technology can be used to treat a variety of medical conditions ranging from serious to cosmetic. Some of the more common types of ablation include surface ablation (used to remove a layer of target tissue to treat discoloration, improve skin texture, or removing superficial lesions, warts, or tumors), cardiac ablation (such as radiofrequency ablation (RFA) that is used to destroy target tissue in the heart associated with irregular heartbeats), endometrial microwave ablation (used to destroy the lining of the uterus to reduce or stop abnormal bleeding of the uterus), bone marrow ablation (used to remove bone marrow in advance of a bone marrow transplant), and ablative brain surgery (used to treat certain neurological disorders) or microwave ablation (used to treat liver tumors without physically resecting the tumors).

Ablation may be performed using microwaves (e.g. microwave ablation (MWA) and microwave endometrial ablation (MEA)), radiofrequencies (e.g. radiofrequency ablation (RFA)), lasers (e.g. LASIK surgery), ultrasound (e.g. ultra-high intensity ultrasound), chemicals (e.g. chemoablation), low or cold temperatures (e.g. cryoablation), high or hot temperatures, electricity (e.g. fulguration, hot tip or cauterization, and others), and mechanical processes (e.g. rotablation). Microwave ablation is a form of thermal ablation that uses electromagnetic waves in the microwave energy spectrum (300 MHz to 300 GHz) to produce tissue-heating effects to generate tissue necrosis within solid tumors to treat cancer. Microwave endometrial ablation, for example, is one use of microwave ablation which uses microwaves at a fixed frequency to destroy the basal layer of the endometrium and the glands (sparing the remainder of the uterus) by heating them to over 60° C. Another well-established use of microwave ablation is liver tumor ablation, which is commonly performed at 500 MHz to 2.45 GHz. Radiofrequency ablation (RFA) is a medical procedure in which part of the electrical conduction system of the heart, tumor, or other dysfunctional tissue is ablated using the heat generated from medium frequency alternating current (in the range of 300-500 kHz).

One use for ablation is tooth bud ablation. Third molar formation predictably causes lifelong issues including complications, pain, tooth decay, gum disease, and/or abscesses with a rate of nearly 99% over the life of patients. Unfortunately, surgical extraction of fully formed third molars has a host of risks and complications, such as painful post-extraction osteitis or "dry sockets," severe infections, temporary and permanent nerve damage, significant pain, temporary and permanent temporomandibular (TMJ) damage, and more. Historically, there have been suggestions and attempts to prevent the formation of third molars on a prophylactic basis before these problematic teeth completely form—such as those of Dr. Henry in 1969, Drs. Gordon & Laskin in 1978, and more recently by Dr. Silvestri in 2004—to eliminate the disease conditions they predictably cause while eliminating the surgical hazards. However, they have been manual systems that were difficult to implement, inconsistent, unpredictable, un-repeatable because they were manual and—as a result—have never been adopted by dental professionals.

Exemplary systems and methods of guided ablation for tooth bud ablation, such as those described in U.S. Pat. Nos. 9,402,693, 9,827,068, 9,855,112, 10,022,202, 10,265,140, 10,285,778, 10,298,255, 10,299,885, U.S. Patent Publication No. US2011/0200961, U.S. Patent Publication No. US2016/0324597, U.S. Patent Publication No. US2017/0360528, U.S. Patent Publication No. US2018/0091169, U.S. Patent Publication No. US2018/0153640, U.S. Patent Publication No. US2018/0318038, PCT Publication No. WO/2010/132368, PCT Publication No. WO/2014/143014, and related U.S. and foreign patent applications, all of which were invented by the inventor of the present invention and are owned by the applicant of the present application. The disclosures of these references, hereinafter referred to as the "Therapeutic Tooth Bud Ablation Properties" are hereby expressly incorporated by reference. The Therapeutic Tooth Bud Ablation Properties describe tooth bud ablation methods, systems, and procedures that result in tooth agenesis. These methods, systems, and procedures may include and/or use ablation probe tips and/or stents.

The NEUWAVE™ Microwave Ablation System is described as being able to ablate lesions with consistency and control to help protect non-target tissue. The NEUWAVE™ System includes features such as a computer controlled system for storing procedure data and ablation confirmation software to confirm technical success of procedures. It is described as having a burn pattern that controls the ablation distance past the probe tip by limiting the burn pattern past the tip. Even though NEUWAVE asserts that the PR probe "is the only probe available with a unique burn pattern that controls the ablation distance past the probe tip," the NEUWAVE PR microwave ablation probe has serious limitations. The ablation produced by the PR probe encompasses the tip in 10 seconds and then burns "proximally." This means that the burn pattern asymmetrically "creeps" or migrates (which will be referred to generically as "migrates" or variations thereof) up the ablation probe tip (generally away from the absolute tip and toward a handle) with a resulting burn pattern that is so oblong that it is "hot dog" shaped, thus making minimally invasive soft tissue ablation procedures impossible.

Ablation zone migration up the probe tip (generally away from the absolute tip and toward a handle) shaft is a known problem throughout the medical ablation community and numerous attempts have been made to control this problem. For example, U.S. Pat. No. 7,611,508 to Yang et al. sets forth an antenna for microwave tumor ablation that has coaxial antenna conductors surrounded by an insulated sleeve of a length and size promoting destructive interference of axial microwave energy passing inside and outside of the sleeve to limit the tail (which, like "creep," will also be referred to generically as migration or variations thereof) of the burn pattern up the microwave ablation probe tip shaft. Yang's floating sleeve provides destructive wave interference or cancellation of the microwave signal radiating out of the antennas, yet this documentation shows that this technique still results in a zone of ablation that asymmetrically migrates up the probe length during soft tissue ablation with a pattern that is so oblong that it appears to be "hot dog" shaped, thus making minimally invasive soft tissue ablation procedures impossible.

SUMMARY

The present disclosure describes apparatuses, methods/procedures, and systems that generally relate to the technical field of medical ablation probes, and specifically relate to the technical field of microwave ablation probes and radiofrequency ablation probes that deliver shaped and/or sized target tissue ablation zones along with the ability to eliminate migration of the ablation zone (the burn pattern) up the probe tip shaft through a stationary center of ablation while simultaneously controlling power density into the tissue to maximize or minimize peak temperatures in the zone of active heating in the targeted ablation tissue.

A first preferred ablation probe tip has a shaft with an insertion end. The ablation probe tip receives ablation means from an ablation source. The ablation probe tip is for ablating targeted tissue. The ablation probe tip includes the shaft, an annular aperture, a center of ablation, an annular heat transfer layer, and an annular tip cover. The shaft includes a coaxial antenna that, in turn, includes: (i) an inner conductor; (ii) an annular dielectric insulator layer surrounding the inner conductor; and (iii) an annular outer conductor surrounding the annular dielectric insulator layer. The annular aperture is preferably defined in the annular outer conductor toward the insertion end. The center of ablation is preferably located within the inner conductor and surrounded by the annular aperture. The annular heat transfer layer surrounds the coaxial antenna and is preferably spaced from the insertion end such that the annular aperture is preferably between the annular heat transfer layer and the insertion end. The annular tip cover is preferably at the insertion end. The annular tip cover surrounds and covers an end of the coaxial antenna and the annular aperture. The center of ablation is preferably a focal region from which the ablation means radiates through the annular aperture to form an ablation zone. The ablation zone has a predetermined shape selected from the group consisting of oblate, spherical, and oblong.

In one alternative of the first preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the first preferred ablation probe tip, the predetermined shape is preferably determined by an aperture offset. The aperture offset may be a distance between the center of ablation and an annular edge of the annular heat transfer layer. The oblate ablation zone preferably has a relatively short aperture offset. The oblong ablation zone preferably has a relatively long aperture offset. The spherical ablation zone preferably has an aperture offset between the aperture offsets of the oblate ablation zone and the oblong ablation zone.

In one alternative of the first preferred ablation probe tip, the coaxial antenna further includes an insulation annular layer annularly surrounding the coaxial antenna. The annular heat transfer layer annularly surrounds the insulation annular layer.

In one alternative of the first preferred ablation probe tip, the antenna end load is preferably positioned between the annular aperture and the insertion end. The antenna end load preferably concentrates energy density and increases power loading.

In one alternative of the first preferred ablation probe tip, the annular heat transfer layer has high thermal conductivity and is preferably electrically conductive. In one alternative, the annular aperture exposes an annular ring of the annular dielectric insulator layer.

In one alternative of the first preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the first preferred ablation probe tip, the ablation probe tip works in conjunction with a stent. The stent preferably has a surgical guide that guides the ablation probe tip so that the center of ablation is preferably within tissue.

In one alternative of the first preferred ablation probe tip, the center of ablation is preferably a stationary center of ablation in that it does not migrate in relation to the shaft.

In one alternative of the first preferred ablation probe tip, the coaxial antenna is preferably a near field antenna that prevents the center of ablation from migrating up the shaft away from the insertion end. The near field antenna may be a near field reactive antenna.

In one alternative of the first preferred ablation probe tip, the annular heat transfer layer blocks the ablation means from migrating up the shaft away from the insertion end, and the annular heat transfer layer allows thermal energy from the ablation zone to conduct up the shaft away from the insertion end.

In one alternative of the first preferred ablation probe tip, the ablation probe tip is preferably part of an ablation probe system that preferably has at least has at least one peak temperature intra-operative control selected from the group consisting of: (a) passive cooling; (b) active cooling; and (c) a combination of passive and active cooling.

In one alternative of the first preferred ablation probe tip, the annular heat transfer layer is preferably quenched by transferring thermal energy from the annular heat transfer layer into soft tissue surrounding the annular heat transfer layer.

In one alternative of the first preferred ablation probe tip, the ablation probe tip is part of an ablation probe system that has intra-operative control of a volume of the ablation zone. In one alternative, the ablation probe tip is preferably part of an ablation probe system that has intra-operative control of a diameter of the ablation zone.

In one alternative of the first preferred ablation probe tip, the ablation probe tip and the ablation means together allow for at least one intra-operative control selected from the group consisting of: (a) position of the ablation zone; (b) centering of the ablation zone; (c) peak temperature of the ablation zone; (d) volume of the ablation zone; and (e) diameter of the ablation zone.

In one alternative of the first preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation means as the ablation source, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

A second preferred ablation probe tip has a shaft with an insertion end. The ablation probe tip receives ablation means from an ablation source. The ablation probe tip is for ablating targeted tissue. The ablation probe tip includes: the shaft, an annular aperture, a center of ablation, and an annular heat transfer layer. The shaft includes a coaxial antenna. An annular aperture is preferably defined in at least one outer layer of the coaxial antenna toward the insertion end. A center of ablation may be located within the coaxial antenna and surrounded by the annular aperture. The annular heat transfer layer surrounds the coaxial antenna and is preferably spaced from the insertion end such that the annular aperture is preferably between the annular heat transfer layer and the insertion end. The center of ablation may be a focal region from which the ablation means radiates through the annular aperture to form an ablation zone. The ablation zone preferably has a predetermined shape selected from the group consisting of oblate, spherical, and oblong.

In one alternative of the second preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the second preferred ablation probe tip, the coaxial antenna includes: (i) an inner conductor; (ii) an annular dielectric insulator layer surrounding the inner conductor; and (iii) an annular outer conductor surrounding the annular dielectric insulator layer.

In one alternative of the second preferred ablation probe tip, the ablation probe tip includes an annular tip cover at the insertion end. The annular tip cover surrounds and covers an end of the coaxial antenna and the annular aperture.

In one alternative of the second preferred ablation probe tip, the predetermined shape is determined by an aperture offset. The aperture offset may be a distance between the center of ablation and an annular edge of the annular heat transfer layer. An oblate ablation zone may have a relatively short aperture offset. An oblong ablation zone may have a relatively long aperture offset. A spherical ablation zone may have an aperture offset between the aperture offsets of the oblate ablation zone and the oblong ablation zone.

In one alternative of the second preferred ablation probe tip, the coaxial antenna further includes an insulation annular layer annularly surrounding the coaxial antenna. The annular heat transfer layer annularly surrounds the insulation annular layer.

In one alternative of the second preferred ablation probe tip, an antenna end load is positioned between the annular aperture and the insertion end. The antenna end load may concentrate energy density and increase power loading.

In one alternative of the second preferred ablation probe tip, the annular heat transfer layer has high thermal conductivity and is electrically conductive.

In one alternative of the second preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the second preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the second preferred ablation probe tip, the ablation probe tip works in conjunction with a stent. The stent has a surgical guide that guides the ablation probe tip so that the center of ablation is preferably within tissue.

In one alternative of the second preferred ablation probe tip, the center of ablation is preferably a stationary center of ablation in that it does not migrate in relation to the shaft.

In one alternative of the second preferred ablation probe tip, the coaxial antenna is preferably a near field antenna that prevents the center of ablation from migrating up the shaft away from the insertion end. The near field antenna may be a near field reactive antenna.

In one alternative of the second preferred ablation probe tip, the annular heat transfer layer blocks the ablation means from migrating up the shaft away from the insertion end, and the annular heat transfer layer allows thermal energy from the ablation zone to conduct up the shaft away from the insertion end.

In one alternative of the second preferred ablation probe tip, the ablation probe tip is preferably part of an ablation probe system that preferably has at least one peak temperature intra-operative control selected from the group consisting of: (a) passive cooling; (b) active cooling; and (c) a combination of passive and active cooling.

In one alternative of the second preferred ablation probe tip, the annular heat transfer layer is preferably quenched by transferring thermal energy from the annular heat transfer layer into soft tissue surrounding the annular heat transfer layer.

In one alternative of the second preferred ablation probe tip, the ablation probe tip is part of an ablation probe system that preferably has intra-operative control of a volume of the ablation zone. In one alternative, the ablation probe tip is preferably part of an ablation probe system that preferably has intra-operative control of a diameter of the ablation zone.

In one alternative of the second preferred ablation probe tip, the ablation probe tip and the ablation means together allow for at least one intra-operative control selected from the group consisting of: (a) position of the ablation zone; (b) centering of the ablation zone; (c) peak temperature of the ablation zone; (d) volume of the ablation zone; and (e) diameter of the ablation zone.

In one alternative of the second preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation source as the ablation means, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

A third preferred ablation probe tip preferably has a shaft with an insertion end. The ablation probe tip receives ablation means from an ablation source. The ablation probe tip is for ablating targeted tissue. The ablation probe tip includes: the shaft, an annular aperture, a center of ablation, an annular heat transfer layer, and an aperture offset. The shaft includes a coaxial antenna. The annular aperture is preferably defined in at least one outer layer of the coaxial antenna toward the insertion end. The center of ablation is located within the coaxial antenna and surrounded by the annular aperture. The center of ablation is a focal region from which the ablation means radiates through the annular aperture to form an ablation zone. The annular heat transfer layer surrounds the coaxial antenna. The annular heat transfer layer preferably has an annular edge that is preferably the closest part of the annular heat transfer layer to the annular aperture. The annular edge is spaced from the insertion end such that the annular aperture is preferably between the annular heat transfer layer and the insertion end. The aperture offset may be a distance between the center of ablation and the annular edge of the annular heat transfer layer. The ablation zone preferably has a predetermined shape determined by the aperture offset, such that a relatively short length aperture offset causes the ablation zone to be oblate, a relatively long length aperture offset causes the ablation zone to be oblong, and a medium length aperture offset causes the ablation zone to be spherical.

In one alternative of the third preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the third preferred ablation probe tip, the coaxial antenna further includes an insulation annular layer annularly surrounding the coaxial antenna. The annular heat transfer layer annularly surrounds the insulation annular layer.

In one alternative of the third preferred ablation probe tip, an antenna end load is positioned between the annular aperture and the insertion end. The antenna end load may concentrate energy density and increase power loading.

In one alternative of the third preferred ablation probe tip, the annular heat transfer layer preferably has high thermal conductivity and is electrically conductive.

In one alternative of the third preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the third preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the third preferred ablation probe tip, the ablation probe tip works in conjunction with a stent. The stent preferably has a surgical guide that guides the ablation probe tip so that the center of ablation is preferably within tissue.

In one alternative of the third preferred ablation probe tip, the center of ablation is preferably a stationary center of ablation in that it does not migrate in relation to the shaft.

In one alternative of the third preferred ablation probe tip, the coaxial antenna is preferably a near field antenna that prevents the center of ablation from migrating up the shaft away from the insertion end. The near field antenna may be a near field reactive antenna.

In one alternative of the third preferred ablation probe tip, the annular heat transfer layer blocks the ablation means from migrating up the shaft away from the insertion end, and the annular heat transfer layer allows thermal energy from the ablation zone to conduct up the shaft away from the insertion end.

In one alternative of the third preferred ablation probe tip, the ablation probe tip is preferably part of an ablation probe system that preferably has at least one peak temperature intra-operative control selected from the group consisting of: (a) passive cooling; (b) active cooling; and (c) a combination of passive and active cooling.

In one alternative of the third preferred ablation probe tip, the annular heat transfer layer is preferably quenched by transferring thermal energy from the annular heat transfer layer into soft tissue surrounding the annular heat transfer layer.

In one alternative of the third preferred ablation probe tip, the ablation probe tip is part of an ablation probe system that preferably has intra-operative control of a volume of the ablation zone. In one alternative, the ablation probe tip is preferably part of an ablation probe system that preferably has intra-operative control of a diameter of the ablation zone.

In one alternative of the third preferred ablation probe tip, the ablation probe tip and the ablation means together allow for at least one intra-operative control selected from the group consisting of: (a) position of the ablation zone; (b) shaping of the ablation zone; (c) centering of the ablation zone; (d) peak temperature of the ablation zone; (e) volume of the ablation zone; and (f) diameter of the ablation zone.

In one alternative of the third preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation source as the ablation means, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

A fourth preferred ablation probe tip preferably has a shaft with an insertion end. The ablation probe tip receives ablation means from an ablation source. The ablation probe tip is for ablating targeted tissue. The ablation probe tip includes: the shaft, an annular aperture, and a center of ablation. The shaft preferably includes a coaxial antenna that is preferably a near field antenna. The annular aperture is preferably defined in at least one outer layer of the coaxial antenna toward the insertion end. The center of ablation is preferably located within the coaxial antenna and surrounded by the annular aperture. The center of ablation is preferably a focal region from which the ablation means radiates through the annular aperture to form an ablation zone. The near field antenna prevents the center of ablation from migrating up the shaft away from the insertion end.

In one alternative of the fourth preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the fourth preferred ablation probe tip, the ablation probe tip may further include an annular heat transfer layer surrounding the coaxial antenna and spaced from the insertion end such that the annular aperture is preferably between the annular heat transfer layer and the insertion end.

In one alternative of the fourth preferred ablation probe tip, the ablation zone preferably has a predetermined shape selected from the group consisting of oblate, spherical, and oblong.

In one alternative of the fourth preferred ablation probe tip, the ablation probe tip may further include an annular heat transfer layer surrounding the coaxial antenna and spaced from the insertion end such that the annular aperture is preferably between the annular heat transfer layer and the insertion end. The ablation zone preferably has a predetermined shape that is determined by an aperture offset. The aperture offset may be a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

In one alternative of the fourth preferred ablation probe tip, the coaxial antenna further includes an insulation annular layer annularly surrounding the coaxial antenna. The annular heat transfer layer annularly surrounds the insulation annular layer.

In one alternative of the fourth preferred ablation probe tip, an antenna end load is positioned between the annular aperture and the insertion end. The antenna end load may concentrate energy density and increase power loading.

In one alternative of the fourth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably has high thermal conductivity and is electrically conductive.

In one alternative of the fourth preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the fourth preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the fourth preferred ablation probe tip, the ablation probe tip works in conjunction with a stent. The stent preferably has a surgical guide that guides the ablation probe tip so that the center of ablation is preferably within tissue.

In one alternative of the fourth preferred ablation probe tip, the center of ablation is preferably a stationary center of ablation in that it does not migrate in relation to the shaft.

In one alternative of the fourth preferred ablation probe tip, the coaxial antenna is a near field reactive antenna.

In one alternative of the fourth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably blocks the ablation means from migrating up the shaft away from the insertion end. The annular heat transfer layer allows thermal energy from the ablation zone to conduct up the shaft away from the insertion end.

In one alternative of the fourth preferred ablation probe tip, the ablation probe tip is preferably part of an ablation probe system that preferably has at least one peak temperature intra-operative control selected from the group consisting of: (a) passive cooling; (b) active cooling; and (c) a combination of passive and active cooling.

In one alternative of the fourth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer is preferably quenched by transferring thermal energy from the annular heat transfer layer into soft tissue surrounding the annular heat transfer layer.

In one alternative of the fourth preferred ablation probe tip, the ablation probe tip is part of an ablation probe system that preferably has intra-operative control of a volume of the ablation zone. In one alternative, the ablation probe tip is preferably part of an ablation probe system that preferably has intra-operative control of a diameter of the ablation zone.

In one alternative of the fourth preferred ablation probe tip, the ablation probe tip and the ablation means together allow for at least one intra-operative control selected from the group consisting of: (a) position of the ablation zone; (b) shaping of the ablation zone; (c) centering of the ablation zone; (d) peak temperature of the ablation zone; (e) volume of the ablation zone; and (f) diameter of the ablation zone.

In one alternative of the fourth preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation source as the ablation means, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

A fifth preferred ablation probe tip preferably has a shaft with an insertion end. The ablation probe tip receives ablation means from an ablation source. The ablation probe tip is for ablating targeted tissue. The ablation probe tip includes: the shaft, an annular aperture, and a center of ablation. The shaft includes a coaxial antenna that is preferably a near field antenna. The annular aperture is preferably defined in at least one outer layer of the coaxial antenna toward the insertion end. The center of ablation is preferably located within the coaxial antenna and surrounded by the annular aperture. The center of ablation is preferably a focal region from which the ablation means radiates through the annular aperture to form an ablation zone. The near field antenna preferably has a predetermined shape selected from the group consisting of oblate, spherical, and oblong.

In one alternative of the fifth preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the fifth preferred ablation probe tip, the near field antenna prevents the center of ablation from migrating up the shaft away from the insertion end.

In one alternative of the fifth preferred ablation probe tip, the ablation probe tip further includes an annular heat transfer layer surrounding the coaxial antenna.

In one alternative of the fifth preferred ablation probe tip, the ablation probe tip further includes an annular heat transfer layer surrounding the coaxial antenna and spaced from the insertion end such that the annular aperture is preferably between the annular heat transfer layer and the insertion end.

In one alternative of the fifth preferred ablation probe tip, the ablation zone preferably has a predetermined shape selected from the group consisting of oblate, spherical, and oblong.

In one alternative of the fifth preferred ablation probe tip, the ablation probe tip may further include an annular heat transfer layer surrounding the coaxial antenna and spaced from the insertion end such that the annular aperture is preferably between the annular heat transfer layer and the insertion end. The ablation zone preferably has a predetermined shape that is determined by an aperture offset. The aperture offset may be a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

In one alternative of the fifth preferred ablation probe tip, the coaxial antenna further includes an insulation annular layer annularly surrounding the coaxial antenna. The annular heat transfer layer annularly surrounds the insulation annular layer.

In one alternative of the fifth preferred ablation probe tip, an antenna end load is positioned between the annular aperture and the insertion end. The antenna end load may concentrate energy density and increase power loading.

In one alternative of the fifth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably has high thermal conductivity and is electrically conductive.

In one alternative of the fifth preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the fifth preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the fifth preferred ablation probe tip, the ablation probe tip works in conjunction with a stent. The stent preferably has a surgical guide that guides the ablation probe tip so that the center of ablation is preferably within tissue.

In one alternative of the fifth preferred ablation probe tip, the center of ablation is preferably a stationary center of ablation in that it does not migrate in relation to the shaft.

In one alternative of the fifth preferred ablation probe tip, the coaxial antenna being a near field reactive antenna.

In one alternative of the fifth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably blocks the ablation means from migrating up the shaft away from the insertion end. The annular heat transfer layer allows thermal energy from the ablation zone to conduct up the shaft away from the insertion end.

In one alternative of the fifth preferred ablation probe tip, the ablation probe tip is preferably part of an ablation probe system that preferably has at least one peak temperature intra-operative control selected from the group consisting of: (a) passive cooling; (b) active cooling; and (c) a combination of passive and active cooling.

In one alternative of the fifth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer is preferably quenched by transferring thermal energy from the annular heat transfer layer into soft tissue surrounding the annular heat transfer layer.

In one alternative of the fifth preferred ablation probe tip, the ablation probe tip is part of an ablation probe system that preferably has intra-operative control of a volume of the ablation zone. In one alternative, the ablation probe tip is preferably part of an ablation probe system that preferably has intra-operative control of a diameter of the ablation zone.

In one alternative of the fifth preferred ablation probe tip, the ablation probe tip and the ablation means together allow for at least one intra-operative control selected from the group consisting of: (a) position of the ablation zone; (b) shaping of the ablation zone; (c) centering of the ablation zone; (d) peak temperature of the ablation zone; (e) volume of the ablation zone; and (f) diameter of the ablation zone.

In one alternative of the fifth preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation source as the ablation means, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

A sixth preferred ablation probe tip preferably has a shaft with an insertion end. The ablation probe tip receives ablation means from an ablation source. The ablation probe tip is for ablating targeted tissue. The ablation probe tip includes: the shaft, an annular aperture, and a center of ablation. The shaft includes a coaxial antenna that may be a near field antenna. The annular aperture is preferably defined in at least one outer layer of the coaxial antenna toward the insertion end. The center of ablation is located within the coaxial antenna and surrounded by the annular aperture. The center of ablation is preferably a focal region from which the ablation means radiates through the annular aperture to form an ablation zone. The center of ablation is preferably a stationary center of ablation.

In one alternative of the sixth preferred ablation probe tip, the ablation zone is preferably for selectively ablating the targeted tissue while mitigating damage to immediately adjacent collateral tissues. In one alternative, at least some of the targeted tissue can be destroyed by the ablation zone.

In one alternative of the sixth preferred ablation probe tip, the near field antenna prevents the center of ablation from migrating up the shaft away from the insertion end.

In one alternative of the sixth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer prevents the center of ablation from migrating up the shaft away from the insertion end.

In one alternative of the sixth preferred ablation probe tip, the ablation probe tip further includes an annular heat transfer layer surrounding the coaxial antenna.

In one alternative of the sixth preferred ablation probe tip, the ablation probe tip further includes an annular heat transfer layer surrounding the coaxial antenna and spaced from the insertion end such that the annular aperture is preferably between the annular heat transfer layer and the insertion end.

In one alternative of the sixth preferred ablation probe tip, the ablation zone preferably has a predetermined shape selected from the group consisting of oblate, spherical, and oblong.

In one alternative of the sixth preferred ablation probe tip, the ablation probe tip may further include an annular heat transfer layer surrounding the coaxial antenna and spaced from the insertion end such that the annular aperture is preferably between the annular heat transfer layer and the insertion end. The ablation zone preferably has a predetermined shape that is determined by an aperture offset. The aperture offset may be a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

In one alternative of the sixth preferred ablation probe tip, the coaxial antenna further includes an insulation annular layer annularly surrounding the coaxial antenna. The annular heat transfer layer annularly surrounds the insulation annular layer.

In one alternative of the sixth preferred ablation probe tip, an antenna end load is positioned between the annular aperture and the insertion end. The antenna end load may concentrate energy density and increase power loading.

In one alternative of the sixth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably has high thermal conductivity and is electrically conductive.

In one alternative of the sixth preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the sixth preferred ablation probe tip, the ablation probe tip may be part of a surgical ablation kit that includes an ablation source, a hand piece, a stent, and a prescription. The prescription may include at least one setting or parameter selected from the group consisting of: (a) ablation energy dose tolerances; (b) levels of energy; and (c) duration of energy deliverance.

In one alternative of the sixth preferred ablation probe tip, the ablation probe tip works in conjunction with a stent. The stent preferably has a surgical guide that guides the ablation probe tip so that the center of ablation is preferably within tissue.

In one alternative of the sixth preferred ablation probe tip, the coaxial antenna being a near field reactive antenna.

In one alternative of the sixth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer preferably blocks the ablation means from migrating up the shaft away from the insertion end. The annular heat transfer layer allows thermal energy from the ablation zone to conduct up the shaft away from the insertion end.

In one alternative of the sixth preferred ablation probe tip, the ablation probe tip is preferably part of an ablation probe system that preferably has at least one peak temperature intra-operative control selected from the group consisting of: (a) passive cooling; (b) active cooling; and (c) a combination of passive and active cooling.

In one alternative of the sixth preferred ablation probe tip, the ablation probe tip further includes an annular heat transfer layer surrounding the coaxial antenna and spaced from the insertion end such that the annular aperture is preferably between the annular heat transfer layer and the insertion end. The annular heat transfer layer is preferably quenched by transferring thermal energy from the annular heat transfer layer into soft tissue surrounding the annular heat transfer layer.

In one alternative of the sixth preferred ablation probe tip, the ablation probe tip is part of an ablation probe system that preferably has intra-operative control of a volume of the ablation zone. In one alternative, the ablation probe tip is preferably part of an ablation probe system that preferably has intra-operative control of a diameter of the ablation zone.

In one alternative of the sixth preferred ablation probe tip, the ablation probe tip and the ablation means together allow for at least one intra-operative control selected from the group consisting of: (a) position of the ablation zone; (b) shaping of the ablation zone; (c) centering of the ablation zone; (d) peak temperature of the ablation zone; (e) volume of the ablation zone; and (f) diameter of the ablation zone.

In one alternative of the sixth preferred ablation probe tip, the ablation probe tip is preferably a micro-ablation ablation probe tip. In one alternative, the ablation probe tip is preferably a microwave ablation probe tip. The microwave ablation probe tip may receive microwave energy from the ablation source as the ablation means, and the microwave energy may be delivered to the target tissue via the ablation probe tip. The ablation source may provide microwave energy at frequencies ranging from 500 MHz to 20 GHz. On the other hand, in one alternative, the ablation probe tip may be a radiofrequency ablation probe tip.

The present disclosure describes apparatuses, methods/procedures, and systems that generally relate to the technical field of medical ablation probes, and specifically relate to the technical field of microwave ablation probes and radiofrequency ablation probes that deliver shaped and/or sized target tissue ablation zones along with the ability to eliminate migration of the ablation zone (the burn pattern) up the probe tip shaft through a stationary center of ablation while simultaneously controlling power loading (power density) into the tissue to maximize or minimize peak temperatures in the active heating zone in the targeted ablation tissue.

A first preferred ablation probe tip preferably has a shaft with an insertion end. The ablation probe tip preferably receives ablation means from an ablation source. The ablation probe tip is preferably for ablating targeted tissue. The ablation probe tip preferably includes: the shaft, an annular aperture, and a center of ablation. The shaft preferably includes a coaxial antenna. The annular aperture is preferably defined in at least one outer layer of the coaxial antenna toward the insertion end. The center of ablation is preferably located within the coaxial antenna and surrounded by the annular aperture. The center of ablation can be considered a focal region from which the ablation means radiates through the annular aperture to form an ablation zone. The ablation zone preferably has a predetermined power loading density in the ablation zone.

In one alternative of the first preferred ablation probe tip, the ablation zone is for selectively ablating the targeted tissue while mitigating damage to immediately adjacent collateral tissues. In one alternative of the first preferred ablation probe tip, at least some of the targeted tissue is destroyed by the ablation zone.

In one alternative of the first preferred ablation probe tip, the annular aperture is preferably a short annular aperture that preferably creates a short active heating zone surrounding the annular aperture. The short active heating zone preferably creates high power loading in the ablation zone. The short active heating zone preferably creates high peak temperatures in the ablation zone.

In one alternative of the first preferred ablation probe tip, the annular aperture is preferably a medium annular aperture that preferably creates a medium active heating zone surrounding the annular aperture. The medium active heating zone preferably creates medium power loading in the ablation zone. The medium active heating zone preferably creates medium peak temperatures in the ablation zone.

In one alternative of the first preferred ablation probe tip, the annular aperture is preferably a long annular aperture that preferably creates a long active heating zone surrounding the annular aperture. The long active heating zone preferably creates low power loading in the ablation zone. The long active heating zone preferably creates low peak temperatures in the ablation zone.

In one alternative of the first preferred ablation probe tip, the coaxial antenna is preferably a near field antenna. The center of ablation is preferably a stationary center of ablation. The near field antenna preferably prevents the center of ablation from migrating up the shaft away from the insertion end.

One alternative of the first preferred ablation probe tip further includes an annular heat transfer layer surrounding the coaxial antenna. The annular heat transfer layer may surround the coaxial antenna and be spaced from the insertion end such that the annular aperture is between the annular heat transfer layer and the insertion end. The annular heat transfer layer preferably prevents the center of ablation from migrating up the shaft away from the insertion end.

In one alternative of the first preferred ablation probe tip, the ablation zone preferably has a predetermined shape selected from the group consisting of oblate, spherical, and oblong.

One alternative of the first preferred ablation probe tip further includes an annular heat transfer layer surrounding the coaxial antenna and spaced from the insertion end such that the annular aperture is between the annular heat transfer layer and the insertion end. The ablation zone preferably has a predetermined shape that is determined by an aperture offset. The aperture offset is preferably a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

One alternative of the first preferred ablation probe tip further includes an annular heat transfer layer that surrounds the coaxial antenna. The coaxial antenna further includes an insulation annular layer annularly surrounding the coaxial antenna. The annular heat transfer layer preferably annularly surrounds the insulation annular layer.

In one alternative of the first preferred ablation probe tip, an antenna end load is preferably positioned between the annular aperture and the insertion end. The antenna end load may concentrate energy density and increase power loading.

One alternative of the first preferred ablation probe tip further includes an annular heat transfer layer surrounding the coaxial antenna and spaced from the insertion end such that the annular aperture is between the annular heat transfer layer and the insertion end. The annular heat transfer layer preferably has high thermal conductivity and is preferably electrically conductive.

In one alternative of the first preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the first preferred ablation probe tip, the ablation probe tip is preferably part of a surgical ablation kit that includes an ablation source, a hand piece, a stent, and a prescription. The prescription preferably includes at least one setting or parameter selected from the group consisting of: ablation energy dose tolerances, levels of energy, and duration of energy deliverance.

In one alternative of the first preferred ablation probe tip, the ablation probe tip preferably works in conjunction with a stent. The stent preferably has a surgical guide. The surgical guide is preferably for guiding the ablation probe tip so that the center of ablation is within tissue.

In one alternative of the first preferred ablation probe tip, the coaxial antenna is preferably a near field reactive antenna.

One alternative of the first preferred ablation probe tip further includes an annular heat transfer layer surrounding the coaxial antenna and spaced from the insertion end such that the annular aperture is between the annular heat transfer layer and the insertion end. Preferably, the annular heat transfer layer blocks the ablation means from migrating up the shaft away from the insertion end. Preferably, the annular heat transfer layer allows thermal energy from the ablation zone to conduct up the shaft away from the insertion end.

In one alternative of the first preferred ablation probe tip, the ablation probe tip is preferably part of an ablation probe system that preferably has peak temperature intra-operative control selected from the group consisting of: passive cooling, active cooling, and a combination of passive and active cooling.

One alternative of the first preferred ablation probe tip further includes an annular heat transfer layer surrounding the coaxial antenna and spaced from the insertion end such that the annular aperture is between the annular heat transfer layer and the insertion end. The annular heat transfer layer is preferably quenched by transferring thermal energy from the annular heat transfer layer into soft tissue surrounding the annular heat transfer layer.

In one alternative of the first preferred ablation probe tip, the ablation probe tip is preferably part of an ablation probe system that preferably has intra-operative control of a volume of the ablation zone. In one alternative of the first preferred ablation probe tip, the ablation probe tip is preferably part of an ablation probe system that preferably has intra-operative control of a diameter of the ablation zone.

In one alternative of the first preferred ablation probe tip, the ablation probe tip and the ablation means together allow for at least one intra-operative control selected from the group consisting of: position of the ablation zone, shaping of the ablation zone, centering of the ablation zone, peak temperature of the ablation zone, volume of the ablation zone, and diameter of the ablation zone.

In one alternative of the first preferred ablation probe tip, the ablation probe tip is preferably a micro-ablation ablation probe tip.

In one alternative of the first preferred ablation probe tip, the ablation probe tip is preferably a microwave ablation probe tip. The microwave ablation probe tip may receive microwave energy from the ablation source as the ablation means. The microwave energy may be delivered to the target tissue via the ablation probe tip. The ablation source may provide microwave energy at frequencies ranging from 500 MHz to 20 GHz.

In one alternative of the first preferred ablation probe tip, the ablation probe tip is preferably a radiofrequency ablation probe tip.

A second preferred ablation probe tip preferably has a shaft with an insertion end. The ablation probe tip preferably receives ablation means from an ablation source. The ablation probe tip is preferably for ablating targeted tissue. The ablation probe tip preferably includes: the shaft, an annular aperture, and a center of ablation. The shaft preferably includes a coaxial antenna. The annular aperture is preferably defined in at least one outer layer of the coaxial antenna toward the insertion end. The center of ablation is preferably located within the coaxial antenna and surrounded by the annular aperture. The center of ablation can be considered a focal region from which the ablation means radiates through the annular aperture to form an ablation zone. The ablation zone preferably has a predetermined peak temperature in the ablation zone.

In one alternative of the second preferred ablation probe tip, the ablation zone is for selectively ablating the targeted tissue while mitigating damage to immediately adjacent collateral tissues. In one alternative of the second preferred ablation probe tip, at least some of the targeted tissue is destroyed by the ablation zone.

In one alternative of the second preferred ablation probe tip, the annular aperture is preferably a short annular aperture that preferably creates a short active heating zone surrounding the annular aperture. The short active heating zone preferably creates high power loading in the ablation zone. The short active heating zone preferably creates high peak temperatures in the ablation zone.

In one alternative of the second preferred ablation probe tip, the annular aperture is preferably a medium annular aperture that preferably creates a medium active heating zone surrounding the annular aperture. The medium active heating zone preferably creates medium power loading in the ablation zone. The medium active heating zone preferably creates medium peak temperatures in the ablation zone.

In one alternative of the second preferred ablation probe tip, the annular aperture is preferably a long annular aperture that preferably creates a long active heating zone surrounding the annular aperture. The long active heating zone preferably creates low power loading in the ablation zone. The long active heating zone preferably creates low peak temperatures in the ablation zone.

In one alternative of the second preferred ablation probe tip, the coaxial antenna is preferably a near field antenna. The center of ablation is preferably a stationary center of ablation. The near field antenna preferably prevents the center of ablation from migrating up the shaft away from the insertion end.

One alternative of the second preferred ablation probe tip further includes an annular heat transfer layer surrounding the coaxial antenna. The annular heat transfer layer may surround the coaxial antenna and be spaced from the insertion end such that the annular aperture is between the annular heat transfer layer and the insertion end. The annular heat transfer layer preferably prevents the center of ablation from migrating up the shaft away from the insertion end.

In one alternative of the second preferred ablation probe tip, the ablation zone preferably has a predetermined shape selected from the group consisting of oblate, spherical, and oblong.

One alternative of the second preferred ablation probe tip further includes an annular heat transfer layer surrounding the coaxial antenna and spaced from the insertion end such that the annular aperture is between the annular heat transfer layer and the insertion end. The ablation zone preferably has a predetermined shape that is determined by an aperture offset. The aperture offset is preferably a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

One alternative of the second preferred ablation probe tip further includes an annular heat transfer layer that surrounds the coaxial antenna. The coaxial antenna further includes an insulation annular layer annularly surrounding the coaxial antenna. The annular heat transfer layer preferably annularly surrounds the insulation annular layer.

In one alternative of the second preferred ablation probe tip, an antenna end load is preferably positioned between the annular aperture and the insertion end. The antenna end load may concentrate energy density and increase power loading.

One alternative of the second preferred ablation probe tip further includes an annular heat transfer layer surrounding the coaxial antenna and spaced from the insertion end such that the annular aperture is between the annular heat transfer layer and the insertion end. The annular heat transfer layer preferably has high thermal conductivity and is preferably electrically conductive.

In one alternative of the second preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the second preferred ablation probe tip, the ablation probe tip is preferably part of a surgical ablation kit that includes an ablation source, a hand piece, a stent, and a prescription. The prescription preferably includes at least one setting or parameter selected from the group consisting of: ablation energy dose tolerances, levels of energy, and duration of energy deliverance.

In one alternative of the second preferred ablation probe tip, the ablation probe tip preferably works in conjunction with a stent. The stent preferably has a surgical guide. The surgical guide is preferably for guiding the ablation probe tip so that the center of ablation is within tissue.

In one alternative of the second preferred ablation probe tip, the coaxial antenna is preferably a near field reactive antenna.

One alternative of the second preferred ablation probe tip further includes an annular heat transfer layer surrounding the coaxial antenna and spaced from the insertion end such that the annular aperture is between the annular heat transfer layer and the insertion end. Preferably, the annular heat transfer layer blocks the ablation means from migrating up the shaft away from the insertion end. Preferably, the annular heat transfer layer allows thermal energy from the ablation zone to conduct up the shaft away from the insertion end.

In one alternative of the second preferred ablation probe tip, the ablation probe tip is preferably part of an ablation probe system that preferably has peak temperature intra-operative control selected from the group consisting of: passive cooling, active cooling, and a combination of passive and active cooling.

One alternative of the second preferred ablation probe tip further includes an annular heat transfer layer surrounding the coaxial antenna and spaced from the insertion end such that the annular aperture is between the annular heat transfer layer and the insertion end. The annular heat transfer layer is preferably quenched by transferring thermal energy from the annular heat transfer layer into soft tissue surrounding the annular heat transfer layer.

In one alternative of the second preferred ablation probe tip, the ablation probe tip is preferably part of an ablation probe system that preferably has intra-operative control of a volume of the ablation zone. In one alternative of the second preferred ablation probe tip, the ablation probe tip is preferably part of an ablation probe system that preferably has intra-operative control of a diameter of the ablation zone.

In one alternative of the second preferred ablation probe tip, the ablation probe tip and the ablation means together allow for at least one intra-operative control selected from the group consisting of: position of the ablation zone, shaping of the ablation zone, centering of the ablation zone, peak temperature of the ablation zone, volume of the ablation zone, and diameter of the ablation zone.

In one alternative of the second preferred ablation probe tip, the ablation probe tip is preferably a micro-ablation ablation probe tip.

In one alternative of the second preferred ablation probe tip, the ablation probe tip is preferably a microwave ablation probe tip. The microwave ablation probe tip may receive microwave energy from the ablation source as the ablation means. The microwave energy may be delivered to the target tissue via the ablation probe tip. The ablation source may provide microwave energy at frequencies ranging from 500 MHz to 20 GHz.

In one alternative of the second preferred ablation probe tip, the ablation probe tip is preferably a radiofrequency ablation probe tip.

A third preferred ablation probe tip preferably has a shaft with an insertion end. The ablation probe tip preferably receives ablation means from an ablation source. The ablation probe tip is preferably for ablating targeted tissue. The ablation probe tip preferably includes: the shaft, an annular aperture, and a center of ablation. The shaft preferably includes a coaxial antenna. The annular aperture is preferably defined in at least one outer layer of the coaxial antenna toward the insertion end. The center of ablation is preferably located within the coaxial antenna and surrounded by the annular aperture. The center of ablation can be considered a focal region from which the ablation means radiates through the annular aperture to form an ablation zone. The ablation zone preferably has an annular aperture and a power loading density in the ablation zone, the annular aperture and the power loading density being selected from the group consisting of: (a) a short annular aperture and high power loading; (b) a medium annular aperture and medium power loading; and (c) a long annular aperture and low power loading.

In one alternative of the third preferred ablation probe tip, the ablation zone is for selectively ablating the targeted tissue while mitigating damage to immediately adjacent collateral tissues. In one alternative of the third preferred ablation probe tip, at least some of the targeted tissue is destroyed by the ablation zone.

In one alternative of the third preferred ablation probe tip, the ablation zone preferably has a peak temperature in the ablation zone selected from the group consisting of: (a) if the annular aperture is a short annular aperture, the peak temperature in the ablation zone is a high peak temperature; (b) if the annular aperture is a medium annular aperture, the peak temperature in the ablation zone is a medium peak temperature; and (c) if the annular aperture is a long annular aperture, the peak temperature in the ablation zone is a low peak temperature.

In one alternative of the third preferred ablation probe tip, the coaxial antenna is preferably a near field antenna. The center of ablation is preferably a stationary center of ablation. The near field antenna preferably prevents the center of ablation from migrating up the shaft away from the insertion end.

One alternative of the third preferred ablation probe tip further includes an annular heat transfer layer surrounding the coaxial antenna. The annular heat transfer layer may surround the coaxial antenna and be spaced from the insertion end such that the annular aperture is between the annular heat transfer layer and the insertion end. The annular heat transfer layer preferably prevents the center of ablation from migrating up the shaft away from the insertion end.

In one alternative of the third preferred ablation probe tip, the ablation zone preferably has a predetermined shape selected from the group consisting of oblate, spherical, and oblong.

One alternative of the third preferred ablation probe tip further includes an annular heat transfer layer surrounding the coaxial antenna and spaced from the insertion end such that the annular aperture is between the annular heat transfer layer and the insertion end. The ablation zone preferably has a predetermined shape that is determined by an aperture offset. The aperture offset is preferably a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

One alternative of the third preferred ablation probe tip further includes an annular heat transfer layer that surrounds the coaxial antenna. The coaxial antenna further includes an insulation annular layer annularly surrounding the coaxial antenna. The annular heat transfer layer preferably annularly surrounds the insulation annular layer.

In one alternative of the third preferred ablation probe tip, an antenna end load is preferably positioned between the annular aperture and the insertion end. The antenna end load may concentrate energy density and increase power loading.

One alternative of the third preferred ablation probe tip further includes an annular heat transfer layer surrounding the coaxial antenna and spaced from the insertion end such that the annular aperture is between the annular heat transfer layer and the insertion end. The annular heat transfer layer preferably has high thermal conductivity and is preferably electrically conductive.

In one alternative of the third preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the third preferred ablation probe tip, the ablation probe tip is preferably part of a surgical ablation kit that includes an ablation source, a hand piece, a stent, and a prescription. The prescription preferably includes at least one setting or parameter selected from the group consisting of: ablation energy dose tolerances, levels of energy, and duration of energy deliverance.

In one alternative of the third preferred ablation probe tip, the ablation probe tip preferably works in conjunction with a stent. The stent preferably has a surgical guide. The surgical guide is preferably for guiding the ablation probe tip so that the center of ablation is within tissue.

In one alternative of the third preferred ablation probe tip, the coaxial antenna is preferably a near field reactive antenna.

One alternative of the third preferred ablation probe tip further includes an annular heat transfer layer surrounding the coaxial antenna and spaced from the insertion end such that the annular aperture is between the annular heat transfer layer and the insertion end. Preferably, the annular heat transfer layer blocks the ablation means from migrating up the shaft away from the insertion end. Preferably, the annular heat transfer layer allows thermal energy from the ablation zone to conduct up the shaft away from the insertion end.

In one alternative of the third preferred ablation probe tip, the ablation probe tip is preferably part of an ablation probe system that preferably has peak temperature intra-operative control selected from the group consisting of: passive cooling, active cooling, and a combination of passive and active cooling.

One alternative of the third preferred ablation probe tip further includes an annular heat transfer layer surrounding the coaxial antenna and spaced from the insertion end such that the annular aperture is between the annular heat transfer layer and the insertion end. The annular heat transfer layer is preferably quenched by transferring thermal energy from the annular heat transfer layer into soft tissue surrounding the annular heat transfer layer.

In one alternative of the third preferred ablation probe tip, the ablation probe tip is preferably part of an ablation probe system that preferably has intra-operative control of a volume of the ablation zone. In one alternative of the third preferred ablation probe tip, the ablation probe tip is preferably part of an ablation probe system that preferably has intra-operative control of a diameter of the ablation zone.

In one alternative of the third preferred ablation probe tip, the ablation probe tip and the ablation means together allow for at least one intra-operative control selected from the group consisting of: position of the ablation zone, shaping of the ablation zone, centering of the ablation zone, peak temperature of the ablation zone, volume of the ablation zone, and diameter of the ablation zone.

In one alternative of the third preferred ablation probe tip, the ablation probe tip is preferably a micro-ablation ablation probe tip.

In one alternative of the third preferred ablation probe tip, the ablation probe tip is preferably a microwave ablation probe tip. The microwave ablation probe tip may receive microwave energy from the ablation source as the ablation means. The microwave energy may be delivered to the target tissue via the ablation probe tip. The ablation source may provide microwave energy at frequencies ranging from 500 MHz to 20 GHz.

In one alternative of the third preferred ablation probe tip, the ablation probe tip is preferably a radiofrequency ablation probe tip.

A fourth preferred ablation probe tip preferably has a shaft with an insertion end. The ablation probe tip preferably receives ablation means from an ablation source. The ablation probe tip is preferably for ablating targeted tissue. The ablation probe tip preferably includes: the shaft, an annular aperture, and a center of ablation. The shaft preferably includes a coaxial antenna. The annular aperture is preferably defined in at least one outer layer of the coaxial antenna toward the insertion end. The center of ablation is preferably located within the coaxial antenna and surrounded by the annular aperture. The center of ablation can be considered a focal region from which the ablation means radiates through the annular aperture to form an ablation zone. The ablation zone preferably has an annular aperture and a peak temperature in the ablation zone, the annular aperture and the peak temperature selected from the group consisting of: (i) a short annular aperture and high peak temperature; (ii) a medium annular aperture and medium peak temperature; and (iii) a long annular aperture and low peak temperature.

In one alternative of the fourth preferred ablation probe tip, the ablation zone is for selectively ablating the targeted tissue while mitigating damage to immediately adjacent collateral tissues. In one alternative of the fourth preferred ablation probe tip, at least some of the targeted tissue is destroyed by the ablation zone.

In one alternative of the fourth preferred ablation probe tip, the coaxial antenna is preferably a near field antenna. The center of ablation is preferably a stationary center of ablation. The near field antenna preferably prevents the center of ablation from migrating up the shaft away from the insertion end.

One alternative of the fourth preferred ablation probe tip further includes an annular heat transfer layer surrounding the coaxial antenna. The annular heat transfer layer may surround the coaxial antenna and be spaced from the insertion end such that the annular aperture is between the annular heat transfer layer and the insertion end. The annular heat transfer layer preferably prevents the center of ablation from migrating up the shaft away from the insertion end.

In one alternative of the fourth preferred ablation probe tip, the ablation zone preferably has a predetermined shape selected from the group consisting of oblate, spherical, and oblong.

One alternative of the fourth preferred ablation probe tip further includes an annular heat transfer layer surrounding the coaxial antenna and spaced from the insertion end such that the annular aperture is between the annular heat transfer layer and the insertion end. The ablation zone preferably has a predetermined shape that is determined by an aperture offset. The aperture offset is preferably a distance between the center of ablation and an annular edge of the annular heat transfer layer. An oblate ablation zone preferably has a relatively short aperture offset. An oblong ablation zone preferably has a relatively long aperture offset. A spherical ablation zone preferably has an aperture offset between the aperture offsets of the oblate ablation zone and the oblong ablation zone.

One alternative of the fourth preferred ablation probe tip further includes an annular heat transfer layer that surrounds the coaxial antenna. The coaxial antenna further includes an insulation annular layer annularly surrounding the coaxial antenna. The annular heat transfer layer preferably annularly surrounds the insulation annular layer.

In one alternative of the fourth preferred ablation probe tip, an antenna end load is preferably positioned between the annular aperture and the insertion end. The antenna end load may concentrate energy density and increase power loading.

One alternative of the fourth preferred ablation probe tip further includes an annular heat transfer layer surrounding the coaxial antenna and spaced from the insertion end such that the annular aperture is between the annular heat transfer layer and the insertion end. The annular heat transfer layer preferably has high thermal conductivity and is preferably electrically conductive.

In one alternative of the fourth preferred ablation probe tip, the coaxial antenna includes an inner conductor, an annular dielectric insulator layer surrounding the inner conductor, and an annular outer conductor surrounding the annular dielectric insulator layer. The annular aperture exposes an annular ring of the annular dielectric insulator layer.

In one alternative of the fourth preferred ablation probe tip, the ablation probe tip is preferably part of a surgical ablation kit that includes an ablation source, a hand piece, a stent, and a prescription. The prescription preferably includes at least one setting or parameter selected from the group consisting of: ablation energy dose tolerances, levels of energy, and duration of energy deliverance.

In one alternative of the fourth preferred ablation probe tip, the ablation probe tip preferably works in conjunction with a stent. The stent preferably has a surgical guide. The surgical guide is preferably for guiding the ablation probe tip so that the center of ablation is within tissue.

In one alternative of the fourth preferred ablation probe tip, the coaxial antenna is preferably a near field reactive antenna.

One alternative of the fourth preferred ablation probe tip further includes an annular heat transfer layer surrounding the coaxial antenna and spaced from the insertion end such that the annular aperture is between the annular heat transfer layer and the insertion end. Preferably, the annular heat transfer layer blocks the ablation means from migrating up the shaft away from the insertion end. Preferably, the annular heat transfer layer allows thermal energy from the ablation zone to conduct up the shaft away from the insertion end.

In one alternative of the fourth preferred ablation probe tip, the ablation probe tip is preferably part of an ablation probe system that preferably has peak temperature intra-operative control selected from the group consisting of: passive cooling, active cooling, and a combination of passive and active cooling.

One alternative of the fourth preferred ablation probe tip further includes an annular heat transfer layer surrounding the coaxial antenna and spaced from the insertion end such that the annular aperture is between the annular heat transfer layer and the insertion end. The annular heat transfer layer is preferably quenched by transferring thermal energy from the annular heat transfer layer into soft tissue surrounding the annular heat transfer layer.

In one alternative of the fourth preferred ablation probe tip, the ablation probe tip is preferably part of an ablation probe system that preferably has intra-operative control of a volume of the ablation zone. In one alternative of the fourth preferred ablation probe tip, the ablation probe tip is preferably part of an ablation probe system that preferably has intra-operative control of a diameter of the ablation zone.

In one alternative of the fourth preferred ablation probe tip, the ablation probe tip and the ablation means together allow for at least one intra-operative control selected from the group consisting of: position of the ablation zone, shaping of the ablation zone, centering of the ablation zone, peak temperature of the ablation zone, volume of the ablation zone, and diameter of the ablation zone.

In one alternative of the fourth preferred ablation probe tip, the ablation probe tip is preferably a micro-ablation ablation probe tip.

In one alternative of the fourth preferred ablation probe tip, the ablation probe tip is preferably a microwave ablation probe tip. The microwave ablation probe tip may receive microwave energy from the ablation source as the ablation means. The microwave energy may be delivered to the target tissue via the ablation probe tip. The ablation source may provide microwave energy at frequencies ranging from 500 MHz to 20 GHz.

In one alternative of the fourth preferred ablation probe tip, the ablation probe tip is preferably a radiofrequency ablation probe tip.

Objectives, features, combinations, and advantages described and implied herein will be more readily understood upon consideration of the following detailed description of the invention, taken in conjunction with the accompanying drawings. The subject matter described herein is also particularly pointed out and distinctly claimed in the concluding portion of this specification.

DESCRIPTION OF THE DRAWINGS

The accompanying drawings illustrate various exemplary ablation probe systems, components of various exemplary ablation probe systems, and/or provide teachings by which the various exemplary ablation probe systems are more readily understood.

FIG. 2 is a simplified cross-sectional view of an exemplary soft tissue ablation site within an oral cavity, the ablation probe tip positioned by the stent such that the center of ablation is within the soft tissue.

Figure 1A:
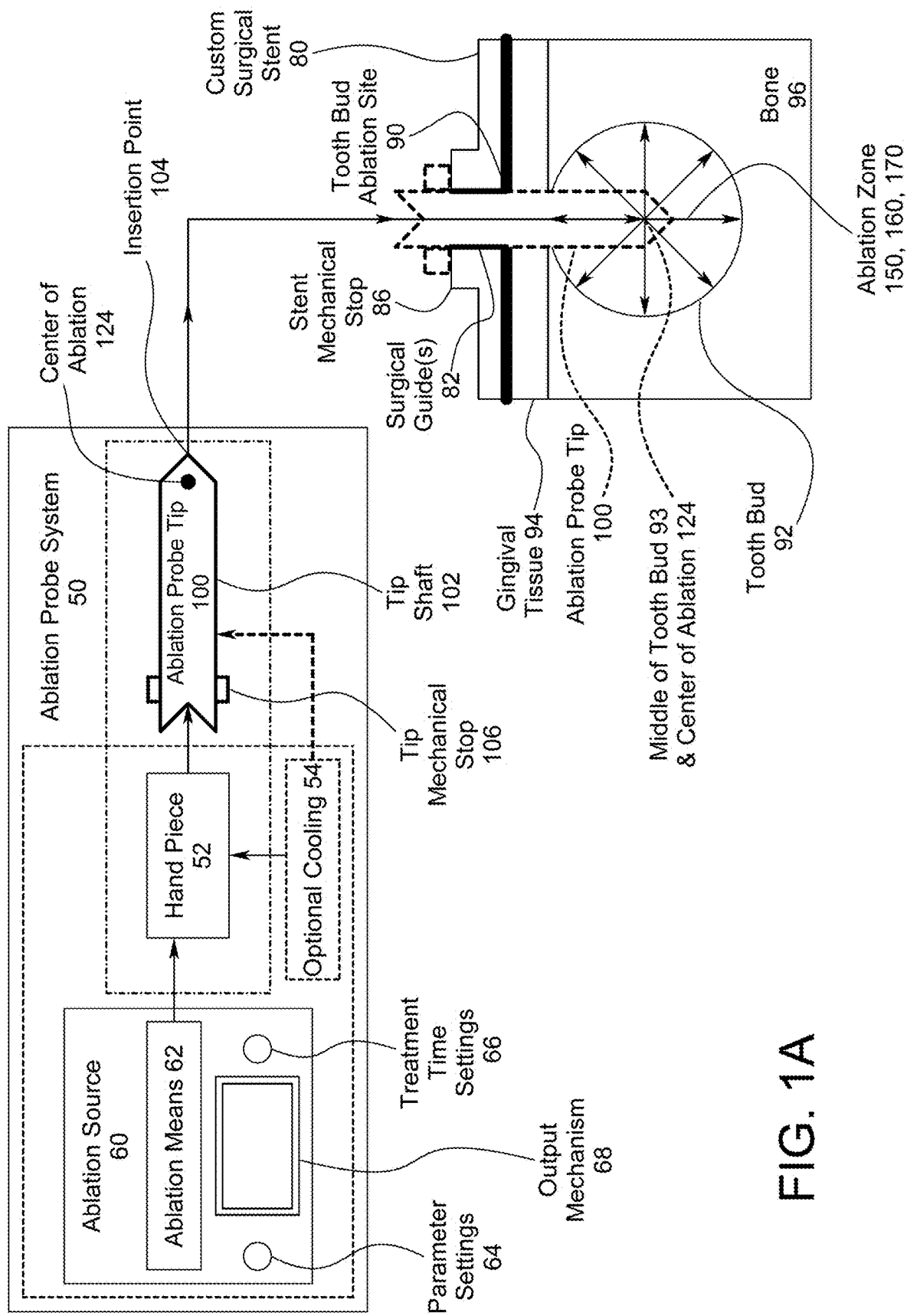
FIG. 1A is a simplified block diagram of an ablation probe system, a custom physical surgical stent, and a soft tissue ablation site.

The drawing figures are not necessarily to scale. Certain features or components herein may be shown in somewhat schematic form and some details of conventional elements may not be shown or described in the interest of clarity and conciseness. For example, even though a tooth bud is shown, any soft tissue can be considered. The drawing figures are hereby incorporated in and constitute a part of this specification.

DETAILED DESCRIPTION

The present disclosure describes apparatuses, methods/procedures, and systems that generally relate to the technical field of medical ablation probes. Some of the preferred apparatuses, methods/procedures, and systems described herein specifically relate to the technical field of microwave ablation (MWA) and radiofrequency ablation (RFA) probes that deliver controlled zones of soft tissue ablation.

Although the apparatuses, methods/procedures, and systems could be applied to any type of target tissue, tooth buds will be used as an exemplary target tissue throughout this document.

The ablation probe system (also referred to as "tooth bud ablation technology" or "micro-ablation technology") described herein allows the operator to precisely control at least one or more intra-operative parameters to deliver predictable clinical outcomes. Specific intra-operative controls include:
 I. Volume scan imaging guided positioning control (also referred to herein as "ablation zone positioning control" or "positioning control");
 II. Ablation zone shaping control (also referred to as "ablation zone shaping" or "shape ablation control");
 III. Ablation center control (also referred to as centering-directed ablation control);
 IV. Ablation zone temperature control;
 V. Guided ablation volume/diameter control (also referred to as "ablation zone volume/diameter control"); and
 VI. Power loading control (also referred to as "power density control").

Controlling various combinations of these controls and their respective parameters results in highly selective ablation of the targeted tissues while mitigating damage to immediately adjacent collateral tissues.

Figure 1B:
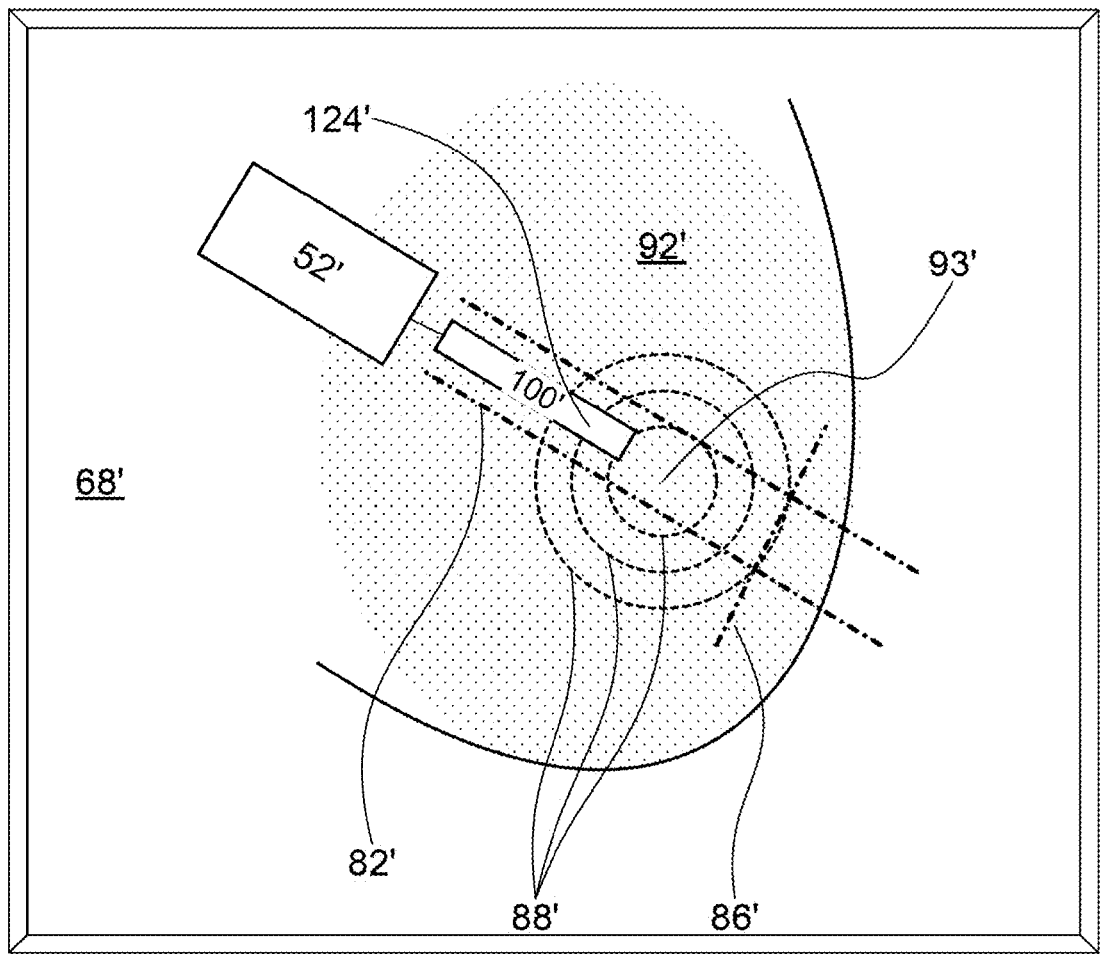
FIG. 1B is a simplified display showing virtual surgical guide angle markings, a virtual stop marking, and virtual target markings guiding a representation of a sensored hand piece and ablation probe tip.

The ablation probe system, as described herein, may be implemented as surgical micro-ablation kits (also referred to as "surgical kits," "surgical ablation kit," or "micro-ablation kits") that preferably contain a patient-specific micro-ablation probe (that may or may not be disposable) and a patient-specific high precision surgical guide (that may be a physical disposable guide as shown in FIG. 1A or a virtual guide as shown in FIG. 1B) used to position the probe during ablation. The high precision surgical guide is preferably suitable for directing the micro-ablation probe's center of ablation to within (and preferably the middle of) the tissue. Surgical kits may also include a "prescription" that indicates ablation energy dose tolerances and settings (e.g. level of energy and duration of energy deliverance) that should result in ablation of the targeted or predetermined volume of soft tissue. The micro-ablation kits may include and/or be used with an ablation source (e.g. a "smart" micro-ablation generator) and a hand piece.

The apparatuses, methods/procedures, and systems described herein produce zones of heating (ablation zones) that result in a defined volume of tissue hyperthermia. This focal hyperthermia induces a selective zone of cell death due to localized thermocoagulative necrosis that leads to tooth agenesis when a sufficient volume of tooth bud tissue has been destroyed (i.e. killing the cells, but destroying the tissue). The ablation, therefore, removes or destroys the predetermined target tissue while minimally damaging surrounding tissue or structure compared to more invasive conventional surgical techniques. Once the targeted tissue is destroyed, then the body's normal healing mechanisms will remove the destroyed tissue.

Live animal trials of tooth bud ablation using the apparatuses, methods/procedures, and systems described herein, have delivered microwave energy into the soft tissue at frequencies ranging from 500 MHz up to 20 GHz. Testing results from these trials have shown a 100% success of ablating target tissue ablation zones and clinically induced complete molar tooth agenesis with limited damage to adjacent non-target tissues. Further, there is excellent healing with all dead tissue removed, complete infilling of the bone, and no sign of any tooth formation arising from the targeted tooth bud within 4-6 weeks following treatment. Testing results show that using the ablation probe system will allow dental practitioners to deliver 20-40 second micro-ablation tooth bud ablation treatments in a highly controlled fashion when at least one of the intra-operative controls of the ablation probe system is employed.

The micro-ablation technology described herein is believed to be unique because it is the only known medical micro-ablation process with the ability to concurrently control positioning, shape, centering, peak temperature, and volume and/or diameter of the targeted ablation tissue.

There are many possible advantages of the preferred ablation probe systems 50 described herein. Some possible preferred advantages include, but are not limited to, the following advantages:
 Because of the heat transfer mechanisms, preferred ablation probe systems 50 can yield 20-40 second ablation times without overheating the tissue (and thereby avoiding tissue charring) with the possibility that longer ablation times can be used when lower power densities (power loading) are employed or when larger ablation volumes are prescribed.
 The energy dose delivered by preferred ablation probe systems 50 can be monitored and controlled for repeatability over a wide range of clinical conditions and operator skills.
 Preferred ablation probe systems 50 have ablation probe tips 100 (also referred to as probe tips 100, micro-ablation probe tips 100, and micro-ablation ablation probe tips 100) with shafts having a diameter of 3.8 mm (the diameter of a 7-gauge needle) down to 1.0 mm or less (the diameter of a 20-gauge needle) for applications that require such small dimensions.
 Because the ablation probe's center of ablation 124 (focal region 124) is stationary (the center of ablation 124 does not migrate during treatment), predetermining the outer margins of the ablation zone 150, 160, 170 to encompass only targeted tissues (e.g. at least part of a tooth bud 92) becomes significantly more predictable while reducing the risk of ablating surrounding tissue.
 The center of ablation 124 (focal region 124) is predetermined and, because it is stationary, its location remains known. The location of the active heating zone 125 surrounding the focal region 124 (and the tissue peak temperatures of the active heating zone 125), therefore, are significantly more predictable. When operating with a known power input the predictability of the active heating zone 125 at least reduces (and possibly eliminates) tissue "charring" into a black, undefined mass which, in turn, reduces (and possibly eliminates) the risk of adverse post operative healing (such as scarring).

Before describing the ablation apparatuses, methods/procedures, and systems and the figures, some of the terminology should be clarified. Please note that the terms and phrases may have additional definitions and/or examples throughout the specification. Where otherwise not specifically defined, words, phrases, and acronyms are given their ordinary meaning in the art. The following paragraphs provide basic parameters for interpreting terms and phrases used herein.
 The term "tissue" is meant to describe any of the distinct types of material of which people or animals are made, consisting of specialized cells and their products. The tissue may be soft tissue. The phrase "target tissue" (also referred to as "targeted tissue") is meant to describe the tissue that is desired to be ablated. Exemplary target tissue might be a tooth bud or a tumor. The phrase "surrounding tissue" is meant to describe the tissue surrounding the target tissue that should not be ablated.

The term "middle" (used in the phrases "middle of the tooth bud" or "middle of the tissue") is meant to describe a position within the targeted tissue (e.g. a tooth bud). The middle is not necessarily the absolute "middle" of the tissue. A "calculated middle" of the tissue to be ablated may be calculated by methods including, but not limited to, those using volume, three-dimensional position, and/or other known or yet to be discovered methods. A "predetermined middle" (or "predetermined position") may be the "calculated middle" of the tissue to be ablated or it may just be a known position within the tissue to be ablated. Unless specifically noted otherwise, where the "middle" is discussed, a calculated and/or predetermined middle within the tissue may be used.

The phrase "ablation zone" (also referred to as "zone of soft tissue ablation," "controlled zone of soft tissue ablation," "zone of ablation," "zone of heating," and "zone of temperature control") is meant to describe the area in which ablation will be created or has been created. Ideally, the ablation zone is substantially coextensive with the target tissue. The target tissue can also be thought of as the target ablation zone. The ablation zone has a three-dimensional area or volume even though photos and drawings herein may render them to appear as a two-dimensional image.

The term "micro-ablation" is meant to describe ablations that are smaller than 25.00 mm in diameter for use on smaller anatomical structures, such as a tooth bud, although they can be larger and used on tumors that exceed 5 cm in diameter. For micro-ablations, the probe tip 100 would be a micro-ablation probe tip. Unless specified otherwise, the phrase "probe tip" will include micro-ablation probe tips.

The phrase "ablation means" (as in ablation means 62) is meant to describe the mechanism (e.g. energy) by which ablation or micro-ablation is performed. Preferred ablation means may be energy such as microwave (MW) and/or radiofrequency (RF) and, in particular, microwave ablation energy in the range of 500 MHz to 20 GHz (broad spectrum) and radiofrequency ablation energy in the range of less than 500 MHz. This range would include both microwave ablation energy and RF ablation energy. The ablation means 62 is provided by an ablation source 60.

The phrase "ablation source" (as in ablation source 60) is meant to describe the mechanism by which the ablation means is produced. The ablation source 60 may be a purpose-built ablation source such as a "smart" micro-ablation generator. The ablation source may be a generator and/or an amplifier (jointly referred to as a generator). If the ablation means 62 is microwave ablation means, the ablation source 60 may be a microwave generator. If the ablation means 62 is radiofrequency ablation means, the ablation source 60 may be a radiofrequency generator. If the ablation source 60 is a "smart" generator it may be loaded with the procedure parameters (e.g. time, temperature, rate of energy delivered, frequency, and other parameters) that can then deliver the ablation means based on those parameters to the target tissue. A smart generator may have error checking and safety measures. For example, a smart generator can monitor for bad probe tips 100 by measuring forward power/energy and reflected power/energy to measure the total power/energy (energy/time) being delivered into the ablation zone. If the smart generator cannot reach the prescribed energy level and/or cannot maintain the prescribed energy level, then the procedure is stopped and an error message is generated.

Figure 23A:
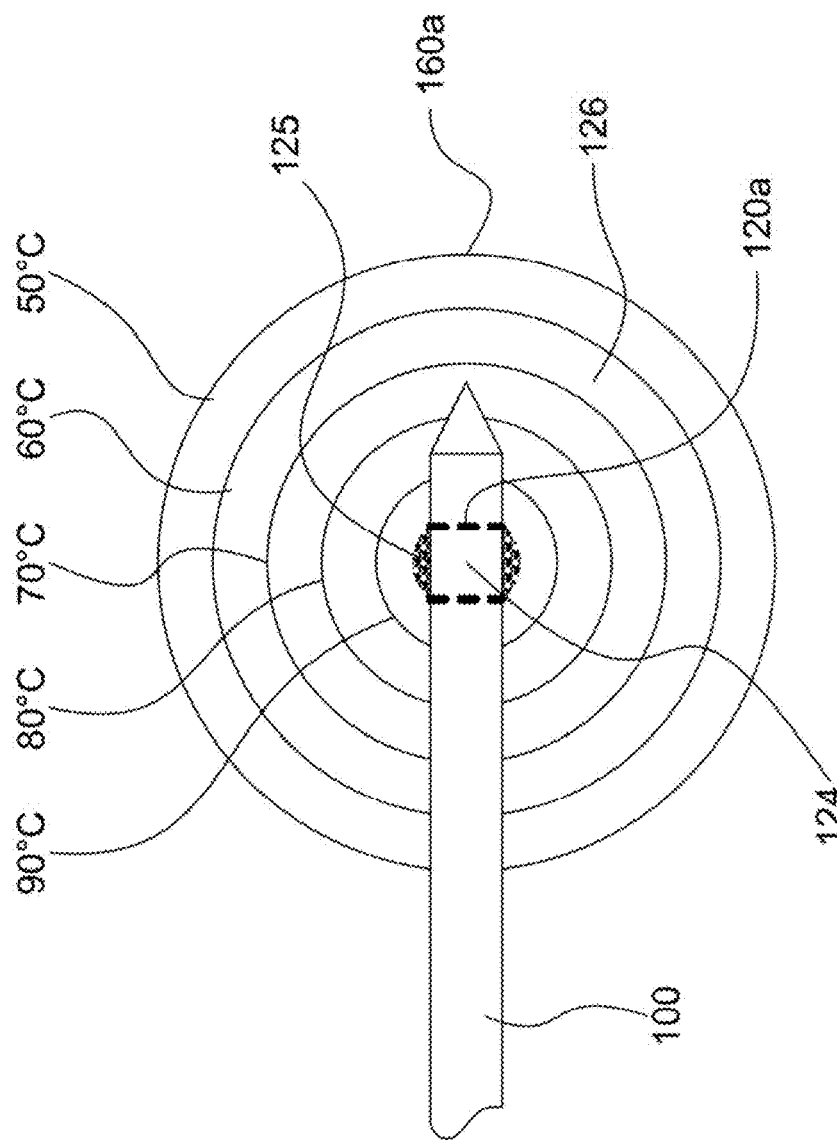
FIG. 23A is a graphical representation of an ablation probe with a short annular aperture (bounding a small focal region) and a short active heating zone that creates high power loading in the ablation zone.
Figure 23B:
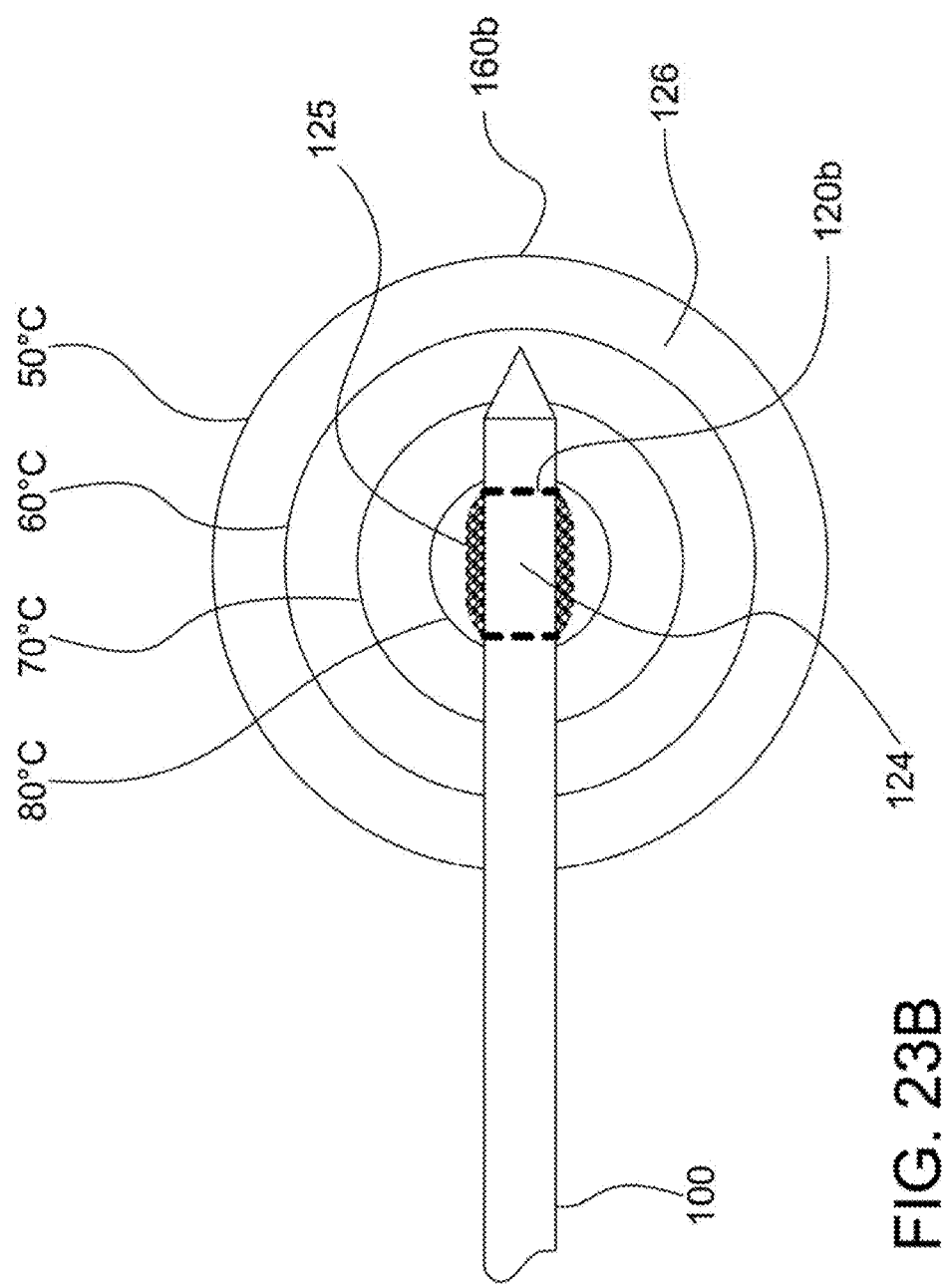
FIG. 23B is a graphical representation of an ablation probe with a medium annular aperture (bounding a medium focal region) and a medium active heating zone that creates medium power loading in the ablation zone.
Figure 23C:
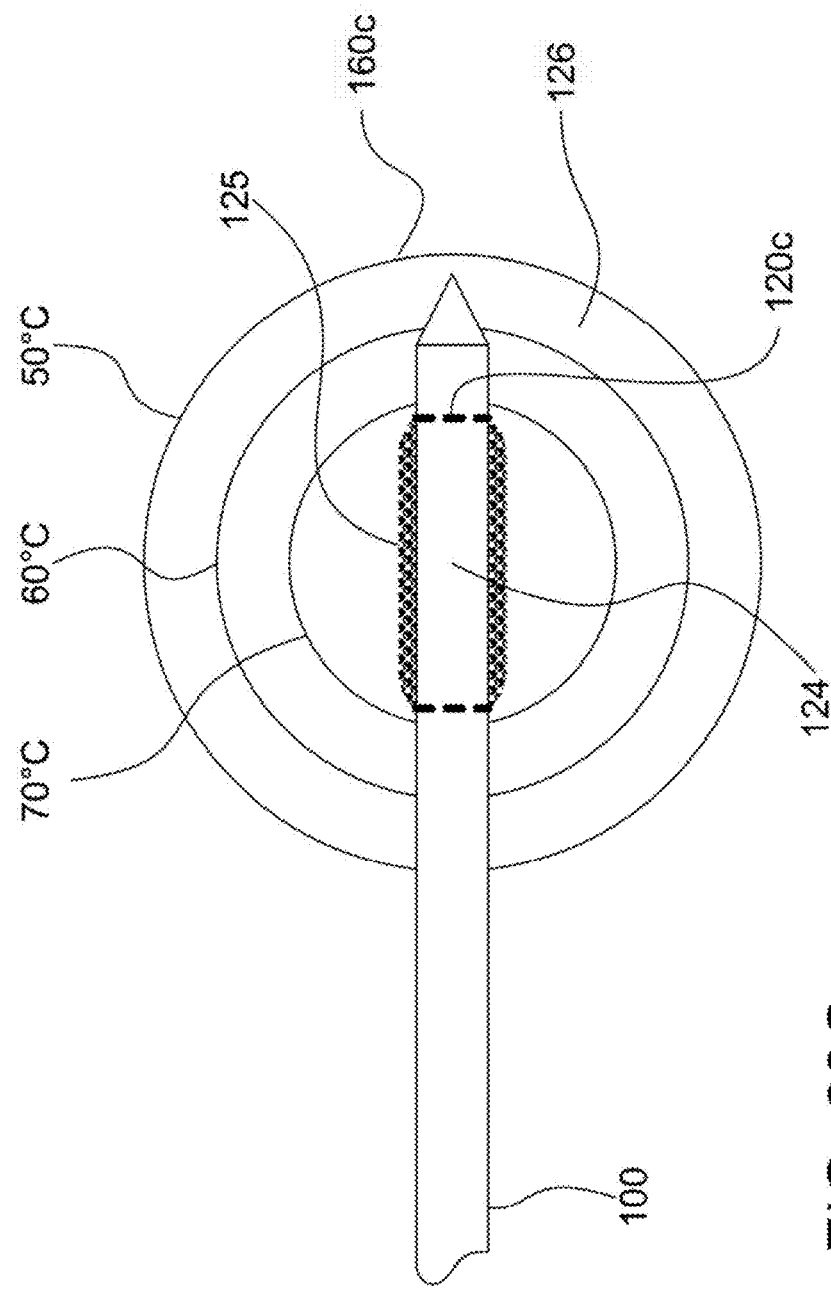
FIG. 23C is a graphical representation of an ablation probe with a long annular aperture (bounding a large focal region) and a long active heating zone that creates low power loading in the ablation zone.

The phrases "center of ablation" and "focal region" are meant to describe the portion of the inner conductor 112 that is bounded by the annular aperture 120 from which the ablation means 62 radiates. An active heating zone 125 surrounds the focal region 124. Surrounding the active heating zone 125 is an ablation zone 150, 160, 170. As shown in FIGS. 23A-23C, for example, the area of the ablation zone 160a, 160b, 160c (which are variations of the spherical ablation zone 160) beyond the active heating zone 125 is a thermal heating zone 126 (created by thermal conduction).

The phrases "active heating zone," "tissue active heating zone," "tissue zone of active heating," "zone of active heating," "active zone of heating," and variations thereof are meant to describe the target tissue within the ablation zone 150, 160, 170 that the ablation means 62 initially enters. As shown in FIGS. 23A-23C, for example, the active heating zone 125 is at least substantially annularly adjacent to annular aperture 120 of the probe tip 100. The active heating zone 125 is where the radiative energy is converted from radiative energy to thermal energy. The tissue within the ablation zone 150, 160, 170 that is located outside of the active heating zone 125 (i.e. within the thermal heating zone 126) still incurs cell death, but cell death within the thermal heating zone 126 is caused by heat conducting outwards from the active heating zone 125.

The phrases "power loading," "power density," "power loading density," and "volume power density" describe the amount of energy (e.g. microwave or radiofrequency energy) as a function of time (power being a unit of energy being delivered per unit of time) being delivered into the active heating zone 125. For example, a dipole antenna (a longer and lower power loading antenna) with no end load and a lower capacitive coupling will generally be two to four times longer than the shown shorter and higher power loading end-loaded antenna (e.g. an ablation probe tip 100 having an end load 122). In this example, microwave energy spreads over the longer antenna in a predefined fashion before radiating outwards into the active heating zone 125. The spread of the energy in the longer antenna results in a power loading density in the active heating zone 125 that is two to four times lower when compared to the higher power loading in the shorter antenna delivering the same amount of energy per unit of time.

The term "profile" (as used in the phrases "ablation zone profile," "probe profile," "ablation profile," "probe ablation profile," and "ablation zone margins" or "ablation zone tissue margins" is meant to describe the known attributes and variables of the ablation zone associated with a particular ablation probe system 50 and/or the ablation zones 150, 160, 170 it produces in soft tissues. These attributes and variables include, but are not limited to, the shape (e.g. oblate, spherical, oblong) of the ablation zone the ablation probe system 50 produces, the size (e.g. dimensions and volume) of the ablation zone the ablation probe system 50 produces, the location of the ablation zone along the length of the probe tip 100, the temperature of the ablation zone the ablation probe system 50 produces, and the time (duration) it takes the ablation probe system 50 to produce the ablation zone. The attributes and variables may be interrelated with each other. For example, the size of the ablation zone the ablation probe system 50 produces may be directly related to how much ablation means 62 (e.g. microwave energy) is used and how long the ablation means 62 is used. Using an ablation probe system 50 having the appropriate profile with the appropriate input for the appropriate duration will produce the desired ablation zones 150, 160, 170.

The phrase "volume scan" (as well as "volume scanning" and other variations used herein) is meant to include any volume scanning technology known or yet to be discovered that at least relatively safely accurately generates the necessary multi-dimensional images that can be used in medical procedures. Exemplary volume scan imaging includes, but is not limited to, computed tomography (CT) (e.g. cone beam computed tomography (CBCT)), X-ray, magnetic resonance imaging (MRI), ultrasound, nuclear medicine imaging (e.g. positron-emission tomography (PET)), and other types of volume scan imaging or three-dimensional soft tissue imaging that may be used or be adapted to be used to implement the functions described herein. The phrase and variations thereof may be used as a noun (e.g. the image) or a verb (the process of taking the image). Whether the phrase is used as a noun or a verb can be determined from the context in which it is used.

The term "image" is meant to describe both the process of taking a "picture" and the "picture" itself, the difference therebetween apparent from context. The "picture" may be a volume scan image such as a cone-beam image (produced, for example, by a computed tomography (CT) image (e.g. cone beam computed tomography (CBCT) image), an X-ray image, a magnetic resonance imaging (MRI) image, an ultrasound image, a nuclear medicine image (e.g. a positron-emission tomography (PET) image), or any image means known or yet to be discovered that can show the target tissue and surrounding tissue in sufficient detail to allow the system and methods described herein to be used. In some instances, a specific type of imaging is suggested, but other imaging may be used if it may accomplish the same purpose. For example, panographic imaging is suggested for routine screening for tooth buds, but other types of imaging known or yet to be discovered could be used to screen for tooth buds and measure tooth bud soft tissue dimensions. When used as a verb, the term "image" is the process of taking an "image" as described above.

Electromagnetic fields around objects such as antennas can be divided into regions including "near field" (which can additionally be divided into non-radiative (reactive) and radiative (fresnel)) and "far field." Non-radiative "near field" behaviors dominate close to the antenna, while "far field" behaviors dominate at greater distances. In near field regions, there is interference with the propagation of electromagnetic waves and, therefore, the near field regions are considered unpredictable. By contrast, in far field regions, the field acts as "normal" with a relatively uniform wave pattern. Ablation probe systems 50 described herein are preferably designed to function in the near field region.

The ablation system described herein may have associated hardware, software, and/or firmware (a variation, subset, or hybrid of hardware and/or software). The term "hardware" includes at least one "processing unit," "processor," "computer," "programmable apparatus," and/or other known or yet to be discovered devices capable of executing instructions or steps. The term "software" includes at least one "program," "subprogram," "series of instructions," or other known or yet to be discovered hardware instructions or hardware-readable program code. Exemplary software includes the surgical stent design software suite described herein. Software may be loaded onto hardware (e.g. the ablation source 60) to produce a machine, such that the software executes on the hardware to create structures for implementing the functions described herein. Further, the software may be loaded onto the hardware (e.g. the ablation source 60) to direct the ablation probe system 50 to function in a particular manner described herein or to perform a series of operational steps as described herein. The phrase "loaded onto the hardware" also includes being loaded into memory associated with or accessible by the hardware (including firmware). The term "memory" (e.g. the memory of the ablation source 60) is defined to include any type of hardware (or other technology)-readable media (also referred to as machine-readable storage medium) including, but not limited to, attached storage media (e.g. hard disk drives, network disk drives, servers), internal storage media (e.g. RAM, ROM, EPROM, FLASH-EPROM, or any other memory chip or cartridge), removable storage media (e.g. CDs, DVDs, flash drives, memory cards, floppy disks, flexible disks), firmware, and/or other known or yet to be discovered storage media. Depending on its purpose, the memory may be transitory and/or non-transitory. Appropriate "communications," "signals," and/or "transmissions" (which include various types of information and/or instructions including, but not limited to, data, commands, bits, symbols, voltages, currents, electromagnetic waves, magnetic fields or particles, optical fields or particles, and/or any combination thereof) over appropriate "communication paths," "transmission paths," and other means for signal transmission including any type of connection between two elements of the system (the system including, for example, the ablation source 60, the hand piece 52, the ablation probe tip 100, other hardware systems and/or subsystems, and/or memory) would be used as appropriate to facilitate controls and communications.

The term "associated" (and variations such as "associable"), when used in the context of a connection between components, is defined to mean integral or original, retrofitted, attached, connected (including functionally connected), positioned near, and/or accessible by. For example, if a display (such as the output mechanism 68 or other component) is associated with a computer (including a processor associated with the ablation source 60 or other technology), the display may be an original display built into the computer, a display that has been retrofitted into the computer, an attached display that is attached to the computer, a nearby display that is positioned near the computer, and/or a display that is accessible by the computer. Another example is the connection between the ablation source 60, the hand piece 52, and the ablation probe tip 100 are described as associable in that the connections between these items may be integral or original, retrofitted, attached, connected (including functionally connected), positioned near, and/or accessible by.

The terms "may," "might," "can," and "could" are used to indicate alternatives and optional features and only should be construed as a limitation if specifically included in the claims. It should be noted that the various components, features, steps, designs, or embodiments thereof are all "preferred" whether or not it is specifically indicated. Claims not including a specific limitation should not be construed to include that limitation.

Unless specifically stated otherwise, the term "exemplary" is meant to indicate an example, representation, and/or illustration of a type. The term "exemplary" does not necessarily mean the best or most desired of the type.

It should be noted that, unless otherwise specified, the term "or" is used in its nonexclusive form (e.g. "A or B" includes, but is not limited to, A, B, A and B, or any combination thereof). It should be noted that, unless otherwise specified, "and/or" is used similarly (e.g. "A and/or B" includes, but is not limited to, A, B, A and B, or any combination thereof). It should be noted that, unless otherwise specified, the terms "includes," "has," and "contains" (and variations of these terms) mean "comprises" (e.g. a device that "includes," "has," or "contains" A and B, comprises A and B, but optionally may contain C or additional components other than A and B).

It should be noted that, unless otherwise specified, the singular forms "a," "an," and "the" refer to one or more than one, unless the context clearly dictates otherwise. Similarly, unless specifically limited, the use of singular language (e.g. "component," "module," or "step") may include plurals (e.g. "components," "modules," or "steps"), unless the context clearly dictates otherwise.

I. Volume Scan Guided Positioning and Ablation Control

Volume scan, as described herein is any scanning technology that at least relatively safely can accurately generate the necessary multi-dimensional images that can be used in ablation procedures. "Volume scan guided positioning and ablation control" is also referred to as "volume scan guided control" and "volume scan guided procedures." "Volume scan guided positioning and ablation control" includes as "volume scan guided positioning control," as "volume scan guided ablation control," and "volume scan guided soft tissue ablation." Volume scan guided control is a technology for precisely positioning an ablation probe tip and then ablating the desired soft tissue by delivering the predetermined amount of energy based upon the soft tissue dimensions measured in the volume scan. Positioning may be accomplished by physically using a physical stent as shown in FIG. 1A) and/or virtually using a virtual stent as shown in FIG. 1B). Ablating may be accomplished by heating a predetermined soft tissue volume by controlling the energy delivery. Such physical and virtual stents are described in the Therapeutic Tooth Bud Ablation Properties. For example, the creation of a custom surgical stent using location and measurement information about the tooth bud obtained from a scan is described in the Therapeutic Tooth Bud Ablation Properties as well as herein. Volume scan guided positioning control (e.g. a stent) may be created from pre-operative measurements obtained using volume scan technology. Exemplary steps for creating a stent include, but are not limited to:

Selecting an ablation probe tip (which may be a sensored ablation probe tip) with known dimensions and capabilities. Information about the dimensions and capabilities may be stored in a volume scan information technology file (e.g. a three-dimensional computer aided design (CAD) file).

Using volume scanning technology, scanning a patient's mouth. Information (including a volume scan image) from the volume scan may be stored in a scanning technology file (e.g. the volume scan information technology file).

From the volume scan, creating physical (traditional) or digital impressions of the patient's teeth and gum tissue (gingival tissue). If a digital impression is created, it may be stored in a volume scan information technology file.

From the volume scan or information in the volume scan information technology file, obtaining (e.g. calculating and/or measuring) the tooth bud size and position using information in the volume scan information technology file. Information about the tooth bud size and position may be stored in a volume scan information technology file.

From the volume scan or information in the volume scan information technology file, locating a landmark (e.g. the distal side of erupted first molars or soft tissue over bone). Information about the location of the landmark in relation to the tooth bud may be stored in a volume scan information technology file.

From the volume scan or information in the volume scan information technology file, locating or obtaining (e.g. calculating and/or measuring) the middle of the tooth bud (calculated middle) or at least a position within the tooth bud (a predetermined position). Information about the middle of the tooth bud may be stored in a scanning technology file.

From the volume scan or information in the volume scan information technology file, obtaining (e.g. calculating and/or measuring) a predetermined angle (the angle at which the ablation probe tip's effective center of ablation is in the middle of the tooth bud—shown as 90 degrees in FIG. 2) to guide the ablation probe tip. The angle could be calculated/measured from a known point (e.g. the landmark or the point of entry—taking into consideration the thickness and surface of a physical stent and the shape of the ablation probe tip) to the middle of the tooth bud. Information about the predetermined angle may be stored in a scanning technology file.

From the volume scan or information in the volume scan information technology file, obtaining (e.g. calculating and/or measuring) predetermined depth (the depth at which the ablation probe tip's effective center of ablation is in the middle of the tooth bud) to limit the depth of the ablation probe tip. The depth could be calculated/measured from a known point (e.g. the landmark or the point of entry—taking into consideration the thickness and surface of a physical stent and the shape of the ablation probe tip) to the middle of the tooth bud. In FIG. 2, the depth D is shown as the distance between the upper surface of the gingival tissue and the center of ablation or, alternatively, the depth D+D' is shown as the distance between the upper surface of the stent and the center of ablation. If there was a raised mechanical stop (as shown in FIG. 1A), its height could also be added to the depth. Information about the predetermined depth may be stored in a scanning technology file.

Processing the information in the volume scanning technology file(s) (which may be one file or multiple files) to put the information into a form that can be used for creating or manufacturing a stent (physical or virtual) and to create a "prescription" that indicates ablation energy dose tolerances and settings (e.g. level of energy and duration of energy deliverance) in order to be guided in selectively ablating the targeted tissues. "Creating" includes "manufacturing" such that both the virtual stent and the physical stent are created, but only the physical stent is manufactured. Depending on what is being "created," "creating" (and variations thereof) may also include programming, gathering, or other ways of bringing into existence.

Creating or manufacturing a stent (virtual or physical) with at least one surgical guide (virtual or physical) to guide the ablation probe tip at the predetermined angle and at least one stop structure (virtual or physical) to limit the depth of the ablation probe tip to the predetermined depth. If the stent is physical, it may have mechanical stop structure that interacts with the stent's mechanical stop structure.

Using the stent surgical guide and mechanical stop structure, the ablation probe tip may be guided such that said center of ablation is within said tooth bud (and, preferably, at the middle of the tooth bud) when the ablation probe tip is guided at said predetermined angle to said predetermined depth.

FIGS. 1A, 1B, 2, and 3 show a basic system that uses volume scan guided positioning controls (shown as a physical stent 80 or a virtual stent 82', 86', 88') to properly position ablation probe systems 50 (including the probe tip 100) that deliver shaped, centered, temperature controlled, and/or volume controlled target tissue ablation. Volume scan guided procedures accurately position the micro-ablation probe to assure that the tooth bud tissue will be warmed from within (including from the middle of) the tooth bud outwards to a defined volume with outer soft tissue ablation margins in their desired location. Doing so results in safe and effective tooth bud ablation while mitigating damage to adjacent collateral tissues next to the tooth bud. There is no known competing technology that has this level of accuracy for three-dimensional (3D) positioning of the zone of ablation and holding the zone in position throughout the procedure.

Although some exemplary ablation probe system(s) 50 and components thereof are described in more detail herein, FIGS. 1A, 1B, 2, and 3 provide a broad overview of an exemplary ablation probe system 50 as it is used in an exemplary application (tooth bud ablation). The ablation probe system 50 may work in conjunction with a custom surgical stent (the physical stent 80 shown in FIG. 1A or the virtual stent 82', 86', 88' shown in FIG. 1B) at a tooth bud ablation site 90. Robotics could also be used in volume scan guided soft tissue ablation, the robotics being a form of guidance that may be used with either the physical system or the virtual system. Some exemplary physical guides and virtual guides are described in the Therapeutic Tooth Bud Ablation Properties. For other non-tooth bud procedures, where the ablation site could be a site (location on a body) covering any target tissue, an appropriate surgical stent could be used to guide placement of the probe tip. For example, if the tumor were on a leg, a physical or virtual stent appropriate to a leg would be used.

As shown in FIG. 1A, an ablation probe system 50 (or ablation probe 50) includes an ablation probe tip 100, a hand piece 52, and an ablation source 60 which provides and/or facilitates the provision of an ablation means 62. The ablation probe tip 100 may be integral or connectable (directly or indirectly) or otherwise associable with the hand piece 52. The hand piece 52 may be integral or connectable (directly or indirectly) or otherwise associable with the ablation source 60. The hand piece 52 may be autoclavable. One type of indirect connection could include the use of a wire or cable that functionally connects components. Another type of indirect connection could include remote control mechanisms (e.g. appropriate transmitters and receivers) that functionally connect components.

Figure 3:
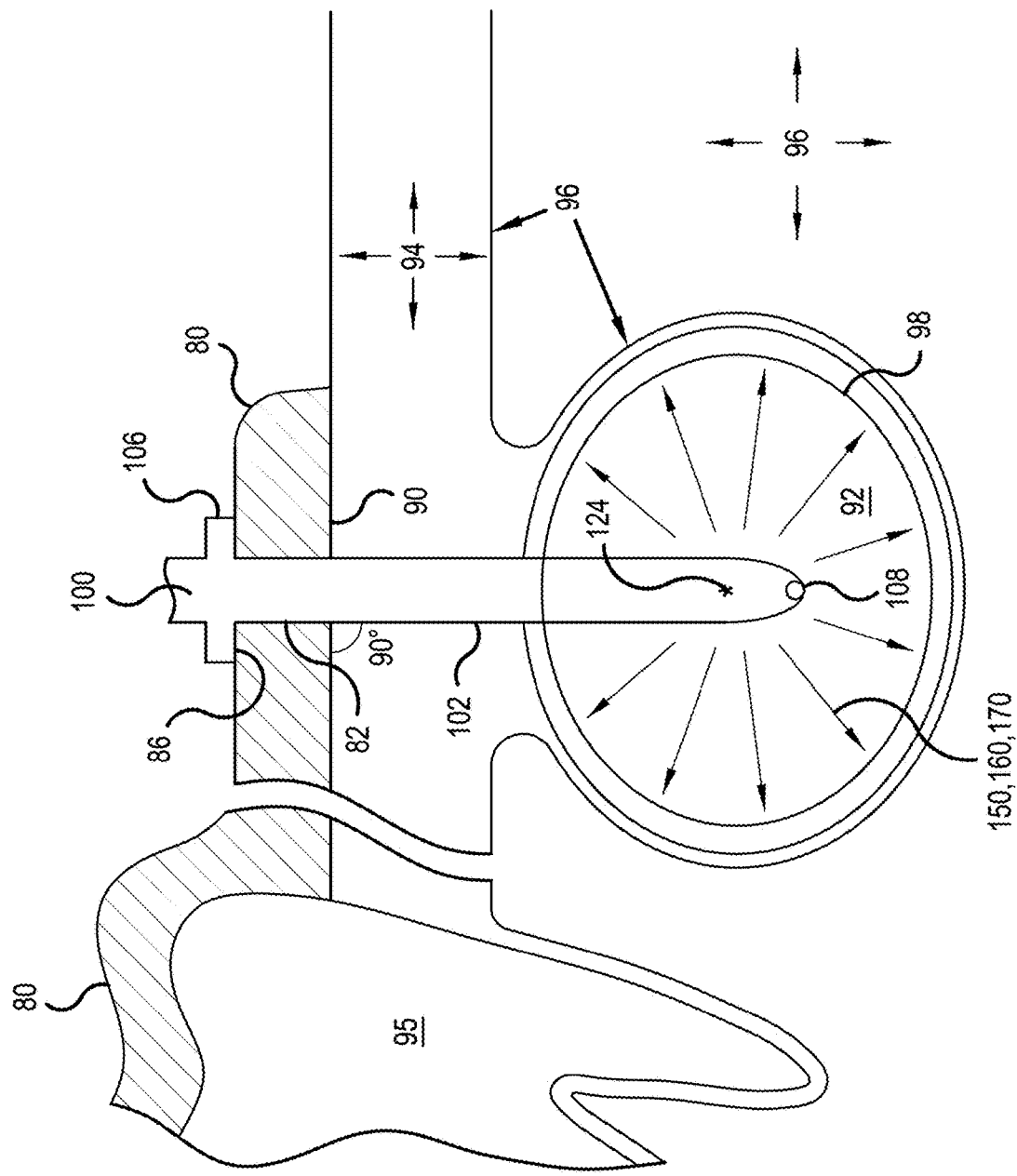
FIG. 3 is a simplified cross-sectional view of an exemplary soft tissue ablation site within an oral cavity, the ablation probe tip positioned by the stent such that the center of ablation is within the soft tissue, radiating arrows representing an exemplary ablation zone.
Figure 4:
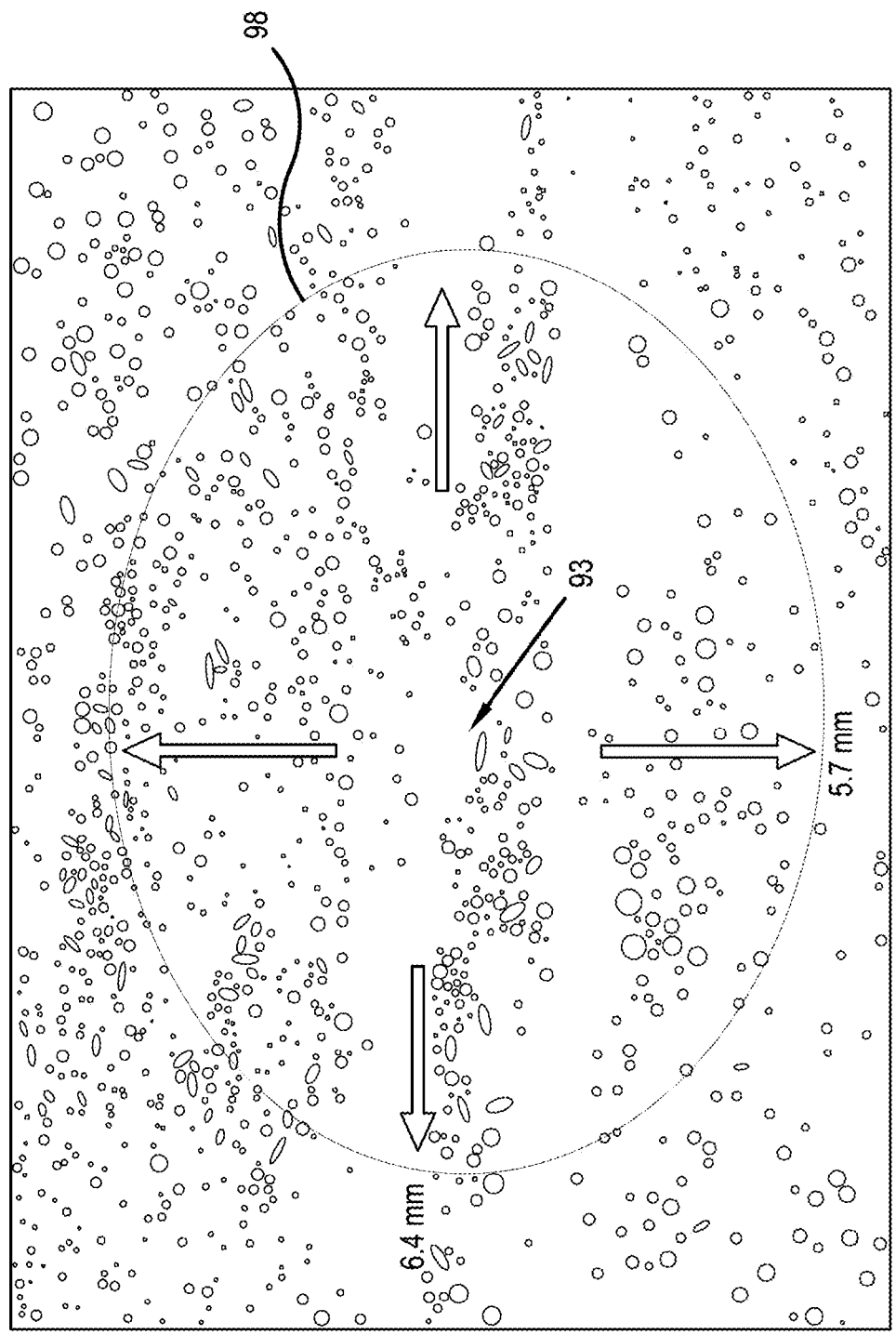
FIG. 4 is a cross-sectional view of tissue having a "middle" with radiating arrows representing an exemplary ablation zone and the oval outline representing predetermined outer limits of the ablation zone.

FIGS. 1A, 2, and 3 show volume scan guided positioning control implemented as a custom surgical stent 80 having at least one surgical guide 82 (shown as darkened solid lines through the surgical stent 80 in FIG. 1A) and a stent mechanical stop 86 (which, as shown in FIG. 1A, may be a raised portion of the stent 80 at least relatively adjacent to the surgical guide 82 or, as shown in FIGS. 2-3, just the upper surface of the stent 80 at least relatively adjacent to the surgical guide 82). The stent 80, guide 82, and stop 86 together are a form of volume scan guided positioning control created using the process described herein. FIGS. 2-3 show that at least part of the surgical stent 80 may be at least partially supported by at least one erupted tooth. The custom surgical stent 80 is positioned so that a surgical guide 82 covers and/or surrounds the tooth bud 92 at the tooth bud ablation site 90 (including gingival tissue 94 and bone 96 (including the dense cortical bone)). FIG. 4 shows tissue (e.g. a tooth bud) having a middle 93 with radiating arrows that represent an exemplary ablation zone and the oval outline that represents predetermined outer limits 98 of the ablation zone.

The ablation probe tip 100 (shown in FIG. 1A with solid lines before insertion and dashed lines after insertion) has a tip mechanical stop 106 and a center of ablation 124. The ablation probe tip 100 is insertable through gingival tissue 94 and into the tooth bud 92 (which is located within the bone 96 of a jaw). The ablation probe tip 100 is guided by the stent 80 so that its insertion end 104 and center of ablation 124 would be within (e.g. at or near the middle 93 of) the tooth bud 92. The interaction between the surgical guide 82 and the tip shaft 102 guides the ablation probe tip 100 at the correct angle (shown as a 90 degree or straight angle, but could be other angles) so that the center of ablation 124 is within the tooth bud 92. More specifically, the interior diameter of the surgical guide 82 is just slightly larger than the outer diameter of the tip shaft 102 such that the ablation probe tip 100 inserted into the surgical guide 82 can only be inserted at the angle dictated (prescribed) by the surgical guide 82. Limiting the ablation probe tip 100 to the correct depth so that the center of ablation 124 is within the tooth bud 92 may be accomplished, for example, by the interaction between the stent mechanical stop 86 and the tip mechanical stop 106 (which may be, for example, a raised surface (FIG. 1A), an angled surface, and/or the top surface (FIGS. 2-3) of the stent 80). Preferably the center of ablation 124 is positioned at least substantially in the middle (e.g. calculated middle) of the tooth bud 92 as determined by volume, three-dimensional position, and/or other known or yet to be discovered methods. (The calculated or predetermined middle of the tissue to be ablated is the "middle of the tooth bud" 93.) The ablation probe tip 100 is positioned before the ablation means 62 is activated to create the ablation zones 150, 160, 170 (the radiating arrows—although only a single type of zone is shown in these figures, it is representative of differently shaped zones shown and discussed herein in relation to FIGS. 9 and 11-13). As shown in FIG. 3, the predetermined outer limits 98 of the ablation zone are preferably +/−0.50 mm within the bony crypt of the tooth bud 92.

FIG. 1B shows a virtual stent system (82', 86', 88') that can be used with a sensored ablation probe tip 100' and/or a sensored hand piece 52'. The virtual stent may be dynamic navigation technology that is implemented as at least one software program (or subprogram) associated with the ablation source 60. The program would be able to receive input (e.g. the prescription) and convert the input to a virtual stent. Although the virtual stent could be used by itself, it could also be used in conjunction with a physical stent. For example, it could provide advanced notice as to approaching parameters (e.g. an audible "the tip is approaching the stop") or confirmation (e.g. a light flash on the handle or a pleasant audible "ding" when the probe tip is in position). Another example is that the surgical guide could be implemented physically, but the stop and/or target could be implemented virtually.

The virtual stent system could be shown on a visual display 68' with surgical guide angle markings 82', a virtual stop marking 86', and virtual target markings 88' overlaying an image (e.g. a volume scan) of the area 92' (e.g. tooth bud) to be ablated (for clarity, the actual image has been omitted). Although shown as lines (e.g. dashed lines), alternative visual position indicators could be a digital readout or color coding. The virtual surgical guide angle markings 82' are based on the three-dimensional path of insertion (defined by the predetermined angle (e.g. the 90 degree angle shown in FIG. 2) and predetermined depth (e.g. the depth D shown in FIG. 2)). In preferred embodiments, the system would not be able to be activated if the center of ablation was not in proper relationship to the middle of the tooth bud.

In addition to or in conjunction with a physical stent 80 and a virtual stent displayed on a visual display '68, alternative audible, visual, and/or tactile indications can be used as a surgical guide, stop, and/or target. For example, signals (e.g. an audible series of beeps, a series of flashing lights, or physical vibrations) could be used to indicate the probe tip is getting closer to the ablation zone. For example, the beeps/flashes/vibrations could get louder/brighter/faster as the probe tip approaches the ablation zone. Alternatively, the indicators could be a voice speaking the instructions (e.g. "3 mm . . . 2 mm . . . 1 mm) or the light could be color-coded (e.g. red to green). Another example is that the virtual stop and/or virtual target could be implemented audibly, visually, and/or tactilely using similar or different indicators.

In use, the sensored ablation probe tip 100' may be guided by the virtual surgical guide angle markings 82' and the virtual stop marking 86' to a position in which the effective center of ablation 124' of the ablation probe tip 100' is in the middle of the tooth bud 93'. The operator may watch the insertion process on the display 68' as he physically manipulates the sensored ablation probe tip 100'. The virtual target markings 88' may also provide an indication that the sensored ablation probe tip 100' is within approximately 50%, 25%, and 10% of the average diameter of the tooth bud 92'. If the operator were manually manipulating the sensored ablation probe tip 100', the system would monitor the progress and alert the operator that the ablation probe tip 100' is not at the proper position using, for example, visual indicators, audible indicators, tactile indicators, or a combination thereof. Alternatively, the operator may monitor the progress on the display 68' as the sensored ablation probe tip 100' is inserted automatically (e.g. using a robotics system). Monitoring and override safeguards are preferably included in the system. For example, the system would not activate if the center of ablation was not in proper relationship to the middle of the tooth bud regardless of whether the insertion was performed manually or robotically.

When the probe tip 100 is properly positioned, the center of ablation 124 is within the tooth bud 92 at its predetermined position. Activating the ablation means 62 creates an ablation zones 150, 160, 170 (e.g. for a spherical tooth bud 92 (FIG. 1A) the appropriate ablation zone would be a spherical ablation zone 160, but for an oblate tooth bud 92 (FIGS. 2-3) the appropriate ablation zone would be an oblate ablation zone 150) centered about the center of ablation 124 within the tooth bud 92. If the ablation source 60 is a microwave generator, the ablation means 62 would be microwave energy. Ablation source parameter settings 64 and treatment time settings 66 may be provided by loading digital data (e.g. downloading parameter settings 64 and/or treatment time settings 66 using a provided "patient identification key" entered at a provided website address) or they may be provided by a user manually entering the data.

Feedback from the ablation source 60 or from the ablation probe tip 100 (which may have at least one sensor 108 along the shaft 102 to monitor, for example, temperature) may be provided to the user (or to electronic or digital monitoring systems that may be implemented by software associated with an ablation source 60 (e.g. a smart generator)) using an output mechanism 68 such as a video display or audio display (speaker).

Figure 5:
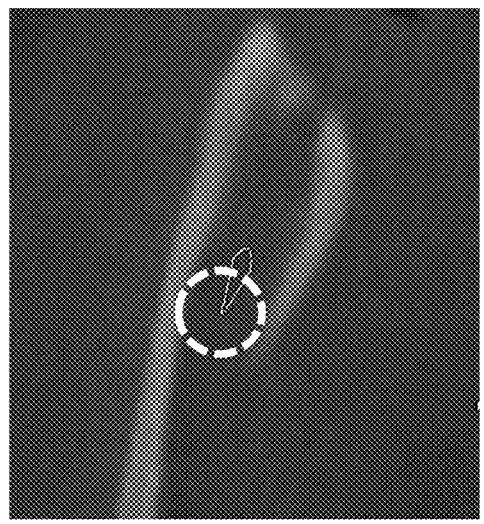
FIG. 5 is a computed tomography (CT) cross-sectional image of an axial view of a tooth bud.
Figure 6:
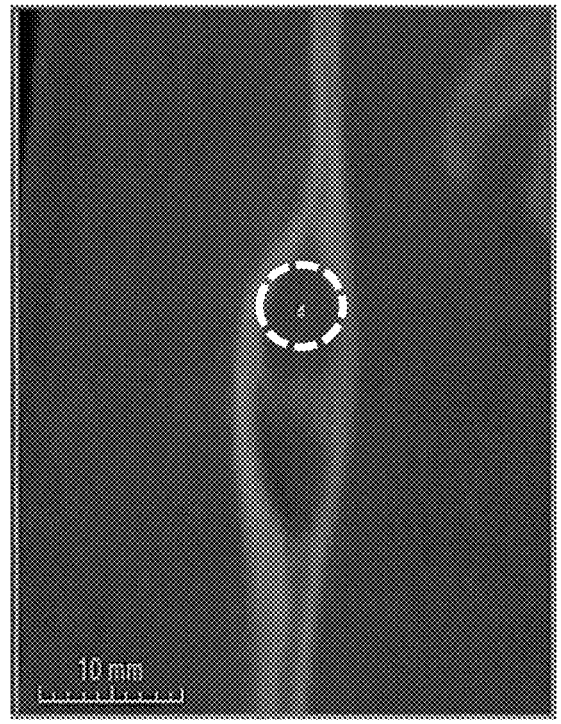
FIG. 6 is a CT cross-sectional image of a coronal view of a tooth bud.
Figure 7:
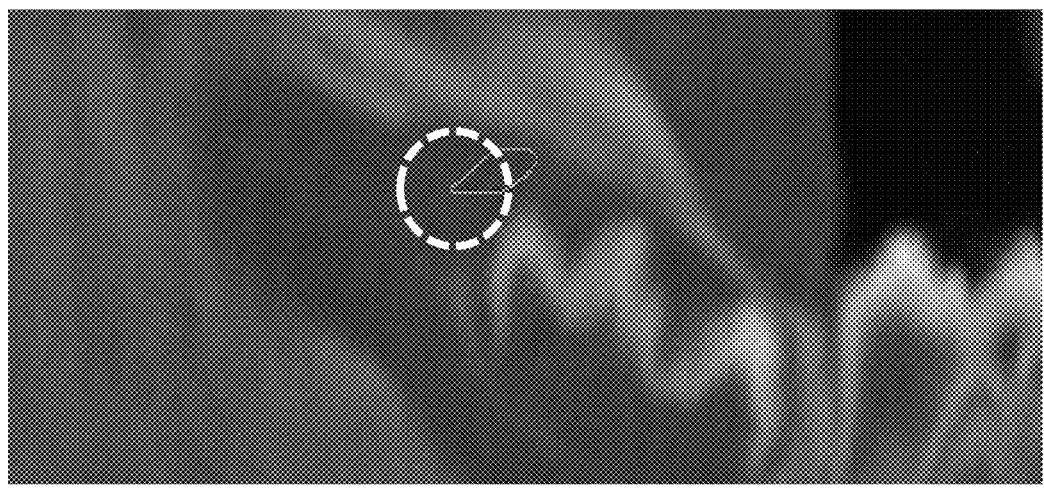
FIG. 7 is a CT cross-sectional image of a sagittal view of a tooth bud.

The volume scan (in this case a CT volume scan) cross-sectional images in FIGS. 5-7 show the planned center-positioning of the ablation probe tip 100 inside a mandibular tooth bud (circled in dashed lines) of a pig (similar images could be taken of a human tooth bud). More specifically, FIG. 5 shows the axial view of a tooth bud, FIG. 6 shows the coronal view of a tooth bud, and FIG. 7 shows the sagittal view of a tooth bud.

It should be noted that the components of FIG. 1A are not to scale (for example, the ablation probe tip 100 would most likely be much smaller than the hand piece 52).

II. Ablation Zone Shaping Control

Figure 14A:
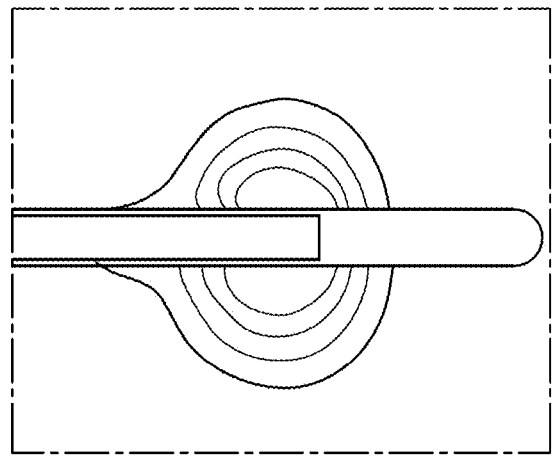
FIG. 14A is a graphical representation of an ablation probe and an oblate (aspect ratio >1.0) heating pattern that results in an oblate soft tissue ablation zone.
Figure 14B:
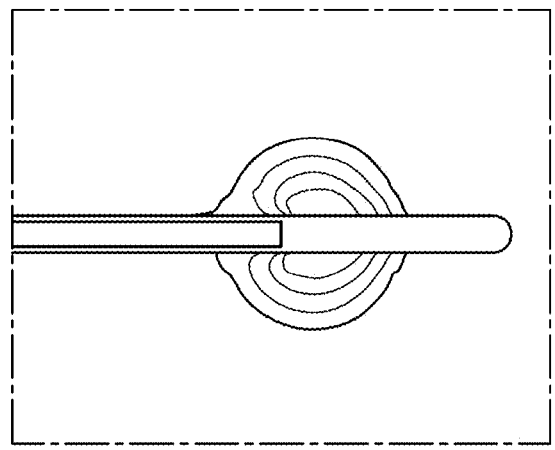
FIG. 14B is a graphical representation of an ablation probe and a spherical (aspect ratio=1.0) heating pattern that results in a spherical soft tissue ablation zone.
Figure 14C:
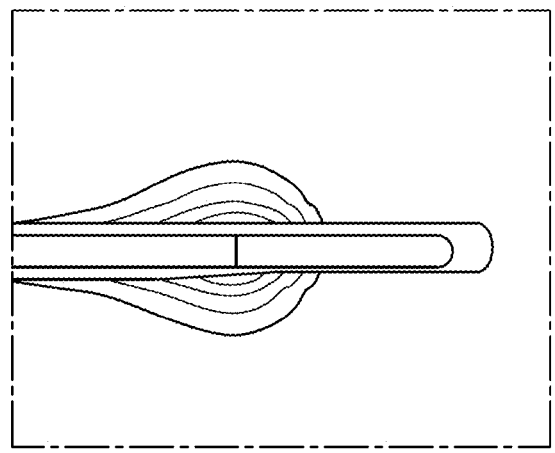
FIG. 14C is a graphical representation of an ablation probe and an oblong (aspect ratio <1.0) heating pattern that results in an oblong soft tissue ablation zone.
Figure 15A:
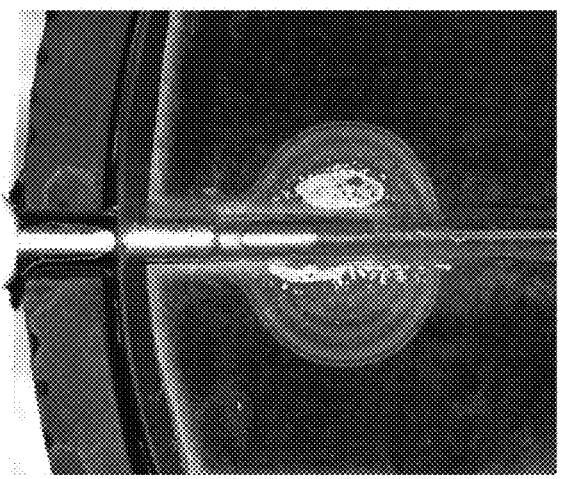
FIG. 15A is a photographic representation of an ablation probe and an oblate (aspect ratio >1.0) heating pattern that results in an oblate soft tissue ablation zone.
Figure 15B:
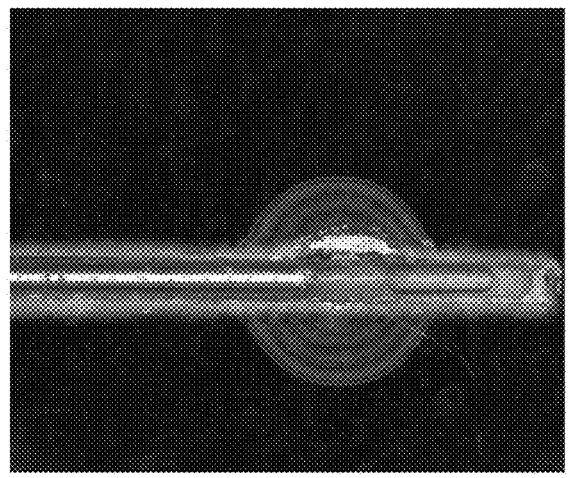
FIG. 15B is a photographic representation of an ablation probe and a spherical (aspect ratio=1.0) heating pattern that results in a spherical soft tissue ablation zone.
Figure 15C:
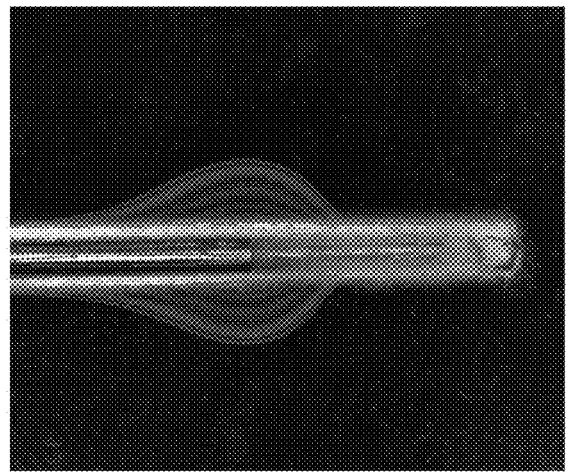
FIG. 15C is a photographic representation of an ablation probe and an oblong (aspect ratio <1.0) heating pattern that results in an oblong soft tissue ablation zone.
Figure 16A:
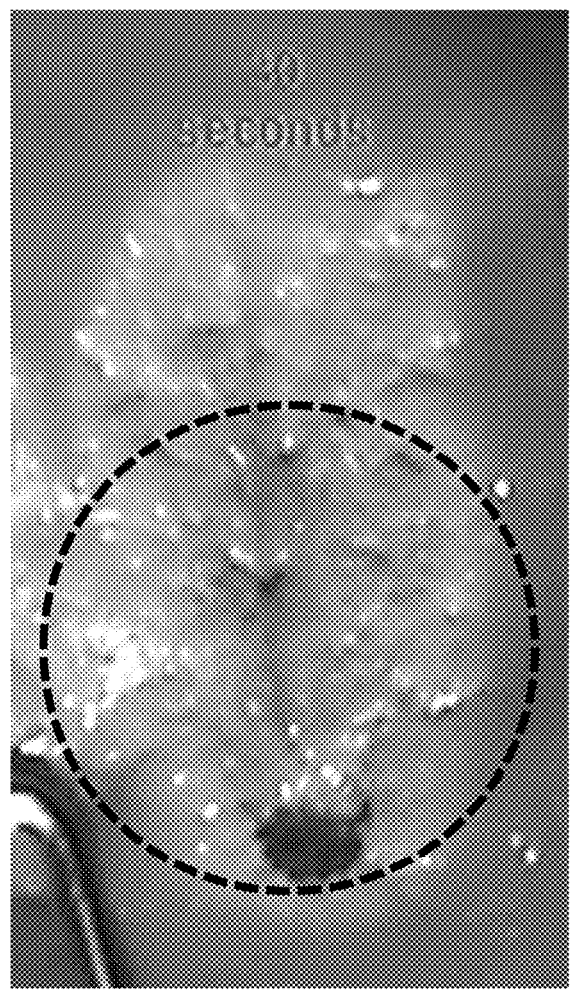
FIG. 16A is a photographic representation that shows the adverse impact of using conventional medical ablation at 2.45 GHz that results in an oblong soft tissue ablation zone.
Figure 16B:
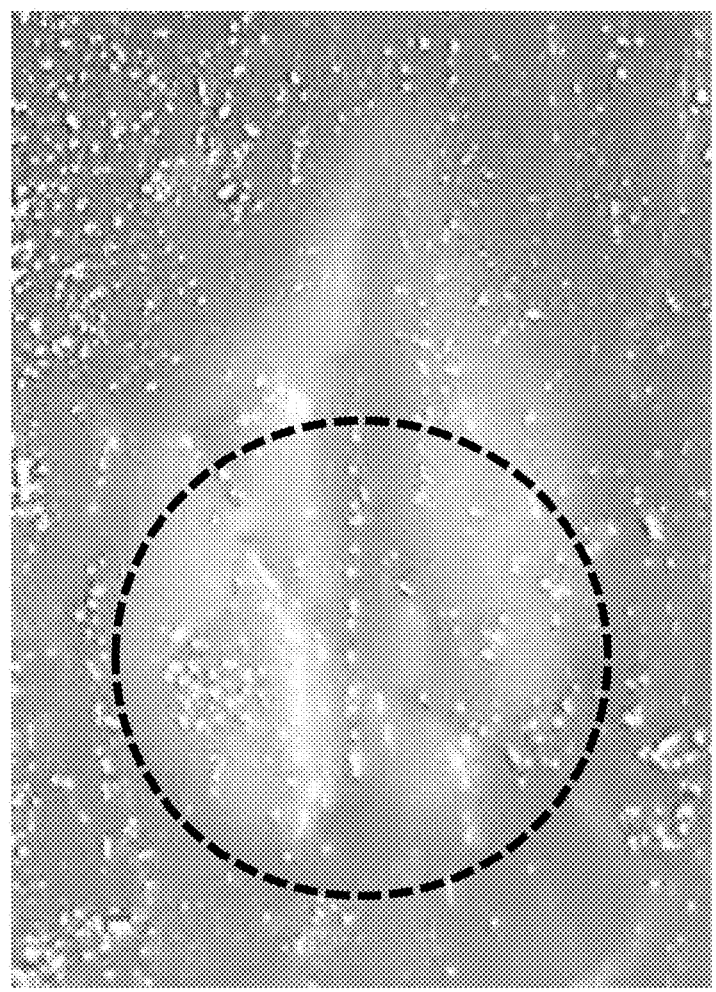
FIG. 16B is a photographic representation of that shows a zone of ablation produced at a higher frequency (8 GHz) that results in an oblong, tear-drop shaped soft tissue ablation zone.
Figure 16C:
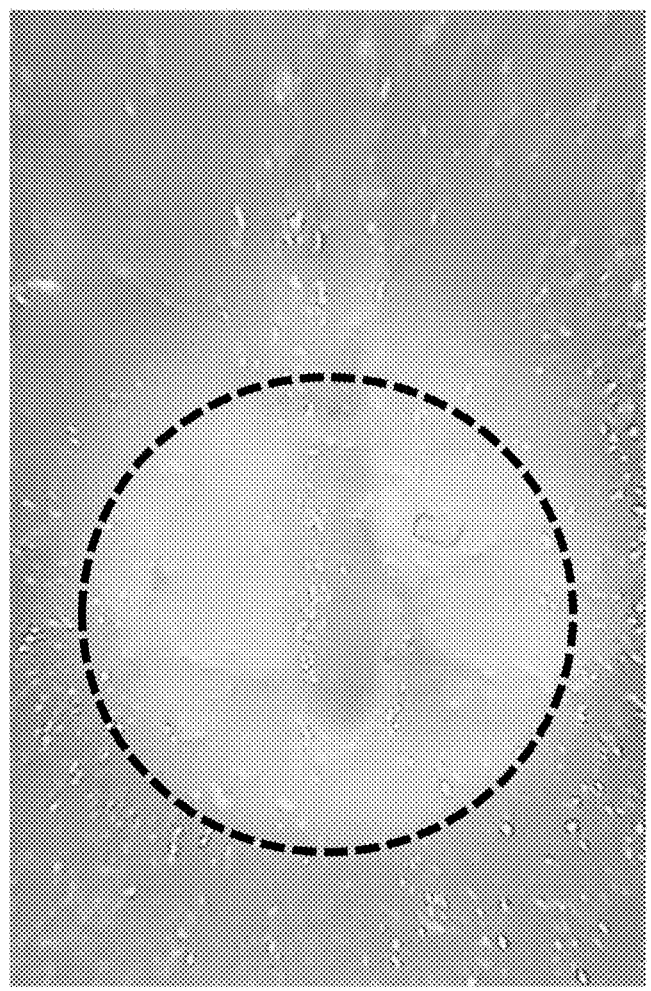
FIG. 16C is a photographic representation of that shows a spherical zone of ablation (measured at sixty degrees Celsius (60° C.)) generated using the tooth bud ablation probe described herein.
Figure 17:
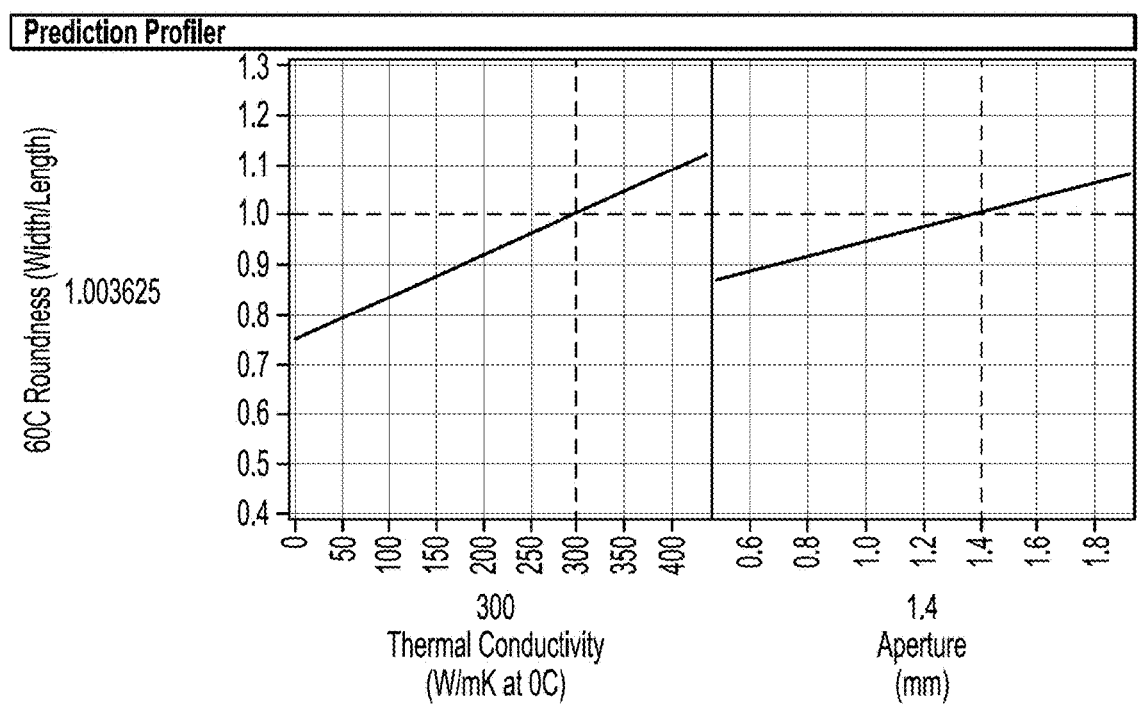
FIG. 17 shows the results of an exemplary probe experiment related to roundness at sixty degrees Celsius (60° C.).

Another ablation probe system capability described herein is "ablation zone shaping" (or "ablation zone shaping control") inside the bony crypt of the tooth. FIGS. 8-18 detail how knowing at least one profile of ablation zones 150, 160, 170 and/or the ablation probe systems 50 (and their method of use) allows the selection of the specific ablation probe tips 100 to create predetermined ablation zones that are shaped and/or sized to correspond with target tissue ablation zones. More specifically, FIGS. 8-13 show cross-sections of exemplary probe tips. FIGS. 14A-C show graphical representations of ablation probes and their respective ablation zones. FIGS. 15A-C show photographic representations of ablation probes and their respective ablation zones. FIGS. 16A-C show photographic representations of actual ablations. FIG. 17 shows the results of an exemplary probe experiment related to roundness.

Figure 11:
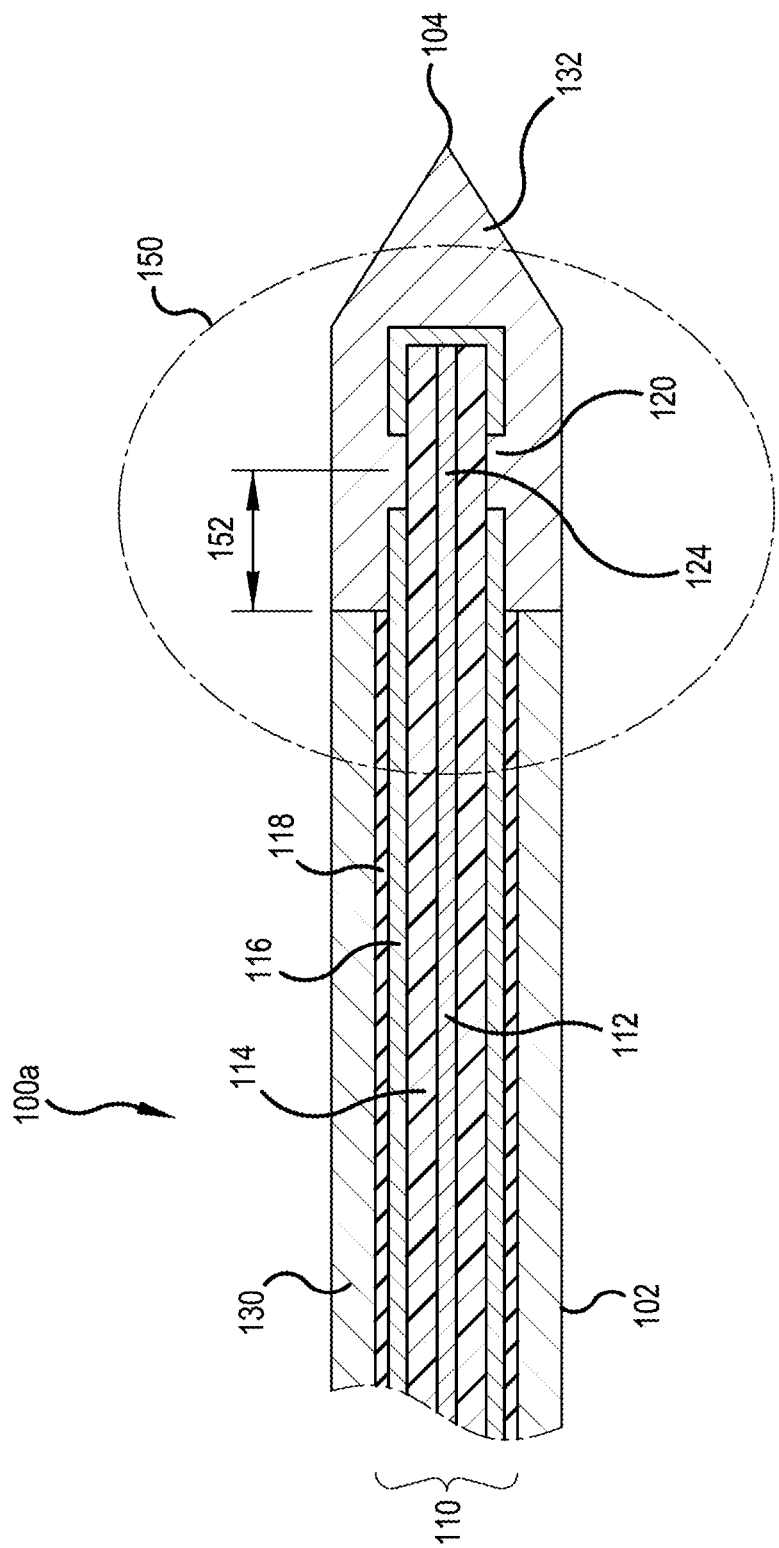
FIG. 11 is a cross-sectional view of an ablation probe and an oblate ablation zone.
Figure 12:
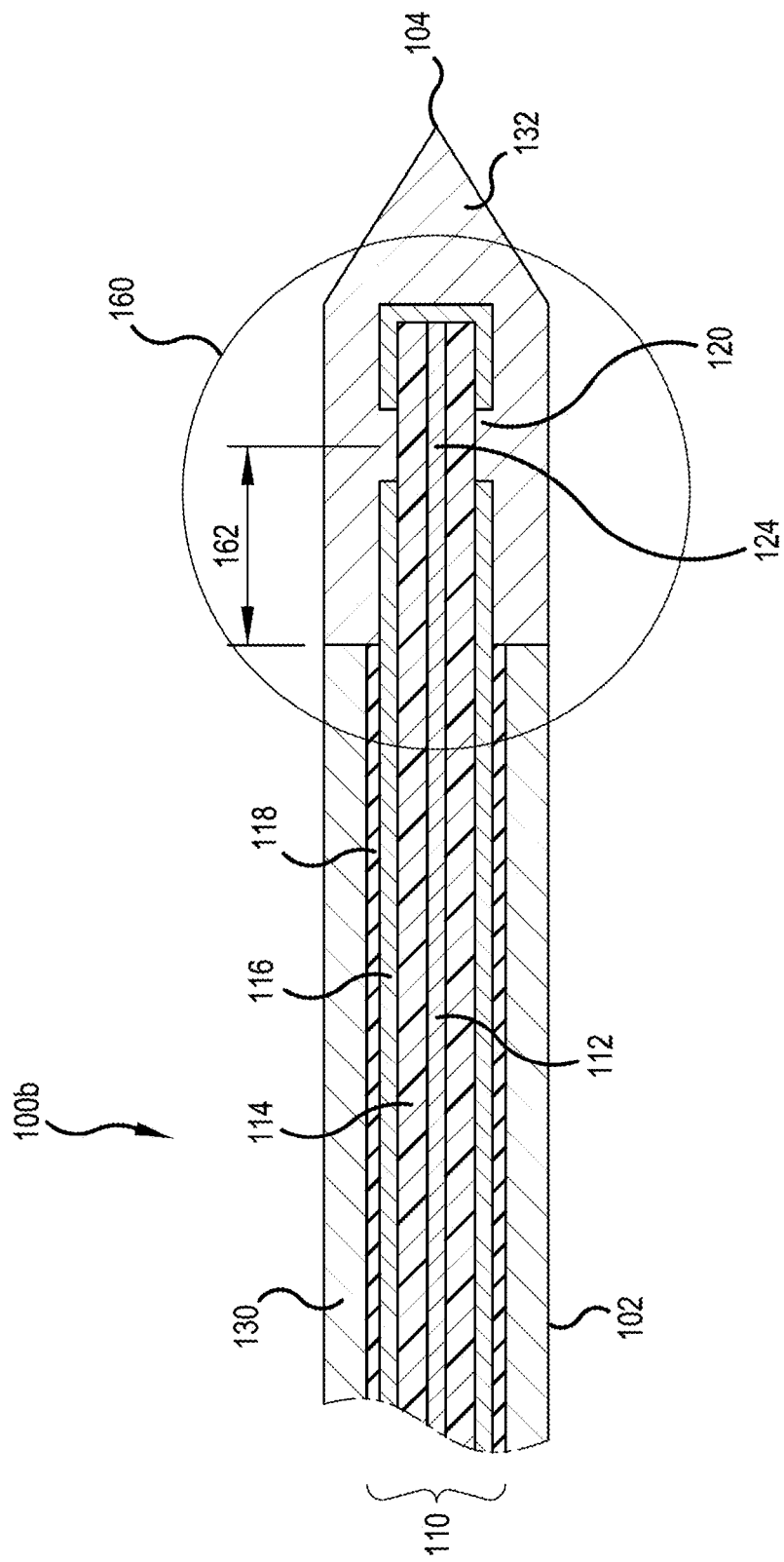
FIG. 12 is a cross-sectional view of an ablation probe and a spherical ablation zone.
Figure 13:
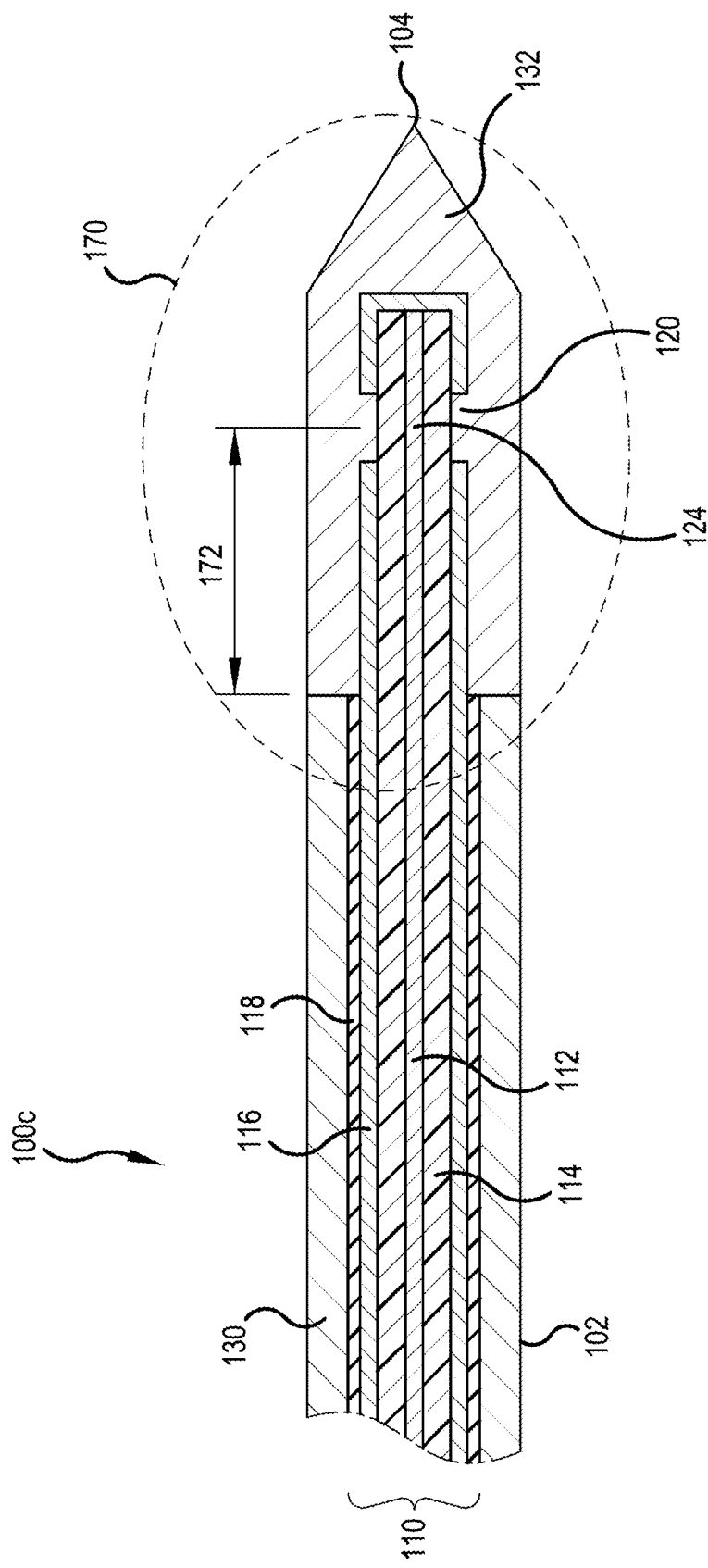
FIG. 13 is a cross-sectional view of an ablation probe and an oblong ablation zone.

FIGS. 8-13 show exemplary ablation probe tips 100 (including probe tips 100a, 100b, 100c) that are able to create ablation zones 150, 160, 170 with predetermined "shapes" and/or "sizes." For example, an ablation probe profile may specify a specific shape such as:

oblate (the longest axis of ablation zone 150 being perpendicular to the shaft 102 of the ablation probe tip 100*a*) as shown in FIG. 11, having an aspect ratio of greater than 1.0 (the oblate ablation zones 150 being wider than they are long);

spherical as shown in FIG. 12 having an aspect ratio of 1.0 (the spherical ablation zones 160 being as narrow as they are long); and/or oblong (the longest axis of ablation zone 170 being parallel and substantially coexistent with the shaft 102 of the ablation probe tip 100*c*) as shown in FIG. 13 having an aspect ratio of less than 1.0 (the oblong ablation zones 170 being narrower than they are long).

Known microwave ablation probes produce oblong ablation zones that are narrower than they are long (an aspect ratio of less than 1.0). These known oblong ablation zones can be so long they may appear to be "hot dog" shaped along the probe. The oblong ablation zones of known microwave ablation probes are at least similar to the oblong ablation zones 170 (FIG. 13) produced by ablation probe systems 50 (those used with probe tip 100*c*).

Conventional medical microwave ablation (MWA) and radiofrequency ablation (RFA) are well understood methods of inducing tissue heating that results in coagulative necrosis (cell death). Known MWA and RFA, however, generate oblong-shaped zones of ablation relative to the position of the insertion path of the ablation probe. As a result, conventional medical ablation technology was found to be suboptimal for many tooth bud ablations because the zone of ablation procedure by conventional medical ablation systems did not destroy the tooth bud tissue without also unnecessarily destroying adjacent non-tooth bud tissue. If an ablation zone of the wrong shape is used, it is almost impossible to deliver the correct amount of ablation means without unnecessarily destroying on-tooth bud tissue. For example, if the tooth bud is spherical and the ablation zone is oblong, either too much tissue will be ablated (tissue outside the tooth bud will be ablated) which will damage surrounding tissue, or too little tissue will be ablated which may result in an unsuccessful ablation. Put another way, unlike conventional medical ablation technology, the tooth bud ablation system described herein utilizes a proprietary shape zone technology for a more optimized fit inside the tooth bud that more selectively destroys targeted tooth bud tissue while destroying significantly less non-targeted tissue. Doing so greatly reduces the potential for collateral tissue damage, thus reducing the risk of adverse side effects.

FIGS. 14A-14C and FIGS. 15A-15C show representations of the heating patterns that result in the shaped ablation zones. Both the drawings of FIGS. 14A-14C and the photographs of FIGS. 15A-15C show a plurality of "isotherms" represented as a series of relatively annular lines (which can be thought of as nested rings) emanating from a relatively central region or point (an annular aperture 120 and/or a center of ablation 124 bounded by the annular aperture 120) of the tip shaft 102. Each of these isotherms represent ten degrees Celsius (10° C.) and, starting from the highest temperature in the active heating zone 125, decrease outward through thermal conduction in the thermal heating zone 126, to the outermost annular line that represents fifty degrees Celsius (50° C.). Put another way, an imaging having four nested annular lines (an example of which is shown in FIG. 23B) would mean that the first (innermost) ring represented eighty degrees Celsius (80° C.), the second ring represented seventy degrees Celsius (70° C.), the third ring represented sixty degrees Celsius (60° C.), and the fourth (outermost) ring represented fifty degrees Celsius (50° C.). Since the exemplary temperature needed for ablation of a tooth bud is sixty degrees Celsius (60° C.), the shape of the ablation zone would be based on the next to last ring (in the four ring example, the third ring). The system could be adapted to using isotherms that represent different temperatures (e.g. eight degrees Celsius (8° C.) or twelve degrees Celsius (12° C.)). Further, the system could be adapted to alternative minimum temperatures needed for ablation for different soft tissues that require higher or lower temperatures for ablation.

FIGS. 16A-16C show photos that allow a comparison of the ablated tissue from a tissue ablation that was performed using known medical ablation systems (FIGS. 16A-16B) and the medical ablation system described herein (FIG. 16C). FIG. 16A shows the adverse impact of using conventional medical ablation at 2.45 GHz. The zone of ablation in the soft tissue is highly "ragged" in appearance in the active heating zone 125, was overheated at one end, and is extremely oblong in shape as it asymmetrically migrated up the shaft of the ablation probe as the ablation probe heated up. FIG. 16B shows a zone of ablation produced at a higher frequency. It has a "tear drop" shape that asymmetrically migrated outside the spherical shape of a tooth bud that occurred because the probe shaft became too hot and is also suboptimal for tooth bud ablation. FIG. 16C shows a spherical zone of ablation generated using the tooth bud ablation probe described herein. The shape zone of ablation represents a best fit inside the soft tissue of the tooth bud and can be configured to be wider, spherical, or oblong along the path of micro-ablation probe insertion because the active heating zone 125 is predefined with thermal energy conducting out of the active heating zone 125 and into the thermal heating zone 126 in a controlled fashion.

II.A. Ablation Probe:

FIGS. 8-13 show exemplary microwave ablation probe tips 100 (which, unless specified otherwise, generically include ablation probe tip 100*a* in FIG. 11, ablation probe tip 100*b* in FIG. 12, and ablation probe tip 100*c* in FIG. 13). These ablation probe tips are designed for thermal heating of tissues. The mechanism of thermal heating occurs in an active zone of heating (ablation zone) due to highly polar water molecule vibration for microwave (MW) or ion vibration in water for radiofrequency (RF). The shown and described structure of the ablation probe tips 100 conductively transfer excess heat in the target ablation zone out of the target ablation zone into non-targeted surrounding tissue at temperatures below the threshold where tissue destruction will occur.

The shown and described structure of the ablation probe tip 100 (including the near field antenna 110—a coaxial cable with an annular aperture 120) uses "near field reactive" energy emission into the ablation zone regions and, therefore, can be considered a near field antenna. (This can be thought of as a near field reactive antenna.) "Near field reactive" regions are approximately $\lambda/2\pi \sim 0.159$ wavelengths or less in the antenna length of the ablation probe where the microwave energy is not propagating as a uniform wave. ($\lambda$ is the spatial period of a periodic wave—the distance over which the wave's shape repeats.) As described below, near field radiation regions are distinctly different from far field radiation regions where the microwave signal spreads enough that waveforms propagate as more coherent waves in the far field radiation regions.

The shown and described structure of the ablation probe tip 100 preferably delivers energy that is non-resonant in a combined aperture/ablation zone dimension that is less than the frequency wavelength divided by 4 so as to minimize production of thermal energy along the shaft 102 of the ablation probe tip 100. The optional insulation annular layer 118 may be a thermally conductive outer sheath that further minimizes production of thermal energy along the ablation probe tip 100.

Figure 8:
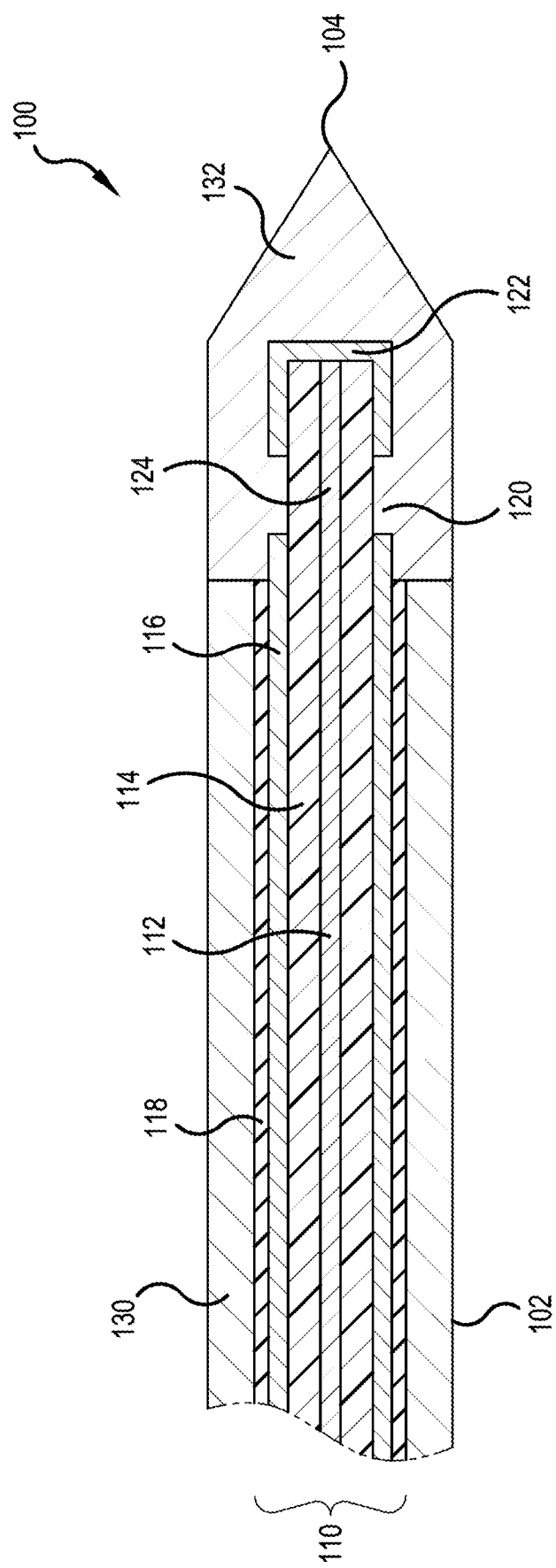
FIG. 8 is a cross-sectional view of an ablation probe.
Figure 9:
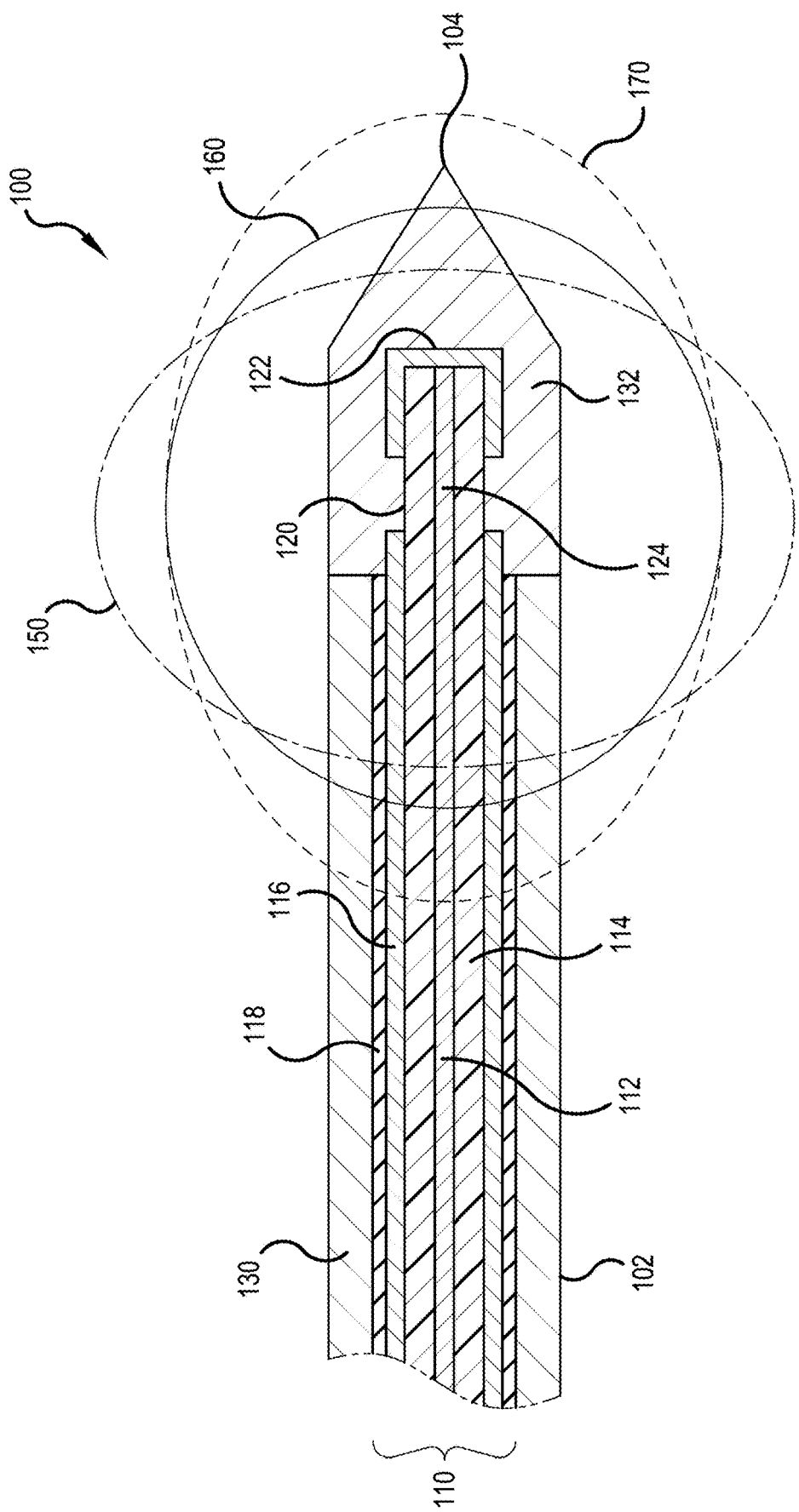
FIG. 9 is a cross-sectional view of an ablation probe and three different predetermined ablation zone shapes.
Figure 10:
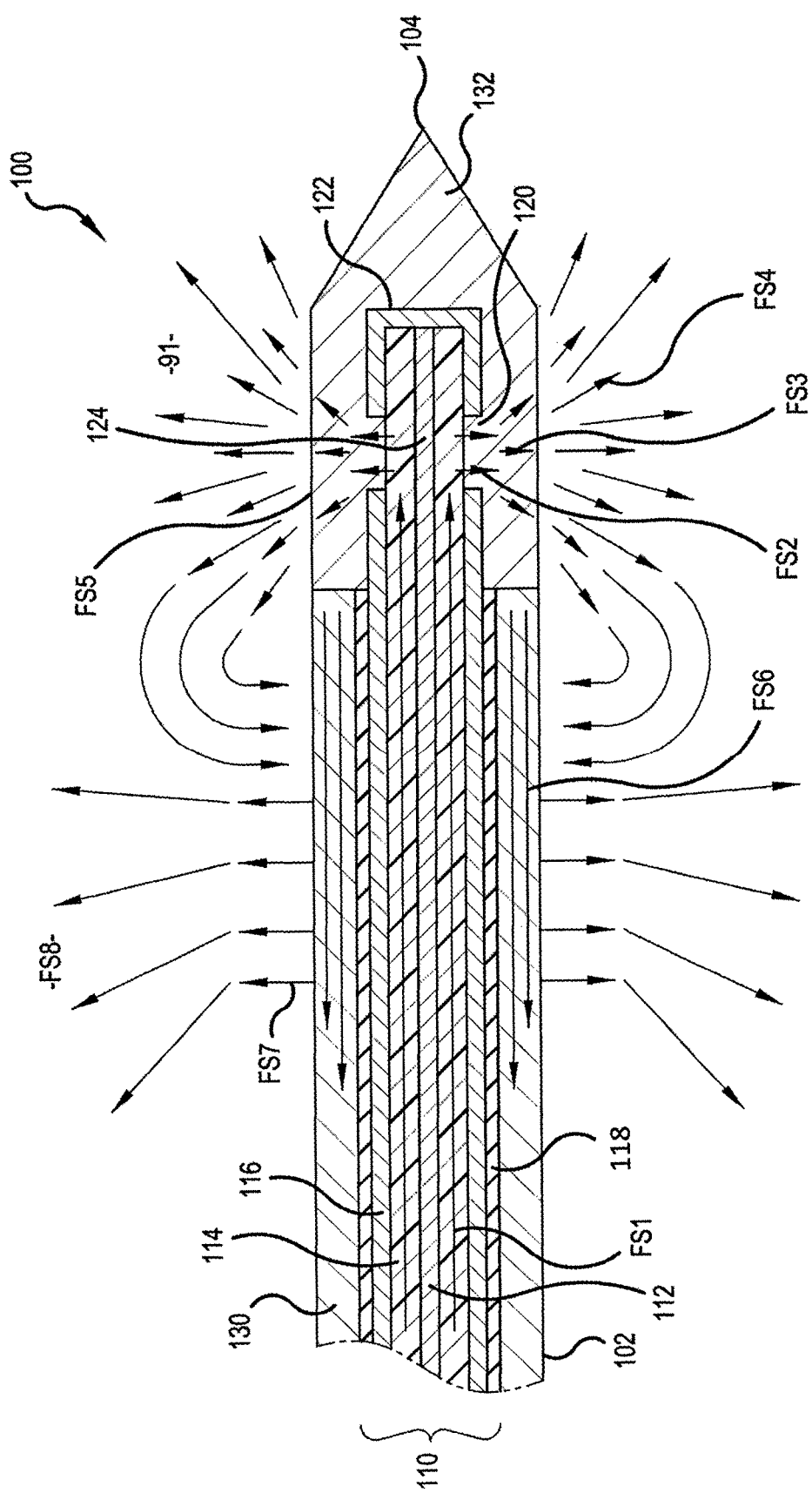
FIG. 10 is a cross-sectional view of an ablation probe and exemplary energy flow.

FIGS. 8-10 shows the shaft 102 of the ablation probe tip 100 having an insertion end 104 (also referred to as the "insertion tip," the "insertion point," and the "insertion tip point") at the end of the shaft 102. The insertion end 104 may be sharp enough to be self-introducing. The ablation probe tip 100 has a central coaxial antenna 110 (which can be thought of as a coaxial cable with an annular aperture 120). The central coaxial antenna 110 preferably includes an inner conductor 112, an annular dielectric insulator layer 114 (or other wave-guide), an annular outer conductor 116, and an optional insulation annular layer 118. Toward the end of the coaxial antenna 110 (near the insertion end 104) is an annular aperture 120 (which can be thought of as an annular window). An optional antenna end load 122 may be positioned between the aperture 120 and the insertion end 104 of the coaxial antenna 110 in order to increase the capacitive properties of the antenna to shorten the antenna center wire length, thereby making the focal region smaller (concentrating the total energy density) and increasing the power loading (power density) in the ablation zone. This will be discussed in more detail in relation to power loading control (section VI.). Surrounding the coaxial antenna 110 of shaft 102 (and spaced from the insertion end 104) is an annular heat transfer layer 130 (also referred to as a thermally conductive layer 130) and an annular tip cover 132 at the insertion end 104. The annular tip cover 132 covers and surrounds the end of coaxial antenna 110, the annular aperture 120, and the optional antenna end load 122. Further, the annular surface of the annular tip cover 132 farthest from the insertion end 104 annularly abuts the annular surface of the thermally conductive layer 130 closest to the insertion end 104.

The central coaxial antenna 110 preferably includes an inner conductor 112 annularly surrounded by an annular dielectric insulator layer 114 (e.g. polytetrafluoroethylene (PTFE), air, or other known dielectrics) that is, in turn, surrounded by an annular outer conductor 116. The inner conductor 112 may be copper, copper- or silver-plated steel, or other conductive materials. The annular dielectric insulator layer 114 may be PTFE, air, or other known dielectrics that help form a wave guide between the center wire and the annular outer conductor. The annular outer conductor 116 may be a metallic shield such as a solid or woven copper or aluminum shield or other known metals.

The coaxial antenna 110 may be purchased, pre-made, or a combination thereof (e.g. purchased without an aperture and adding the aperture later or purchased without an insulation layer and adding the insulation layer later). The antenna may be an antenna design with a capacitive load on the end (as shown) or a dipole antenna with no capacitive load or an antenna having other method of loading the end of the antenna. Even though an antenna design with an end load is shown to increase capacitive coupling to shorten the length of the antenna, a dipole antenna with no end load or other form of capacitively loading the end of the antenna to lengthen or shorten the antenna can be considered.

The ablation probe tip 100 may also include an optional insulation annular layer 118 that provides thermal and electrical isolation between the outer annular surface of the outer conductor 116 and the inner annular surface of the heat transfer layer 130. Although shown with the optional insulation annular layer 118, alternative preferred ablation probe tips could omit the insulation annular layer. The optional insulation annular layer 118 may be part of a coaxial antenna 110 (e.g. a pre-made or purchased coaxial antenna). Alternatively, the optional insulation annular layer 118 may be added to a coaxial antenna 110 (e.g. a pre-made or purchased coaxial antenna) that does not have its own insulation layer. The insulation annular layer 118 may be made of materials including, but not limited to, plastic such as polymethalmethacrylate, polysulphone, or polyetherimide or other materials, such as zirconium dioxide or lithium disilicate ceramics capable of providing electrical isolation.

Toward the end of the coaxial antenna 110 (near the insertion end 104) is an annular aperture 120 that takes the form of a 360-degree groove. Put another way, the annular aperture 120 is a portion of the coaxial antenna 110 in which the annular dielectric insulator layer 114 is free from the annular outer conductor 116. Put yet another way, the annular aperture 120 is where the annular outer conductor 116 has been removed (or was never present) in an annular ring around the exposed annular ring of the dielectric insulator layer 114. The center of ablation 124 (the focal point or region from which the ablation means radiates) is located within the inner conductor 112 at the annular aperture 120 (from which the ablation means emanates). As discussed in the center ablation control section (section III.), the ablation zones 150, 160, 170 stay centered around the annular aperture 120 and center of ablation 124 and do not symmetrically migrate up the shaft 102. When the ablation probe tip 100 is assembled, the annular tip cover 132 covers the annular aperture 120.

As set forth herein, the optional antenna end load 122 is positioned between the annular aperture 120 and the insertion end 104 of the coaxial antenna 110 and acts to increase the capacitive properties of the antenna. The optional antenna end load 122 is preferably at least substantially perpendicular and adjacent to the end of the inner conductor 112. The optional antenna end load 122 functions as a capacitive concentrator such that the ablation means "hit" the antenna end load 122 and radiates outward into the targeted tissue from a shorter effective antenna base.

The exemplary microwave ablation probe tip 100 has a shaft design with an annular heat transfer layer 130 at least partially surrounding the central coaxial antenna 110. The heat transfer layer 130 is preferably the outermost annular layer of at least the portion of the shaft 102 that it covers. As will be discussed in relation to FIGS. 11-13, the heat transfer layer 130 is positioned to create an oblate ablation zone 150, a spherical ablation zone 160, or an oblong ablation zone 170 along the shaft 102 of the ablation probe tip 100. The positioning of the heat transfer layer 130 may be predetermined or the heat transfer layer 130 may be positionable (e.g. movable, slidable, or otherwise associable at different positions) along the shaft 102, the shape of the ablation zones 150, 160, 170 being determined by the position of the heat transfer layer 130. In use, the heat transfer layer 130 partially extends into the ablation zone while part of the heat transfer layer 130 remains outside of the ablation zone. The heat transfer layer 130 is preferably made from material that both has high thermal conductivity and is electrically conductive. Put another way, the heat transfer layer 130 is preferably a high thermal conducting layer. (Preferably, the heat transfer layer 130 has high thermal conductivity and is electrically conductive.) Exemplary material includes, but is not limited to, silver (Ag), aluminum (Al), copper (Cu), stainless steel (Ss), titanium (Ti), or any other material known or yet to be discovered that has high thermal conductivity and is electrically conductive. For example, silver has higher conductivity than copper, aluminum has high conductivity (but lower conductivity than copper), stainless steel has poor thermal conductivity, and titanium has poorer thermal conductivity than stainless steel. The different thermal conduction properties of the different materials allows for the construction of devices having different measurable thermal conduction properties that can be used to create a variety of ablation probe tips for use in different applications. As discussed in ablation zone temperature control section (section IV.), preferred heat transfer layers 130 passively cool the ablation probe tip 100 by minimizing production of thermal energy along the portions of the ablation probe tip 100 substantially adjacent or near the heat transfer layer 130.

The exemplary microwave ablation probe tip 100 has a tip design with a tip cover 132 at the insertion end 104. The tip cover 132 is preferably made from material or substrate that has both high radio translucency (meaning that it is highly radiolucent or has low microwave absorption rates) and low thermal conductivity (meaning that it is highly insulating or has low thermal conduction rates) while also being electrically nonconductive. Exemplary materials suitable for this purpose include, but are not limited to plastics such as polysulphone, polyetherimide and polymethalmethacryle, but may also include ceramic substrates such as zirconium dioxide and lithium disilicate. Ablation probes with this tip design have the properties of allowing the microwave energy to escape preferentially (high radio translucency), blocking heat from returning into the ablation probe (low thermal conductivity) and high electrical isolation.

II.B. Ablation Zones:

FIGS. 8-10 show the basic components of the ablation probe tip 100 and FIGS. 11-13 show the specific ablation probe tips 100a, 100b, 100c that create the three different shaped ablation zones 150, 160, 170.

While FIG. 9 shows three different ablation zones 150, 160, 170, it incorrectly shows a single aperture offset. FIGS. 11-13 correctly show the different aperture offsets 152, 162, 172 relative to the annular outer conductor 116 that would be necessary to create the respective ablation zones 150, 160, 170.

Similarly, FIG. 10 shows exemplary energy flow of the ablation probe tip 100a of FIG. 11, but the flows would be similar for the ablation probe tips 100b and 100c of FIGS. 12 and 13. FIG. 10 shows an exemplary energy flow of an exemplary ablation probe tip 100 that can be described in eight "flow steps" (FS1-FS8). Most of the flow step reference numbers point to arrows showing the direction of energy flow. Although described as "steps" to portray flow, in reality many of the steps occur continuously and/or simultaneously. This exemplary probe tip 100 is using microwave energy as its ablation means 62.

FS1: The ablation means 62 provided by the ablation source 60 is inserted or injected into the central coaxial antenna 110 and travels down the wave-guide (e.g. dielectric insulator layer 114) between the inner conductor 112 and annular outer conductor 116.

FS2: The ablation means 62 then exits out the annular aperture 120 near the antenna end load 122. The exiting of the ablation means entails energy acting in the near field reactive region of the antenna with an effective antenna length approximately $\lambda/2\pi$ (~0.159 wavelength) or less.

FS3: The ablation means 62 next begins to radiate outward as near field radiation out of the annular aperture 120 through an annular tip cover 132. The length of the annular aperture determines the effective antenna length and effective power loading (power density), with a larger annular aperture resulting in a lower effective power density going to the targeted tissue. As set forth herein, the annular tip cover 132 has the dual properties of being highly radiolucent to out-flowing MW or RF energy while also being highly insulating so that the ablation probe tip 100 does not conduct thermal energy back in as the ablation means 62 passes through it.

FS4: After traveling through the highly radiolucent annular tip cover 132, the ablation means 62 is subsequently absorbed into the living tissue 91 (which may be a tooth bud 92 or the surrounding tissue) around the annular tip cover 132 into what will become the active heating zone 125, which starts to rapidly heat up the tissue 91 as the MW or RF energy is converted to thermal energy.

FS5: As the tissue 91 around the annular tip cover 132 increases in temperature sufficient to form the ablation zone, the low thermal conductivity/high insulating properties of the annular tip cover 132 preferably blocks the tissue's thermal energy from conducting back into the ablation probe tip's 100 antenna structure and migrating up the central coaxial antenna 110 and annular outer conductor 116.

FS6: In addition to the dual properties of the annular tip cover 132, the shaft 102 of the ablation probe tip 100 also contains an electrically and thermally isolated annular heat transfer layer 130 that blocks transmission of the ablation means 62 up the shaft 102 while allowing thermal energy from the active ablation zone to conduct preferentially up the annular heat transfer layer 130 from the soft tissue 91 zone of ablation that is heating up.

FS7: The annular heat transfer layer 130 is "quenched" by transferring its thermal energy into the contacting soft tissue 91 that is not being directly heated by the ablation means 62 because the annular heat transfer layer 130 has blocked the ablation means 62 from migrating up the shaft 102.

FS8: The mechanism of cooling the annular heat transfer layer 130 by the adjacent soft tissue 91 not only occurs through its high thermal mass due to high water content, but soft tissues 91 are perfused by moving blood, which means heat is carried away from the annular heat transfer layer 130 and out of the surrounding soft tissue 91.

The shown aperture offsets 152, 162, 172 in FIGS. 11-13 create the different ablation zone shapes 150, 160, 170. More specifically, the length to width ratio (aspect ratio) of the ablation zone increases with an increase in aperture offset to take on a more oblong shape. Aperture offsets 152, 162, 172 can be described as the distances (set backs) between the annular aperture 120 (and/or the center of ablation 124) and the annular heat transfer layer 130. For consistency, the aperture offsets 152, 162, 172 shown and described herein are the distance between the center of the annular aperture 120 (shown as the effective center of ablation 124 and also referred to as the "center of the annular aperture 124") and the annular edge of the annular heat transfer layer 130 closest to the annular aperture 120. As the center of ablation 120 is stationary (does not migrate) as discussed in the center ablation control section (section III.), the center of ablation 124 and the center of the annular aperture 124 remain the same. It should be noted that, although the distances would be different, the aperture offsets could be measured from alternative points of reference (e.g. the annular edge of the annular outer conductor 116 closest to the annular aperture 120).

The examples of FIGS. 11-13 are based on exemplary ablation probe tips with apertures 1.00 mm to 1.50 mm. The exemplary frequency used was 12 GHz and the exemplary power used was 6.6 W. (Other frequencies, including 18 GHz, were able to produce shaped ablation zones.) The range of the aperture offsets are between 0.0 mm to 3.0 mm. Measurements were taken at 20 seconds. Each probe was frequency-tuned in water to get the minimum reflected power reading prior to each ablation. (FIG. 17 shows the results of an exemplary probe experiment related to roundness of the zone ablation as it relates to both thermal conductivity of the annular outer conductor 116 and the effective aperture size 120.)

FIG. 11 shows ablation zone 150 with an oblate shape. The aperture offset 152 is the shortest of the aperture offsets 152, 162, 172 and creates the oblate ablation zone 150. As an example, for a near field probe tip, the aperture offset might be less than 1.0 mm. The ablation zone 150 has an aspect ratio of more than 1.0 (aspect ratio >1.0). FIGS. 14A and 15A show ablation zone isotherms with an exemplary oblate shape.

FIG. 12 shows an ablation zone 160 with a spherical shape. The aperture offset 162 has a length between the aperture offset 152 and the aperture offset 172 and creates the spherical ablation zone 160. As an example, for a near field probe tip, the aperture offset might be approximately 2.0 mm (or at least between 1.0 mm and 4.0 mm). The ablation zone 160 has an aspect ratio of 1.0 (aspect ratio=1.0). FIGS. 14B and 15B show ablation zone isotherms with an exemplary spherical shape.

FIG. 13 shows an ablation zone 170 with an oblong shape. The aperture offset 172 is the longest of the aperture offsets 152, 162, 172 and creates the oblong ablation zone 170. As an example, for a near field probe tip, the aperture offset might be more than 4.0 mm. The ablation zone 170 has an aspect ratio of less than 1.0 (aspect ratio <1.0). FIGS. 14C and 15C show ablation zone isotherms with an exemplary oblong shape.

As will be discussed in the calibration section and in conjunction with the CT-guided ablation volume and/or diameter control (section V.), the ablation zone shaping may be calibrated.

III. Ablation Center Control

Conventional medical microwave ablation (MWA) and radiofrequency ablation (RFA) technologies were found to be suboptimal for tooth bud ablation for a number of reasons. Medical ablation systems were reviewed and rejected because they demonstrated substantial asymmetrical "migration" of the zone of ablation up the shafts of ablation probes during the procedure. The outer margin of the soft tissue ablation zone asymmetrically migrates up the probe tip shaft as the ablation probe heats. Further, the effective center of ablation also migrates up the tip shaft as the ablation probe heats. This asymmetrical ablation zone migration makes predetermination or planning a medical ablation procedure extremely difficult for the operator and represents significant risk of damaging tissue outside the planned zone of ablation.

Figure 19:
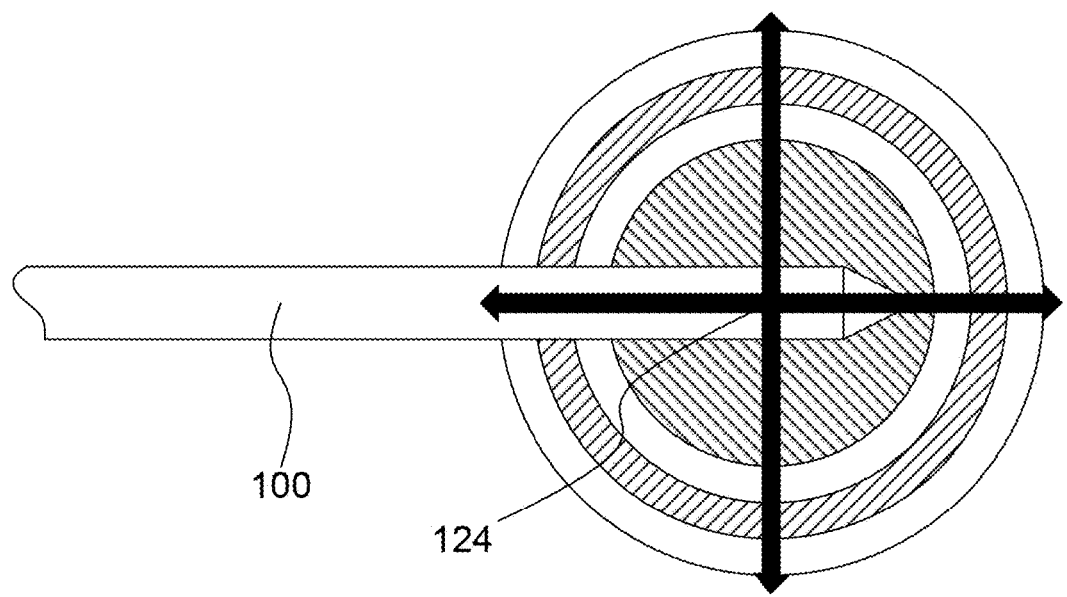
FIG. 19 is a simplified view showing an ablation probe maintaining a stationary center of ablation with no asymmetrical migration of the ablation zone up the probe tip shaft.

As set forth, the center of ablation 124 is positioned centrally within the inner conductor 112 and surrounded annularly by the annular aperture 120. The center of ablation 124 is also the effective center of the ablation zones 150, 160, 170. The center of ablation 124 is also referred to as the "center of the annular aperture 124." The micro-ablation technology described herein has been designed to eliminate asymmetrical migration of the zone of ablation up the ablation probe tip shaft during the ablation procedure. Eliminating migration can be thought of as "fixing" the center of ablation 124 in place in relation to the center of ablation 124, the annular aperture 120, and/or the ablation probe tip 100. Put another way, preferred ablation probe tips 100 described herein have "stationary" (also referred to as "fixed") ablation zones 150, 160, 170 in that they stay centered on the annular aperture 120 and the center of ablation 124. This is shown in FIG. 19. The outer margins of the ablation zones 150, 160, 170 do not asymmetrically migrate up (toward the hand piece 52) the probe tip shaft 102 as the ablation probe tip 100 heats. Further, the effective center of ablation 124 within the center of the tissue does not migrate up (toward the hand piece 52) the probe tip shaft 102 as the ablation 100 heats up.

The micro-ablation probe's annular outer heat transfer layer 130 in combination with the use of a near field antenna keeps the ablation zone's center stationary as the zone of ablation enlarges symmetrically outward, as shown in FIG. 19. As discussed in relation to FIG. 10 (FS6), the annular outer heat transfer layer 130 has dual properties: (1) it blocks transmission of the ablation means 62 from migrating up the shaft 102 and (2) it simultaneously allows thermal energy from the active ablation zone to conduct preferentially up the annular heat transfer layer 130 from the soft tissue 91 zone of ablation that is heating up.

Once the micro-ablation probe tip 100 is positioned inside the target tissue 92, the ablation procedure is activated by the operator through use of the ablation source 60. The ablation means 62 flows through the ablation probe system 50 and radiates outward from the center of ablation 124. The energy/heat radiating outward from the center of ablation 124 forms the ablation zones 150, 160, 170. While energy is radiating outward from the center, the center of ablation 124 and the ablation zones 150, 160, 170 remains stationary in relation to the center of ablation 124 in that the ablation zones 150, 160, 170 stay centered about the center of ablation 124 and the outer margins of the ablation zones 150, 160, 170 do not migrate up the probe tip shaft 102 as the ablation probe tip 100 heats. Instead, properties of the near field antenna 110 (the central coaxial antenna 110) and/or the properties of the annular outer heat transfer layer 130 prevent the upward migration (away from the insertion end 104) in relation to the shaft 102. This is true regardless of whether the shape of the ablation zone is oblate, spherical, or oblong.

There is no known competing technology that has this unique capability to maintain the zone of ablation in a fixed position throughout an ablation procedure and, therefore, no other medical ablation technology has this degree of centering capability.

IV. Ablation Zone Temperature Control

Another aspect of the tooth bud ablation process is ablation zone temperature control. The peak temperature is limited throughout the procedure in order to prevent tissue charring. A comparison between over-heated tissue and properly heated tissue can be seen by comparing FIGS. 20A and 20B.

Figure 20A:
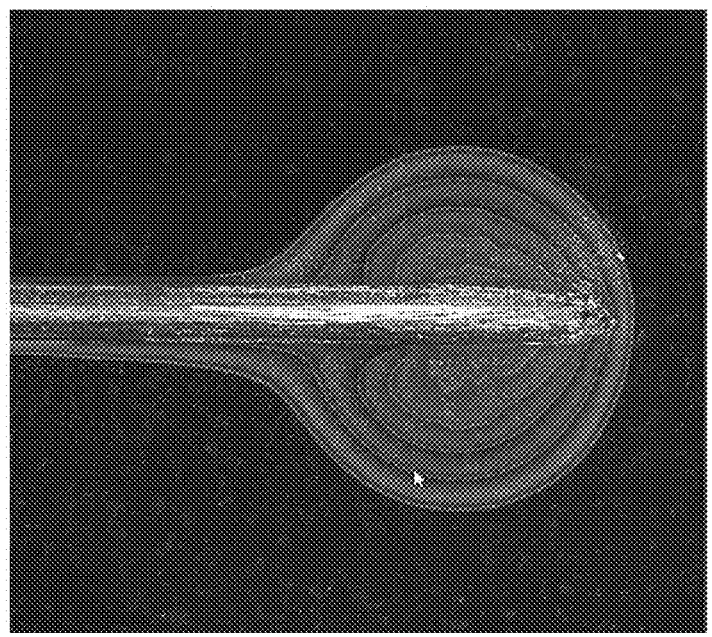
FIG. 20A is a photographic representation of an ablation probe with the center of soft tissue ablation generating temperatures in excess of one hundred degrees Celsius (100° C.), the steam generated as a result shown as the wavy rings.

FIG. 20A shows over-heated tissue which can be seen as steam generated (shown as the wavy inner ring) in the center region in the active heating zone 125 around the probe tip. This would occur when the peak temperature exceeded one hundred degrees Celsius (100° C.). Steam generation dehydrates the tissue, which may lead to tissue charring and abnormal healing that includes residual scar formation. Put another way, failure to control the peak temperature may result in unpredictable healing that may lead to scarring. When scarring formation occurs, then it is possible that the soft tissue will not heal normally.

Figure 20B:
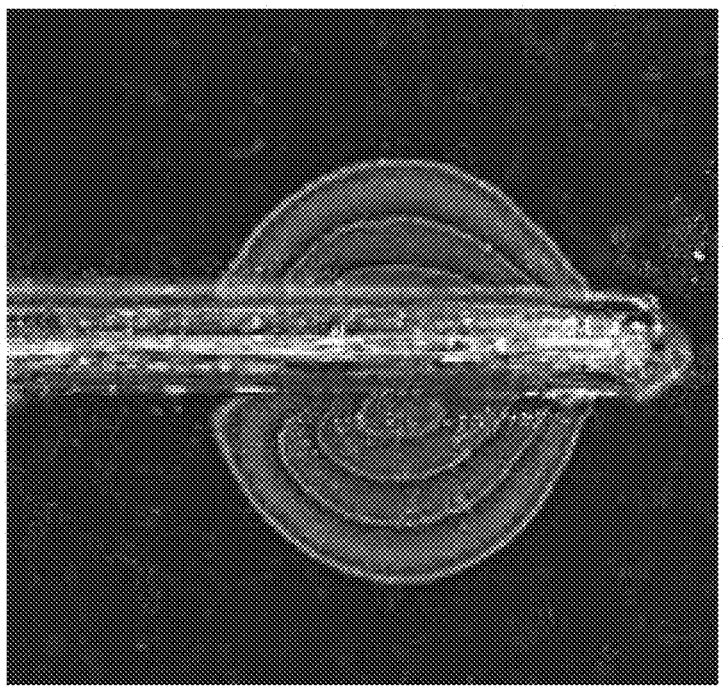
FIG. 20B is a photographic representation of an ablation probe with the center of soft tissue ablation generating temperatures remaining below one hundred degrees Celsius (100° C.), the rings being more regular since no steam is present.

FIG. 20B shows properly heated tissue in which a temperature-controlled ablation process does not exceed ninety degrees Celsius (90° C.). There is little potential for dehydration of the tissue during ablation or abnormal post-op healing with radiographically detectable scar formation when peak temperatures do not exceed one hundred degrees Celsius (100° C.). Based upon multiple animal studies, when peak temperatures are limited to ninety degrees Celsius (90° C.), the bone infills in a short period of time and the tooth buds are no longer detectable on X-rays in just four (4) weeks. Keeping the peak temperatures to ninety degrees Celsius (90° C.) or below, therefore, is highly desirable.

There are two main types of temperature control that may be used in the ablation probe system: "passive" cooling and "active" cooling. Temperature is also affected by the power loading control as discussed in the power loading section (section VI.).

IV.A. Passive Cooling:

Preferred ablation probe tips 100 (including the probe tip shaft 102) described herein include passive cooling (passive ablation zone temperature control). For passive cooling, heat transfer layers 130 passively cool the ablation probe tip 100 by minimizing production of thermal energy along the portions of the ablation probe tip 100 substantially adjacent or near the heat transfer layer 130. The passive cooling of preferred ablation probe tips 100, therefore, keeps the probe tip shafts 102 relatively cool.

Ablation probe tips 100 described herein use the thermal properties of the adjacent living tissue 91 (the specific thermal mass of the soft tissue 91 and the active blood perfusion of the soft tissue 91) to cool the ablation probe tip 100 and help shape the ablation zones 150, 160, 170. This feature can be referred to as "tissue quenching." Tissue quenching is shown in FIG. 10 (flow steps FS7 and FS8) which is discussed herein.

IV.B. Active Cooling:

It should be noted that many known microwave ablation probes require active cooling of some sort (e.g. active pumping of liquid coolant (such as water) or gas (such as $CO_2$) along the probe tip shaft or else the shaft super-heats and charring of tissue along the shaft occurs with local temperatures sometimes exceeding 300° C. Preferred ablation probe tips 100 described herein that create ablation zones less than 25.0 mm in diameter, however, may not require active cooling to keep the probe tip shaft 102 from getting so hot that tissue 91 is ablated along the probe tip shaft 102.

Some preferred ablation probe tips 100 described herein may also include optional active cooling for ablation zones. In active ablation zone temperature control, feedback from the ablation source 60 and/or from the ablation probe tip 100 (which may have at least one sensor 108 along the shaft 102 to monitor, for example, temperature) may be provided to the user (or to electronic or digital monitoring systems that may be implemented by software) using an output mechanism 68 such as a video display or audio display (speaker).

For the ablation probe systems 50 described herein, exemplary optional active cooling 54 (which includes cooling materials such as liquid coolant (such as water) or gas (such as $CO_2$)) may be provided via the hand piece 52 and/or directly to the ablation probe tip 100. Using the probe 100 in FIG. 8, the cooling 54 may flow between the annular outer conductor 116 and the heat transfer layer 130. If an optional insulation annular layer 118 is present, the cooling 54 could flow either inside or outside of the optional insulation annular layer 118. Alternatively, the cooling 54 could travel through channels and openings (not shown) incorporated in or through the heat transfer layer 130.

There are four variables that can be controlled that relate at least tangentially to temperature control (active cooling): power/temperature, frequency/penetration, time/size, and shape/roundness.

Power/Temperature: The power is kept low to prevent the maximum temperature from rising above ninety degrees Celsius (90° C.).

Frequency/Penetration: The frequency is selected to penetrate further into the tissue (i.e. there is less need for conduction and higher temperature).

Time/Size: The size of the ablation zone may be determined by the duration of the ablation process (typically 20 to 40 seconds). In addition to controlling the total time of the duration of the ablation, modulating the energy on and off in a controlled fashion (pulse width modulation) is part of the time control.

Shape/Roundness: The shape/roundness of the ablation zones 150, 160, 170 is determined by the design of the ablation probe tip 100 including, for example, the size of the aperture offset (e.g. aperture offsets 152, 162, 172).

These variables, however, can be intertwined. For example, a large ablation zone (time/size) may take longer to heat (power/temperature) than a small ablation zone. Pulse width modulation of the time/energy may also improve the degree to which a zone of ablation becomes more oblate. The combination of the variables is generally controlled by the ablation source 60 which may be controlled manually (regular) and/or automatically (smart). At least an initial set of parameters for the variables may be part of a prescription (in a surgical kit) that is input (programmed) into the ablation source 60. The combination of the variables is based on an empirical map (developed based on extensive testing) and/or using at least one sensor that provides feedback.

An empirical mapping of the ablation process shows the maximum temperature and temperature gradients are based on total energy/power and frequency. Empirical testing may be used, for example, to determine the maximum energy input (power) as a function of time. After conducting extensive testing and mapping out the maximum temperatures, over heating may be avoided by controlling the variables (e.g. controlling power input).

Alternatively, or in conjunction with empirical testing, at least one external temperature sensor may be placed on or in the surface of the ablation probe 100. Having precise energy (power) delivery control with feedback from at least one sensor can be a key component to temperature control. There are a number of fiber optic-based temperature sensors that do not interfere with the microwave energy emission including, for example, fiber optic temperature sensor solutions from OSENSA Innovations (Burnaby, BC, Canada). The temperature feedback from at least one fiber optic sensor can be provided to (coupled into) the ablation source 60 to adjust and maintain a targeted temperature.

Feedback may be provided as input to the ablation source 60. Feedback may be provided to the user using an output mechanism 68 such as a video display or audio display (speaker). The user could then manually adjust the parameter settings 64 and the treatment time settings 66 (including stopping the treatment) of the ablation source 60. Feedback may also (or in the alternative) be provided directly to an output mechanism 68 (e.g. a smart generator) (or to electronic or digital monitoring systems associated therewith that may be implemented by software associated with the ablation source 60) that automatically adjusts the parameter settings 64 and the treatment time settings 66.

V. Guided Ablation Volume and/or Diameter Control

Ablation volume control is another aspect that can be instrumental in procedural success. To this end, the ablation source 60 (e.g. a "smart" micro-ablation generator) precisely delivers prescribed ablation zone volumes. The ablation zone volumes are determined pre-operatively through volume scan imaging and provided as a prescription along with parameters of the relative variables (e.g. time and power). The ablation source 60 preferably controls the energy delivery (e.g. rate and time) to generate the prescribed ablation zone volume inside the bony crypt of the tooth bud. This allows the system to deliver ablation zone margins +/−0.5 mm (within statistical limitations) for the prescribed ablation. This technology has the unique capability of being able to predetermine and deliver the final diameter and ablation volume with this degree of precision.

Figure 21:
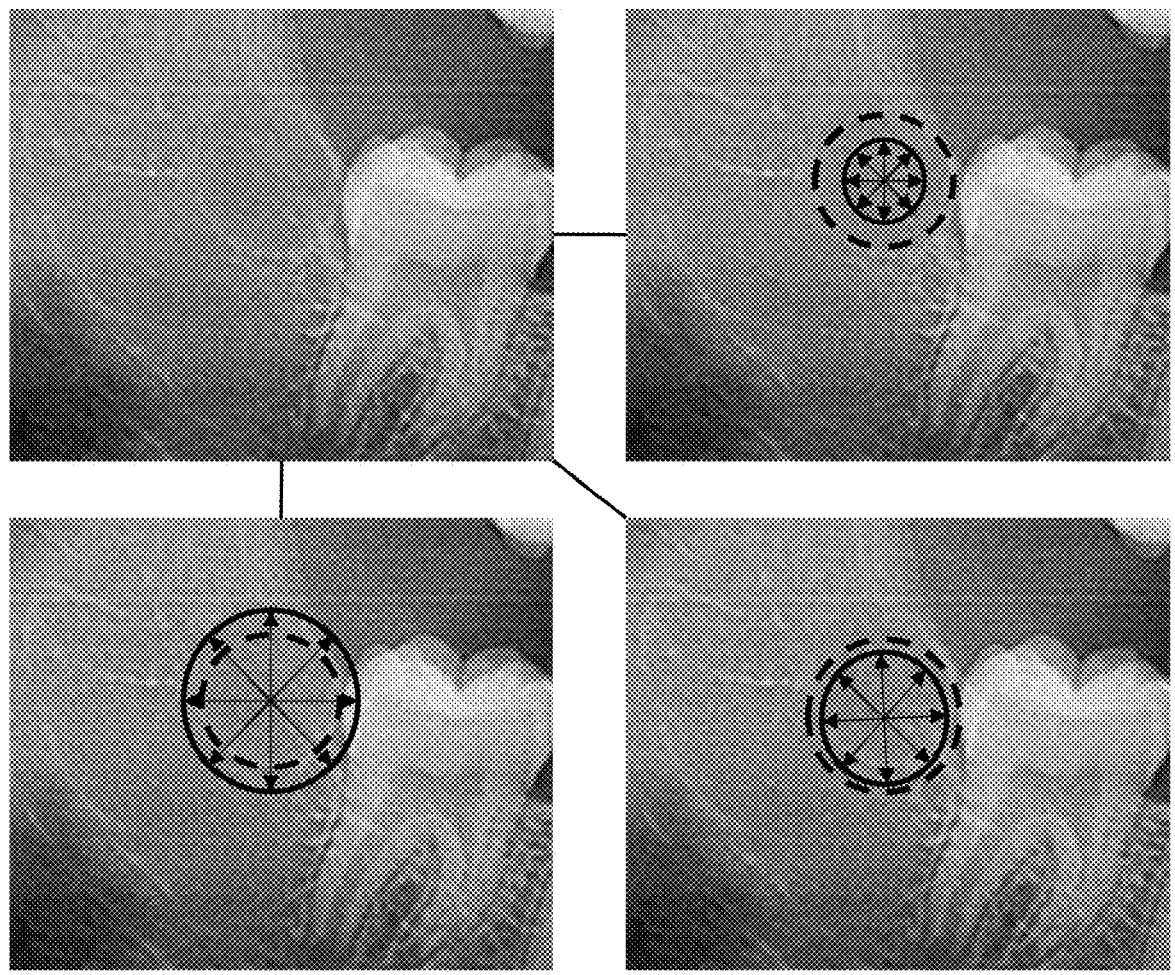
FIG. 21 is a photographic representation that shows an under ablation-zone, a correct ablation zone, and an over-oblation zone.

FIG. 21 shows four images: an original image (top left) and three images (top right, bottom left, and bottom right) with marking thereon. The top left image is of the targeted tooth bud. The three marked drawings each include a dashed line circle that represents the tooth bud. The three marked drawings also include a solid-line circle with arrows radiating from the center to the interior perimeter of the solid-line circle that represents the ablation zone. The top right image shows the tooth bud under-ablated because the ablation zone is significantly smaller than the tooth bud. The bottom left image shows the tooth bud over-ablated because the ablation zone is larger than the tooth bud. The bottom right image shows the tooth bud correctly ablated because the ablation zone is a relatively tight fit (the annular distance between the ablation zone within the tooth bud may be a bit exaggerated) to the tooth bud.

Using the prescription from the volume scan guided procedure, the ablation means 62 (e.g. the "smart" microwave generator) controls energy delivery (both rate and time) to generate the prescribed ablation zone volume inside the bony crypt of the tooth bud once the ablation probe is in the correct position.

Figure 22:
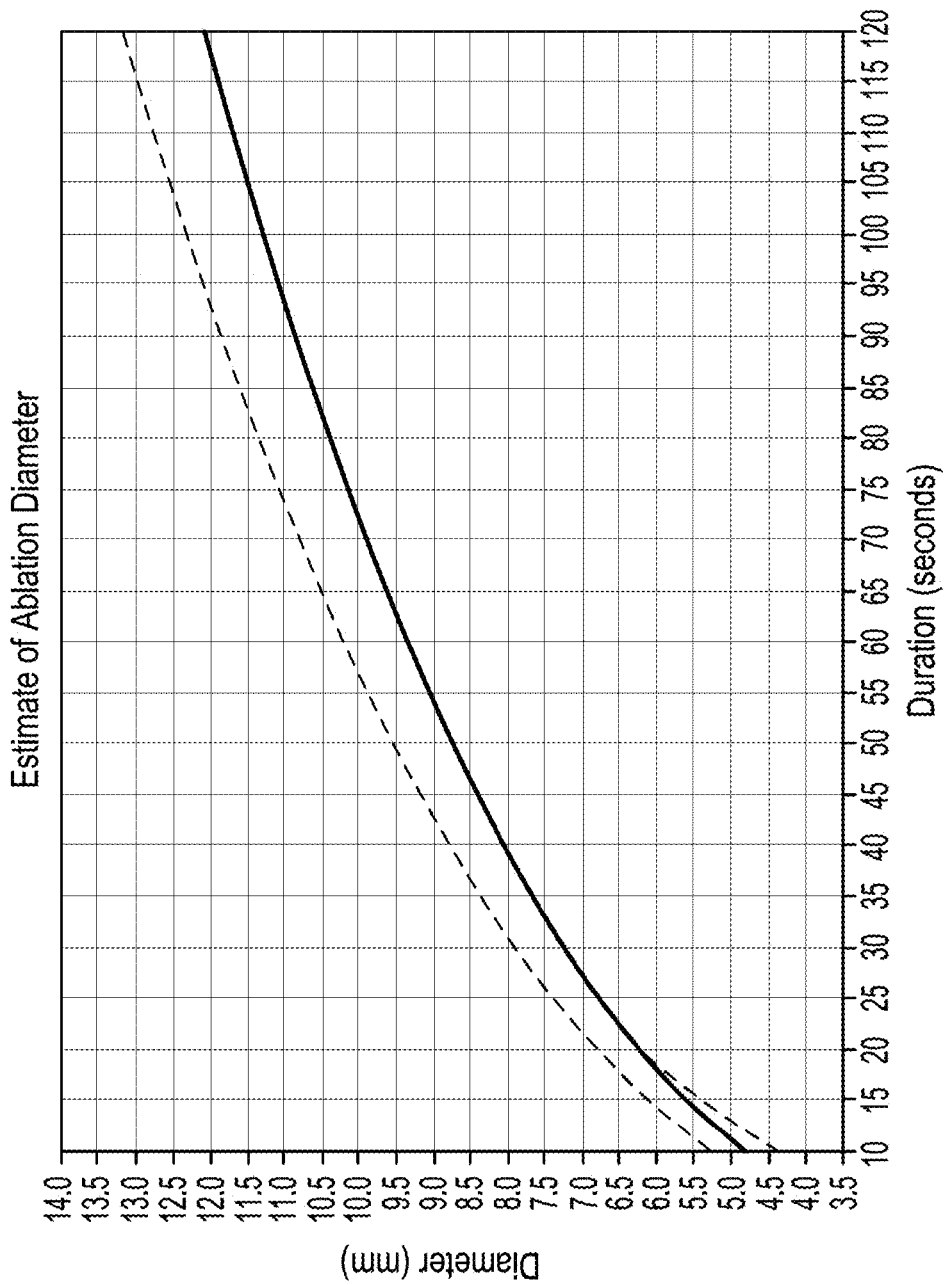
FIG. 22 shows the results of an exemplary probe experiment correlating ablation zone diameter (in mm) to ablation duration (in seconds).

Extensive experiments were performed both on tooth buds (ex vivo) and on pork loin to determine the estimated duration required for variation ablation diameters. The results of the experiments were analyzed and the graph in FIG. 22 and the table below show some of the results. In the FIG. 22 graph, the solid line shows the diameter estimates for ablations in tooth buds for various durations. The dashed line above the solid line shows diameter estimates for ablations in pork loin. The chart below adds the additional variable of the specific diameter that would represent the bony crypt diameter along with a correlation of ablation duration to the estimated diameter of the ablation zone.

| Ablation Duration Table For In Vivo Pig Ablations | | |
|---|---|---|
| Largest Bony Crypt Diameter Measured in CT Image (mm) | Ablation Duration (seconds) | Estimated Ablation Zone Final Diameter (mm) |
| 4.0 to 4.5 | 20 | 6.2 |
| 4.6 to 5.0 | 25 | 6.8 |
| 5.1 to 5.5 | 30 | 7.2 |
| 5.6 to 6.0 | 40 | 8.0 |
| 6.1 to 6.5 | 45 | 8.4 |
| 6.6 to 7.0 | 55 | 9.0 |
| 7.1 to 7.5 | 65 | 9.6 |
| 7.6 to 8.0 | 75 | 10.1 |
| 8.1 to 8.5 | 85 | 10.6 |
| 8.6 to 9.0 | 95 | 11.1 |
| 9.1 to 9.5 | 110 | 11.7 |

VI. Power Loading Control

As set forth herein, the length of the annular aperture (and the size of the focal region therein) determines the effective antenna length and/or effective power loading (also referred to as "power density" and "power loading density"). Compared to larger annular apertures, smaller annular apertures produce relatively higher effective power densities in the targeted tissue's active heating zone 125. Compared to smaller annular apertures, larger annular apertures produce relatively lower effective power densities going to the targeted tissue's active heating zone 125. Because the size of the annular apertures can be controlled and/or predetermined, the power loading densities can be controlled and/or predetermined (a predetermined power loading density).

As set forth herein, the length of the annular aperture (and the size of the focal region therein) determines the effective peak temperatures in the active heating zone 125. Compared to larger annular apertures, smaller annular apertures produce relatively higher effective peak temperatures in the active heating zone 125. Compared to smaller annular apertures, larger annular apertures produce relatively lower effective peak temperatures in the active heating zone 125. Because the size of the annular apertures can be controlled and/or predetermined, the peak temperatures in the active heating zone 125 can be controlled and/or predetermined to be high peak temperatures, medium peak temperatures, low peak temperatures (a predetermined peak temperature). The peak temperatures are relative to other ablation probe tips and systems having the same parameters and/or variables.

As set forth in the ablation probe section (section II.A.) of the ablation zone shaping control section (section II.), an antenna end load 122 near the aperture 120 of the coaxial antenna 110 increases the capacitive properties of the antenna 110 to shorten the antenna center wire length. This makes the focal region 124 smaller (concentrating the energy density) and increases the power loading (power density) in the ablation zone 150, 160, 170 (shown in FIGS. 23A-23C as ablation zones 160a, 160b, 160c, which are variations of the spherical ablation zone 160). There are other ways to change (increase/decrease) the size of the focal region 124 including, but not limited to, antenna designs that use pigtail and other known techniques and technology used to add end loads to increase antennas' power loading.

FIGS. 23A-23C and FIGS. 24A-24C are graphic and photographic images that show the effect that the size of the focal region (the center of ablation 124 bounded by the annular aperture 120 (shown as 120a, 120b, 120c in FIGS. 23A-23C) has on the creation of ablation zones 150, 160, 170 (although only the approximately spherical ablation zone 160 is shown). Other than the size of the annular aperture 120, the variables (e.g. time, power, and so forth) in the experiments documented by these photographs remained constant. The rings on these photographs are like the rings in FIGS. 15A-15C in that the isotherms (annular lines) surrounding the focal region each represent ten degrees Celsius (10° C.) and the outermost isotherm (annular line)

represents fifty degrees Celsius (50° C.). Exemplary isotherms are labeled in FIGS. 23A-23C.

The rate of heating (delta temperature/delta time) increasing as the annular aperture gets smaller can be shown mathematically. Power density can be thought of as the amount of power (time rate of energy transfer) per unit volume. In this equation (and an example only), the amount of power is expressed in watts (W) and the unit volume is expressed in cubic millimeters ($mm^3$). If 5.0 W of microwave energy were applied to a probe tip with an annular aperture that is 1.0 mm long, the power density would be approximately 5.0 $W/mm^3$. If 5.0 W of microwave energy were applied to a probe tip with an annular aperture that is 4.0 mm long, the power density would be approximately 1.25 $W/mm^3$.

Figure 24A:
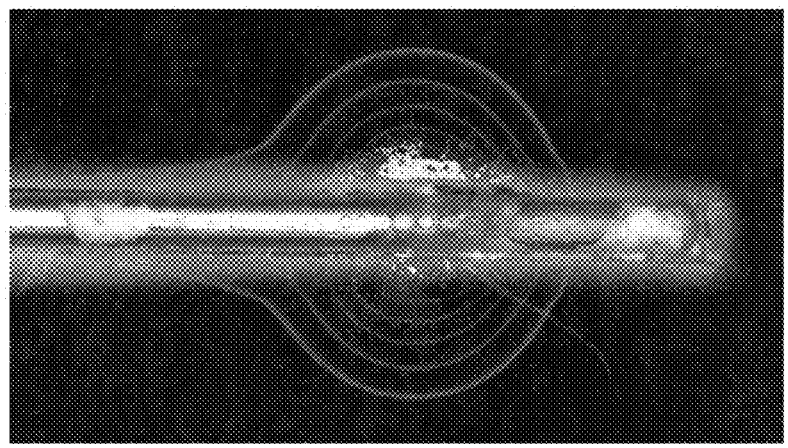
FIG. 24A is a photographic representation of an ablation probe with a small focal region creating high power loading in the ablation zone.

The ablation probe shown in FIG. 24A has a small focal region that creates high power loading density in the ablation zone 160*a*. More specifically, the focal region is a 0.8 mm (length along the probe shaft) annular aperture 120*a*. If 5.0 W of microwave energy were applied to this probe tip, the power density would be approximately 6.25 $W/mm^3$ as the microwave energy first begins to enter the tissue. The inner peak ablation zone temperature in the active heating zone 125 is ninety degrees Celsius (90° C.). FIG. 23A shows a similar probe tip 100 that creates a spherical ablation zone 160*a* (although other shapes could be created using probes with shorter or longer aperture offsets) with an active heating zone 125 and a thermal heating zone 126. The short annular aperture 120*a* bounds a short/small focal region 124 that, in turn, results in a short/small zone of active heating that creates high power loading (represented by the relative closeness (tight spread) between isotherms in the thermal heating zone 126 of the ablation zone 160*a*).

Figure 24B:
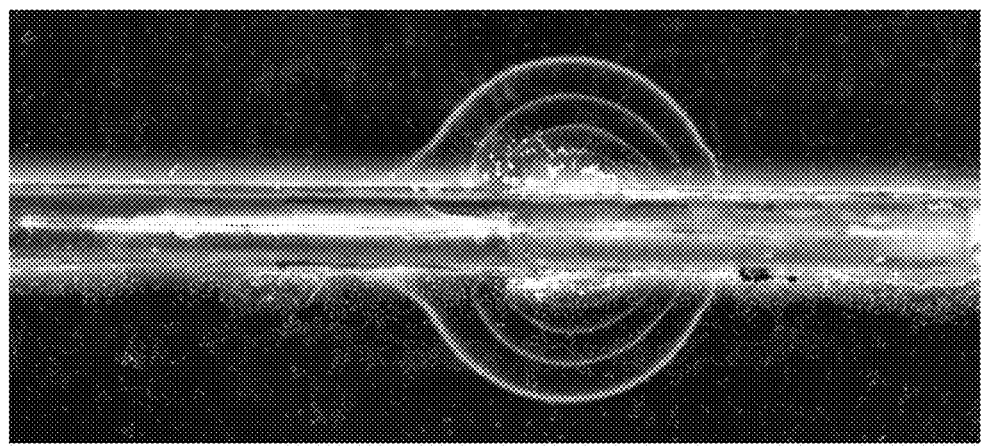
FIG. 24B is a photographic representation of an ablation probe with a medium focal region creating medium power loading in the ablation zone.

The ablation probe shown in FIG. 24B has a medium focal region that creates medium power loading density in the ablation zone 160*b*. More specifically, the focal region is a 1.5 mm (length along the probe shaft) annular aperture 120*b*. If 2.4 W of microwave energy is applied to this probe tip, the power density would be approximately 3.3 $W/mm^3$ as the microwave energy first begins to enter the tissue. The inner peak ablation zone temperature in the active heating zone 125 is eighty degrees Celsius (80° C.). FIG. 23B shows a similar probe tip 100 that creates a spherical ablation zone 160*b* (although other shapes could be created using probes with shorter or longer aperture offsets) with an active heating zone 125 and a thermal heating zone 126. The medium annular aperture 120*b* bounds a medium focal region 124 that, in turn, results in a medium length/size zone of active heating that creates medium power loading (represented by the intermediate spread isotherms in the thermal heating zone 126 of the ablation zone 160*b*).

Figure 24C:
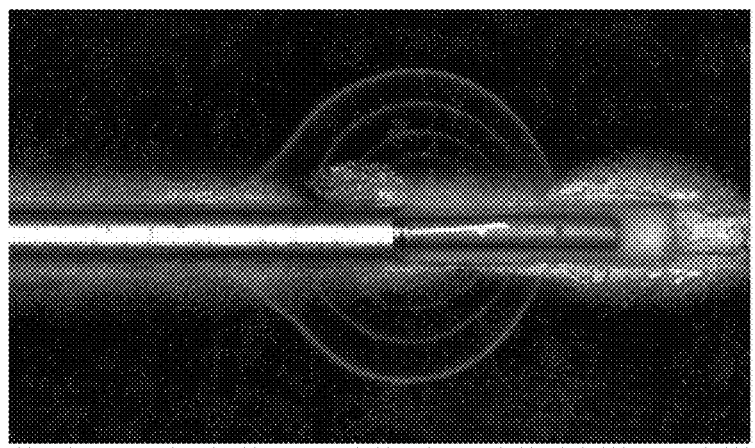
FIG. 24C is a photographic representation of an ablation probe with a large focal region creating low power loading in the ablation zone.

The ablation probe shown in FIG. 24C has a large focal region that creates low power loading density in the ablation zone 160*c*. More specifically, the focal region is a 4.0 mm (length along the probe shaft) annular aperture 120*c*. If 2.4 W of microwave energy is applied to this probe tip, the power density would be approximately 1.25 $W/mm^3$ as the microwave energy first begins to enter the tissue. The inner peak ablation zone temperature in the active heating zone 125 is seventy degrees Celsius (70° C.). FIG. 23C shows a similar probe tip 100 that creates a spherical ablation zone 160*c* (although other shapes could be created using probes with longer or longer aperture offsets) with an active heating zone 125 and a thermal heating zone 126. The long annular aperture 120*c* bounds a long/large focal region 124 that, in turn, results in a long/large zone of active heating that creates low power loading (represented by the relatively large distance (wide spread) between isotherms in the thermal heating zone 126 of the ablation zone 160*c*).

Power density is one of the capabilities of an ablation probe tip 100 that would be relevant for calculations performed, for example, by software. Selecting an ablation probe tip 100 with an annular aperture 120 of a known or predetermined length will produce an ablation zone 150, 160, 170 with a known or predetermined power loading. The ablation probe tip 100 with the predetermined-sized annular aperture 120 may be included in a surgical kit or the prescription may specify ablation probe tip 100 with the predetermined-sized annular aperture 120 to be used in the procedure.

As a point of clarity, it should be noted that the power density is at least substantially independent from the shape of the ablation zone 150, 160, 170. Whereas the power density is related to the size of the annular aperture 120, the shape of the ablation zone 150, 160, 170 is related to the aperture offsets 152, 162, 172.

Calibration

The ablation probe systems 50 are preferably calibrated. This may be accomplished by performing a plurality of ablations (e.g. 150 ablations in tooth bud tissue from freshly harvested mandibles and maxillas of sacrificed animals) and using the results to establish a "calibration curve" based upon the resulting ablation of the tissue.

A volume scan is taken of the target tissue. This image may be used to determine, for example, the volume/diameter of the zone of ablation, the shape of the zone of ablation, and/or the position of the zone of ablation.

After the diameter of the bony crypt of each tooth bud is measured, a "best fit" ablation zone may be created, for example, by selecting an ablation probe tip 100 and the system settings based upon an ablation probe system's actual ablation volume properties. Put another way, a probe with known predetermined three-dimensional ablation profile is used. The size and shape of the ablation probe tip 100 is also relevant, as it would relate to the positioning provided by the custom surgical stent 80. Finding the "best fit" would preferably include determining that the volume/diameter of the zone of ablation is adjusted to fit the individual tooth buds. Further, finding the "best fit" would preferably include determining that the shape of the zone of ablation is adjusted to fit the individual tooth buds. Put another way, the ablation zone shape is preferably controlled to fit inside the tooth bud. (For example, if the tooth bud is oblong, then an oblong ablation zone is produced.) The adjustment of the size and shape may be accomplished by, for example, selecting the ablation probe tip 100 with the appropriate annular aperture 120 to create the appropriate ablation zones 150, 160, 170. Another method to alter or control shape is by using pulse width modulation of the energy going out the probe. Properly positioning the ablation probe tip 100 using the procedures described in the Therapeutic Tooth Bud Ablation Properties and herein, the ablation zones are clearly circumferentially centered around the tooth bud and greatly reduce the incidence of any adjacent non-target tissue (e.g. nerves, teeth, etc.) being damaged.

The area of the ablation zones may be calculated using the following exemplary equation or other known area calculation methods (which may be more detailed and/or provide more accurate results):

$$Area = average\ length * average\ width * pi$$

The roundness of the ablation zones may be calculated using the following exemplary equation or other known roundness calculation methods (which may be more detailed and/or provide more accurate results):

$$\text{Roundness} = \text{average width}/\text{average length}$$

Other methods for determining the area and roundness of the ablation zone may be used including, but not limited to, direct observation, measurement, and other known or yet to be discovered empirical means for determining the area and roundness of the ablation zone.

Exemplary Use

There are many advantages to prophylactically preventing the formation of third molars using methods, systems, and procedures described both herein and in the Therapeutic Tooth Bud Ablation Properties. Earlier intervention is safer due to anatomy (the tooth bud is separated by 5-10 mm from the mandibular canal), tooth development (the crown of the adjacent first and/or second molars 95 is generally well developed), and improved healing (smaller surgical footprints reduce post-operation healing issues).

Using the apparatuses, methods/procedures, and systems described herein for inducing tooth agenesis, the clinical goal is predictable efficacy for inducing tooth agenesis with zero long-term adverse side effects. The apparatuses, methods/procedures, and systems described herein may be used in the apparatuses (customized surgical stents 80, virtual stents 82', 86', 88', and/or surgical kits), methods/procedures, and systems described in the Therapeutic Tooth Bud Ablation Properties. For example, the probes may be used with customized surgical stents 80 or virtual stents 82', 86', 88' for proper placement. A surgical kit (including an ablation probe system 50, custom surgical stent 80, and ablation energy dose tolerances) is configured with the goal of statistically maintaining +/−0.5 mm total ablation zone positioning control inside each tooth bud.

The following exemplary steps may be used for tooth agenesis (although the order may vary—e.g. the hand piece 52 may be connected to the ablation source 60 after the patient is seated):

Routine Screening Ages 6-14: Routine screening to determine the presence of tooth bud 92 (e.g. third molar tooth buds) formation in two-year increments between age 6 and age 14 because of the wide range of ages that reflects the degree of variability in the formation of tooth buds. The screening may be accomplished using scanning techniques such as low-dose digital panographic imaging techniques (which are common to at least most pediatric and most general dentists) or even new technologies such as ultrasound.

Diagnosis and Volume Scan Imaging: Once the presence of tooth buds has been diagnosed during screening, a pre-operative imaging step is performed to determine the three-dimensional location and volume of each tooth bud 92. This imaging can be practically accomplished using, for example, dental CBCT three-dimensional volume scans using a voxel resolution of 0.4 mm or better. The result is a three-dimensional digital volume scan.

Pre-Operation Impressions: A dental impression (conventional physical or digital dental impression) is obtained of the teeth and soft tissue (gums) in at least the quadrant of interest. This impression captures the surface of the gum tissue and detail of the teeth. Erupted first and/or second molars 95 and/or the primary dentition are used to physically stabilize surgical stent(s) 80. The creation of digital impressions is described in more detail in the Therapeutic Tooth Bud Ablation Properties.

Doctor's Prescription for Services: In one preferred method, a dental professional may complete and electronically sign an online prescription form. The electronically signed prescription is preferably completed with the uploading of the three-dimensional digital image (e.g. digital CBCT image) and at least one dental impression.

Ablation Probe Tip 100: The ablation probe tip 100 will have a defined or known ablation zone 150, 160, 170. The ablation probe tip 100 will have a defined or known depth of penetration. The ablation probe tip 100 will preferably be self-introducing through the gingival tissue 94 into the tooth bud 92. In practice, a family of ablation probe tips 100 may be produced and shipped in a surgical kit.

Creation of Custom Surgical Stent 80: The custom surgical stent 80 may be fabricated using the surgical stent design software suite that may be implemented as one or more programs, subprograms, applications, or modules.

The three-dimensional digital image and at least one dental impression are imported into the surgical stent design software suite. The specific ablation probe tip 100 or possible ablation probe tips 100, and the specifications therefore, are preferably known by (or provided to) the surgical stent design software suite so that the surgical stent design software suite can take the profile, dimensions, and/or capabilities (e.g. power density) of the ablation probe tip(s) 100 into consideration when designing the surgical stent 80. The surgical stent design software suite designs the surgical stent 80 with at least one surgical guide 82 and at least one mechanical stop 86 to guide and limit the placement of the ablation probe tip 100 into the tooth bud 92. (Put another way, the surgical stent design software suite calculates and provides ideal probe positioning and entry angle data and depth data that is required for optimal placement of the ablation probe's center of ablation 124 into the targeted tooth bud 92 with a total system tolerance of +/−0.5 mm for total ablation zone positioning control. This information may then be used to calculate the data necessary to create the at least one surgical guide 82 and at least one mechanical stop 86.) The surgical stent design software suite also designs the surgical stent 80 to mate with the patient's soft tissue (gums), preferably including the soft tissue covering the tooth bud 92. The surgical stent design software suite also designs the surgical stent 80 to mate with the patient's erupted teeth (e.g. primary and/or permanent first and/or second molars 95) such that the erupted teeth act as physical rests to hold the surgical stent 80 in place.

The surgical stent design software suite designs and fabricates custom surgical stents 80 in accordance with the methods discussed in the Therapeutic Tooth Bud Ablation Properties and known methods. Further, the surgical stent design software suite preferably formats the information about the custom designed surgical stent to be held as at least one output file (e.g. an *.stl output file). The output file(s) may be used for creating the surgical stent 80 using, for example, three-dimensional printing. In other instances, the output files may result in mapping a virtual stent 82', 86', 88'.

The surgical stent design software suite may work with CBCT software or may include custom software enhancements in CBCT software that assists in the rapid design and manufacturing of the custom surgical stents 80.

Figure 18:
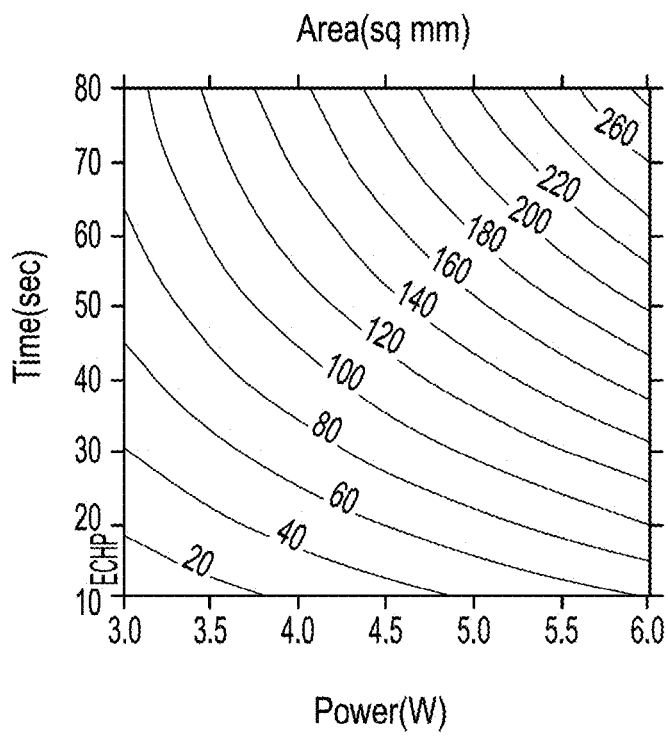
FIG. 18 shows the effects of power and time on the cross-sectional ablation zone area in an exemplary modeling that describes the volume of ablation.

Determination of Optimal Settings: The surgical stent design software suite preferably calculates and/or defines the optimum intra-operative ablation power and time settings (power and time dosage). (FIG. 18 shows the effects of power and time on the ablation area in an exemplary modeling.) The determination of ideal power and time (duration) settings for ablation take into consideration factors including, but not limited to, the profile of the ablation probe systems 50 (e.g. the zone(s) 150, 160, 170 produced by the ablation probe tip(s) 100), the tooth bud dimensions (computed from the volume scan images in the surgical stent design software suite), and the patient's age (during the ages of 6-12, a patient's tooth buds will generally have a diameter in the range of 4 mm to 12 mm). Ablation dose energy and treatment times are preferably incrementally compensated for increased tooth bud volumes. These patient and tooth-specific settings are then stored in a database (e.g. a volume scan information technology file) for later upload to the ablation source 60 when the operator sets it up or it may be part of the custom surgical guide kit (e.g. a prescription).

Custom Surgical Kits: Components of the custom surgical stent may be fabricated using a surgical stent design software suite that may be implemented as one or more programs, subprograms, applications, or modules to control production and/or calculate digital data (e.g. parameter settings 64 and/or treatment time settings 66).

A custom surgical kit preferably includes necessary components for the procedure. These necessary components include, but are not limited to, at least one sterile custom surgical stent 80, at least one sterile probe tip (ablation probe tip 100), instructional paperwork (or an indication of where instructions may be found—e.g. online), the calculated optimal settings (or an indication of where the optimal settings may be found—e.g. online), and/or a patient identification key provided with the kit. The custom surgical kit is preferably disposable.

It should be noted that some of the custom surgical kit components may be combined. For example, the instructional paperwork may be a small card with a website address and the patient identification key. The user may enter the patient identification key at the website address to obtain the calculated optimal settings.

It should be noted that the "instructional paperwork" may be printed or may be accessed electronically (e.g. via a website, a CD, or a thumb drive).

The at least one ablation probe tip 100 in the surgical kit is matched to the patient's custom surgical stent 80. Alternatively, a family of probe tips (e.g. 2-10 ablation probe tips) may be included in the surgical kit to cover multiple possible tooth bud depth and tooth bud volume relationships. The family of probe tips would have probe tips of differing characteristics such as differing lengths (e.g. the distance from the tip mechanical stop 106 to the center of ablation 124 and/or the distance from the tip mechanical stop 106 to the insertion end 104), connection structure (e.g. the connections structure that mates with the hand piece 52) and/or widths. If a family of probe tips is provided, the correct ablation probe tip 100 would be clearly indicated or a method for determining the correct ablation probe tip 100 would be provided (e.g. color-coding on the manufactured stent with a table showing which ablation probe tip would be used for each color). Alternatively, the surgical kit may not include a probe tip, but instead include a specific indication as to the ablation probe tip 100 that is necessary (e.g. ablation probe tip 100 that is matched to the patient's custom surgical stent 80). This specific indication might include the brand, model, and size of the correct ablation probe tip 100. The ablation probe tip(s) 100 may be individually packaged (or packaged as a family), sterile, and disposable.

The custom surgical kit is preferably labeled and packaged. Labeling may be customized for each package to indicate information including, but not limited to, the patient's name (and/or other identifying information), part numbers, treating doctor's name (and/or other identifying information such as the address), and the patient identification key.

Operator Use of the Custom Surgical Kit to ablate a tooth bud 92 (without ablating overlaying gingival tissue 94) with minimal pain and minimal infection potential.

The operator sets up for the procedure by powering up the ablation generator (ablation source 60). On power up the correct procedure information or patient identification key (which may be any predetermined information or code) is preferably entered into the generator, which then accesses and downloads the patient's name and preprogrammed settings for each tooth to be ablated from a database (which may be a database controlled by a central company or one of many databases). The system may be structured such that the preprogrammed settings cannot be changed (i.e. an operator cannot input or adjust the power level or time settings).

The hand piece 52 is preferably functionally connected to the ablation source 60. The disposable ablation probe tip 100 is preferably also functionally attached to the ablation hand piece 52. The hand piece 52 may have a "chuck" (which may be a push-button electrical connector "chuck" that provides rapid and reliable setup and easy maintenance) into which the ablation probe tip 100 may be inserted and secured.

The operator may start the procedure by placing the surgical stent 80 onto the patient's teeth prior to administering local anesthetic. Then the local anesthetic (¼ carpule per site) is generally administered through the surgical guides 82 of the surgical stent 80, and directly into or around the tooth bud 92 by placing the tip of the needle into the predetermined physical location. Precision placement of the anesthetic reduces the quantity necessary for the procedure.

Once the patient is anesthetized, a waiting period is preferably provided to allow the anesthetic solution to physically dissipate to avoid altering the tooth bud's volume. During the waiting period, the operator may functionally connect the sterile ablation probe tip 100 to the hand piece 52 and power-on the ablation source 60 if these steps have not already been performed. The surgical stent 80 may also be reseated at this time.

When everything is ready, the operator begins performing the ablation procedure by reseating the surgical stent 80 (if it hasn't already been done), gripping the hand piece 52, and inserting the self-penetrating ablation probe tip 100 through the surgical guide 82 to a full stop to puncture and penetrate the oral mucosal tissue and come to a correct final stop position with the center of ablation 124 within in the tooth bud 92 (e.g. in the middle of the tooth bud 93). To verify full-stop positioning, the ablation probe tip 100 is pressed to a full stop to secure the probe tip shaft in the surgical stent 80 (and particularly to the area surrounding the surgical guide 82) to position the ablation probe tip 100 at the predetermined angle and depth of the probe tip's predetermined center of ablation 124 in the center of the tooth bud 92.

Once the ablation probe tip 100 is positioned so that the center of ablation 124 is in the center of the tooth bud 92, the ablation source 60 may be activated. Activation may be accomplished using a direct activator (button) or a remote activator (e.g. a wireless foot pedal) in order to deliver the total energy dose according to the patient-specific time/power levels.

Ablation times are set based upon the system power, predetermined tooth bud volume and other parameters. The ablation means 62 will preferably monitor the procedure progress. The ablation probe tip 100 output may be monitored by percentage of reflected energy in order to positively confirm delivery of the proper procedure ablation dose. A visual and/or audible signal may be provided to indicate a successful delivery of the ablation energy when the ablation is complete.

The operator then withdraws the ablation probe tip 100 and removes the surgical stent 80. No sutures are required and there is generally very little bleeding following the procedure. The patient is free to assume normal activities immediately.

Distinctions

The NEUWAVE™ Microwave Ablation System is described in the Background. It is described as being able to ablate lesions with consistency and control to help protect non-target tissue. More specifically, the NEUWAVE™ System and NEUWAVE PR Probe is described as having a burn pattern that controls the ablation distance past the probe tip. The NEUWAVE™ System always produces an oblong ablation zone that asymmetrically migrates up the shaft of the probe, which means the center of ablation is moving up the shaft during the procedure and the outer margins of the zone of ablation are moving up the shaft as the zone of ablation expands. The NEUWAVE System relies on coherent microwave emissions with at least ¼ wavelengths. Because of this, there is no physical ability to shape the ablation zone to alternative shapes using the NEUWAVE™ PR probe or NEUWAVE SYSTEM. Among the ways the invention described herein addresses the PR probe's limitations is by having a stationary center of ablation and eliminating asymmetric ablation pattern migration up the probe while also being able to shape effectively the pattern to fit the desired ablation pattern.

U.S. Pat. No. 7,611,508 to Yang et al. is discussed in the Background. Yang describes an antenna for microwave tumor ablation that has coaxial antenna conductors surrounded by an insulated sleeve of length and size promoting destructive interference of axial microwave energy passing inside and outside of the sleeve to limit migration of SAR power toward the skin. Yang's floating sleeve provides destructive cancellation or wave interference of the microwaves. Changing the position of the sleeves changes the effective size of the heating pattern as a result of changing the degree of destructive cancellation or wave interference. Yang, operating at 2.45 GHz, would have wavelengths operating at odd multiples of ½ the wavelength, which is 1*12.2 cm (122 mm)*0.5=6.1 cm (61 mm) or longer as higher odd multiples are used. This means that Yang operates using far field radiation regions of the electromagnetic field (EM) surrounding the antenna where microwaves can radiate in a coherent fashion. Among the ways the invention described herein addresses Yang's limitations is by eliminating ablation pattern migration up the probe by having a stationary center of ablation while also being able to effectively shape the pattern to fit the desired ablation pattern.

In contrast to the NEUWAVE PR Probe and Yang probe designs, which rely on far field coherent waveform, the ablation probes described herein function in the near field non-radiative (near field reactive) regions of the electromagnetic field (EM) surrounding the antenna where microwaves radiate in a noncoherent fashion. Near field reactive regions are generally considered to be wavelengths of $\lambda/2\pi \sim 0.159$ or less. The ablation probes described herein preferably operate at a wide range of wavelengths, but for soft tissue ablation at 2.45 GHz, the near field reactive aperture would preferably be less than 20 mm. For 12 GHz, the wavelength is shorter (e.g. 25 mm), which means the aperture and effective antenna length the probe preferably is 4 mm or less to provide optimal shaping and centering directed properties. The heat transfer layer 130 described herein is preferably able to take advantage of tissue quenching because there is no coherent waveform being emitted. In sharp contrast, the antenna described in the Yang reference starts with the shortest antenna length of 22 mm from the proximal end of the ablation probe and is elongated in increments of ½ wavelengths further up the ablation probe as the floating sleeve is moved further up the shaft (per Yang FIG. 6, the distances labeled with reference numbers 62a, 62b, and 62c) making ablation zone shaping in a space of less than 30 mm physically impossible.

Miscellaneous

It is to be understood that the inventions, examples, and embodiments described herein are not limited to particularly exemplified materials, methods, and/or structures. It is to be understood that the inventions, examples, and embodiments described herein are to be considered preferred inventions, examples, and embodiments whether specifically identified as such or not. The shown inventions, examples, and embodiments are preferred, but are not meant to be limiting unless specifically claimed, in which case they may limit the scope of that particular claim.

All references (including, but not limited to, publications, patents, and patent applications) cited herein, whether supra or infra, are hereby incorporated by reference in their entirety.

The terms and expressions that have been employed in the foregoing specification are used as terms of description and not of limitation, and are not intended to exclude equivalents of the features shown and described. While the above is a complete description of selected embodiments of the present invention, it is possible to practice the invention using various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that this description intended to cover all of the generic and specific features of the invention herein described and all statements of the scope of the invention that, as a matter of language, might be said to fall therebetween.

What is claimed is:

1. An ablation probe tip having a shaft with an insertion end, said ablation probe tip receiving ablation means from an ablation source, said ablation probe tip for ablating targeted tissue from within, said ablation probe tip comprising:
   (a) said shaft including a coaxial antenna, said coaxial antenna being a near field antenna, said coaxial antenna comprising:
      (i) an inner conductor;
      (ii) an annular dielectric insulator layer surrounding said inner conductor; and
      (iii) an annular outer conductor surrounding said annular dielectric insulator layer;
   (b) an annular aperture defined in said annular outer conductor toward said insertion end;
   (c) a center of ablation located within said inner conductor and surrounded by said annular aperture;
   (d) an annular heat transfer layer surrounding said coaxial antenna and spaced from said insertion end such that said annular aperture is between said annular heat transfer layer and said insertion end;
   (e) an annular tip cover at said insertion end, said annular tip cover surrounding and covering an end of said coaxial antenna and said annular aperture;
   (f) said center of ablation being a focal region from which said ablation means radiates through said annular aperture to form an ablation zone; and
   (g) said ablation zone having a predetermined shape selected from the group consisting of oblate, spherical, and oblong.

2. The ablation probe tip of claim 1, wherein said insertion end is a self-introducing insertion end.

3. The ablation probe tip of claim 1, wherein said insertion end is a self-introducing insertion end, said predetermined shape determined by an aperture offset, said aperture offset being a distance between said center of ablation and an annular edge of said annular heat transfer layer.

4. The ablation probe tip of claim 1, said predetermined shape determined by an aperture offset, said aperture offset being a distance between said center of ablation and an annular edge of said annular heat transfer layer.

5. The ablation probe tip of claim 1, wherein said insertion end is a self-introducing insertion end, said predetermined shape determined by an aperture offset, said aperture offset being a distance between said center of ablation and an annular edge of said annular heat transfer layer, wherein an oblate ablation zone has a relatively short aperture offset, an oblong ablation zone has a relatively long aperture offset, and a spherical ablation zone has an aperture offset between said aperture offsets of said oblate ablation zone and said oblong ablation zone.

6. The ablation probe tip of claim 1, said predetermined shape determined by an aperture offset, said aperture offset being a distance between said center of ablation and an annular edge of said annular heat transfer layer, wherein an oblate ablation zone has a relatively short aperture offset, an oblong ablation zone has a relatively long aperture offset, and a spherical ablation zone has an aperture offset between said aperture offsets of said oblate ablation zone and said oblong ablation zone.

7. The ablation probe tip of claim 1, said predetermined shape determined by an aperture offset, said aperture offset being a distance between said center of ablation and an annular edge of said annular heat transfer layer, wherein the ablation zone the aperture offset are selected from the group consisting of:
   (a) the ablation zone is an oblate shaped ablation zone, and the aperture offset is less than 1 mm;
   (b) the ablation zone is a spherical shaped ablation zone, and the aperture offset is in the range of 1 mm to 4 mm; and
   (c) the ablation zone is an oblong shaped ablation zone, and the aperture offset is greater than 4 mm.

8. The ablation probe tip of claim 1, said predetermined shape determined by an aperture offset, said aperture offset being a distance between said center of ablation and an annular edge of said annular heat transfer layer, wherein an oblate ablation zone has a relatively short aperture offset, an oblong ablation zone has a relatively long aperture offset, and a spherical ablation zone has an aperture offset between said aperture offsets of said oblate ablation zone and said oblong ablation zone, wherein the ablation zone the aperture offset are selected from the group consisting of:
   (a) the ablation zone is an oblate shaped ablation zone, and the aperture offset is less than 1 mm;
   (b) the ablation zone is a spherical shaped ablation zone, and the aperture offset is in the range of 1 mm to 4 mm; and
   (c) the ablation zone is an oblong shaped ablation zone, and the aperture offset is greater than 4 mm.

9. The ablation probe tip of claim 1, said coaxial antenna further comprising an insulation annular layer annularly surrounding said annular outer conductor, said annular heat transfer layer annularly surrounding said insulation annular layer.

10. The ablation probe tip of claim 1, wherein the annular heat transfer layer is an outermost layer.

11. The ablation probe tip of claim 1, further comprising an antenna end load positioned between said annular aperture and said insertion end.

12. The ablation probe tip of claim 1, further comprising an antenna end load positioned between said annular aperture and said insertion end, said antenna end load concentrating energy density and increasing power loading.

13. The ablation probe tip of claim 1, said annular heat transfer layer having high thermal conductivity and being electrically conductive.

14. The ablation probe tip of claim 1, said annular aperture exposing an annular ring of said annular dielectric insulator layer.

15. The ablation probe tip of claim 1 wherein, during use, the center of ablation remains substantially stationary.

16. The ablation probe tip of claim 1 wherein the tip cover is made from a material having the following properties:
   (a) high radio translucency;
   (b) low thermal conductivity; and
   (c) electrically nonconductive.

17. The ablation probe tip of claim 1 wherein the tip cover is made from a material having the following properties:
   (a) high radio translucency;
   (b) low thermal conductivity; and
   (c) electrically nonconductive;

(d) wherein, during use, the center of ablation remains substantially stationary.

18. The ablation probe tip of claim 1 wherein the annular heat transfer layer is configured to, in use, be quenched by transferring thermal energy from said annular heat transfer layer into soft tissue surrounding said annular heat transfer layer.

19. The ablation probe tip of claim 1 wherein the annular heat transfer layer is configured to, in use, be quenched by transferring thermal energy from said annular heat transfer layer into soft tissue surrounding said annular heat transfer layer, wherein, during use, the center of ablation remains substantially stationary.

20. The ablation probe tip of claim 1, wherein, in use, the exiting of the ablation means entails energy acting in the near field reactive region of the antenna.

21. The ablation probe tip of claim 1, wherein, in use, the exiting of the ablation means entails energy acting in the near field reactive region of the antenna, wherein the coaxial antenna has an effective antenna length of $\lambda/2\pi$ or less.

22. A surgical ablation kit, comprising:
(a) an ablation probe tip, an ablation source, a hand piece, a stent, and a prescription; and
(b) said ablation probe tip having a shaft with an insertion end, said ablation probe tip receiving ablation means from said ablation source, said ablation probe tip for ablating targeted tissue from within, said ablation probe tip comprising:
   (i) said shaft including a coaxial antenna, said coaxial antenna is a near field antenna, said coaxial antenna comprising:
      (A) an inner conductor;
      (B) an annular dielectric insulator layer surrounding said inner conductor; and
      (C) an annular outer conductor surrounding said annular dielectric insulator layer;
   (ii) an annular aperture defined in said annular outer conductor toward said insertion end;
   (iii) a center of ablation located within said inner conductor and surrounded by said annular aperture;
   (iv) an annular heat transfer layer surrounding said coaxial antenna and spaced from said insertion end such that said annular aperture is between said annular heat transfer layer and said insertion end;
   (v) an annular tip cover at said insertion end, said annular tip cover surrounding and covering an end of said coaxial antenna and said annular aperture;
   (vi) said center of ablation being a focal region from which said ablation means radiates through said annular aperture to form an ablation zone; and
   (vii) said ablation zone having a predetermined shape selected from the group consisting of oblate, spherical, and oblong.

23. The surgical ablation kit of claim 22, said prescription including at least one setting or parameter selected from the group consisting of:
(a) ablation energy dose tolerances;
(b) levels of energy; and
(c) duration of energy deliverance.

24. The surgical ablation kit of claim 22, said ablation probe tip, in use, having peak temperature intra-operative control selected from the group consisting of:
(a) passive cooling;
(b) active cooling; and
(c) a combination of passive and active cooling.

25. The surgical ablation kit of claim 22, said surgical kit, in use, allowing for at least one intra-operative control selected from the group consisting of:
(a) volume of said ablation zone; and
(b) diameter of said ablation zone.

26. An ablation probe tip having a shaft with an insertion end, said ablation probe tip receiving ablation means from an ablation source, said ablation probe tip for ablating targeted tissue, said ablation probe tip comprising:
(a) said shaft including a coaxial antenna, said coaxial antenna being a near field antenna;
(b) an annular aperture defined in at least one outer layer of said coaxial antenna toward said insertion end;
(c) a center of ablation located within said coaxial antenna and surrounded by said annular aperture;
(d) an annular heat transfer layer surrounding said coaxial antenna and spaced from said insertion end such that said annular aperture is between said annular heat transfer layer and said insertion end;
(e) said center of ablation being a focal region from which said ablation means radiates through said annular aperture to form an ablation zone; and
(f) said ablation zone having a predetermined shape selected from the group consisting of oblate, spherical, and oblong.

27. An ablation probe tip having a shaft with an insertion end, said ablation probe tip receiving ablation means from an ablation source, said ablation probe tip for ablating targeted tissue, said ablation probe tip comprising:
(a) said shaft including a coaxial antenna, said coaxial antenna being a near field antenna;
(b) an annular aperture defined in at least one outer layer of said coaxial antenna toward said insertion end;
(c) a center of ablation located within said coaxial antenna and surrounded by said annular aperture, said center of ablation being a focal region from which said ablation means radiates through said annular aperture to form an ablation zone;
(d) an annular heat transfer layer surrounding said coaxial antenna, said annular heat transfer layer having an annular edge that is the closest part of said annular heat transfer layer to said annular aperture, said annular edge spaced from said insertion end such that said annular aperture is between said annular heat transfer layer and said insertion end;
(e) an aperture offset, said aperture offset being a distance between said center of ablation and said annular edge of said annular heat transfer layer; and
(f) said ablation zone having a predetermined shape determined by said aperture offset, such that a relatively short length aperture offset causes said ablation zone to be oblate, a relatively long length aperture offset causes said ablation zone to be oblong, and a medium length aperture offset causes said ablation zone to be spherical.

* * * * *